United States Patent
Cohn et al.

(10) Patent No.: US 8,728,099 B2
(45) Date of Patent: May 20, 2014

(54) SURGICAL FASTENERS, APPLICATOR INSTRUMENTS, AND METHODS FOR DEPLOYING SURGICAL FASTENERS

(75) Inventors: Simon Cohn, Rutherford, NJ (US); Michael Cardinale, Manalapan, NJ (US); Richard P. Fuchs, Cincinnati, OH (US); Matthew David Daniel, Lebanon, OH (US); Jeremy David Jarrett, Cincinnati, OH (US)

(73) Assignee: Ethicon, Inc., Somerville, NJ (US)

( * ) Notice: Subject to any disclaimer, the term of this patent is extended or adjusted under 35 U.S.C. 154(b) by 484 days.

(21) Appl. No.: 12/464,177

(22) Filed: May 12, 2009

(65) Prior Publication Data

US 2010/0292713 A1 Nov. 18, 2010

(51) Int. Cl.
*A61B 17/10* (2006.01)

(52) U.S. Cl.
USPC .......................................... 606/143

(58) Field of Classification Search
CPC . A61B 17/12; A61B 17/1285; A61B 17/0682
USPC .......... 606/75, 142, 143, 151, 157, 158, 219, 606/220, 221; 227/175.1–182.1, 19, 902
See application file for complete search history.

(56) References Cited

U.S. PATENT DOCUMENTS

| | | |
|---|---|---|
| 575,157 A | 1/1897 | Howell |
| 1,311,903 A | 8/1919 | Leschander |
| 2,283,814 A | 5/1942 | LaPlace |
| 2,786,450 A * | 3/1957 | Jacobus et al. ................. 92/30 |
| 3,236,142 A | 2/1966 | Bradway |
| 3,740,994 A | 6/1973 | DeCarlo, Jr. |
| 3,757,629 A | 9/1973 | Schneider |
| 4,090,337 A | 5/1978 | Szekeres |
| 4,220,070 A | 9/1980 | Anstett |
| 4,235,238 A | 11/1980 | Ogiu et al. |

(Continued)

FOREIGN PATENT DOCUMENTS

| | | |
|---|---|---|
| EP | 432320 | 6/1991 |
| EP | 0770354 | 5/1997 |

(Continued)

OTHER PUBLICATIONS

Covidien ProTack, www.covidien.com, 3 pp (2009).

(Continued)

*Primary Examiner* — Thomas McEvoy
(74) *Attorney, Agent, or Firm* — Doherty IP Law Group LLC

(57) ABSTRACT

A firing system for an applicator instrument adapted to dispense surgical fasteners includes a housing, an elongated shaft extending from the housing, a firing rod disposed within the elongated shaft, a firing rod release engageable with the firing rod for preventing distal movement of the firing rod during at least one stage of a firing cycle, a trigger mounted to the housing, and a firing spring having a first end connected with the firing rod and a second end adapted for being sequentially coupled and decoupled from the trigger during the firing cycle. The firing cycle includes an initial stage in which the trigger is open and decoupled from the energy storing element, and the firing spring is at least partially compressed, and a piloting stage during which the firing rod release is disengaged from the firing rod for enabling distal movement of the firing rod.

20 Claims, 43 Drawing Sheets

(56) References Cited

U.S. PATENT DOCUMENTS

| | | | |
|---|---|---|---|
| 4,325,376 A | 4/1982 | Klieman et al. |
| 4,428,376 A | 1/1984 | Mericle |
| 4,450,998 A | 5/1984 | Ruskin |
| 4,454,875 A | 6/1984 | Pratt et al. |
| 4,471,780 A | 9/1984 | Menges et al. |
| 4,478,220 A | 10/1984 | DiGiovanni et al. |
| 4,534,350 A | 8/1985 | Golden et al. |
| 4,534,352 A | 8/1985 | Korthoff |
| 4,548,202 A | 10/1985 | Duncan |
| 4,570,623 A | 2/1986 | Ellison et al. |
| D286,422 S | 10/1986 | Dickerson |
| 4,624,254 A | 11/1986 | McGarry et al. |
| 4,627,437 A | 12/1986 | Bedi et al. |
| 4,635,637 A | 1/1987 | Schreiber |
| 4,669,473 A | 6/1987 | Richards et al. |
| 4,696,300 A | 9/1987 | Anderson |
| 4,873,976 A | 10/1989 | Schreiber |
| 4,976,715 A | 12/1990 | Bays et al. |
| 5,002,562 A | 3/1991 | Oberlander |
| 5,053,038 A | 10/1991 | Sheehan |
| 5,104,395 A | 4/1992 | Thornton et al. |
| 5,203,864 A | 4/1993 | Phillips |
| 5,258,012 A | 11/1993 | Luscombe et al. |
| 5,290,297 A | 3/1994 | Phillips |
| 5,328,077 A | 7/1994 | Lou |
| 5,439,468 A | 8/1995 | Schulze et al. |
| 5,443,198 A | 8/1995 | Viola et al. |
| 5,470,010 A | 11/1995 | Rothfuss et al. |
| 5,520,700 A | 5/1996 | Beyar et al. |
| 5,522,797 A | 6/1996 | Grimm |
| 5,522,817 A | 6/1996 | Sander et al. |
| 5,582,616 A | 12/1996 | Bolduc et al. |
| 5,593,421 A | 1/1997 | Bauer |
| 5,601,573 A | 2/1997 | Fogelberg et al. |
| D378,409 S | 3/1997 | Michelson |
| 5,755,726 A * | 5/1998 | Pratt et al. ............... 606/143 |
| 5,810,882 A | 9/1998 | Bolduc et al. |
| 5,827,298 A | 10/1998 | Hart et al. |
| 5,830,221 A | 11/1998 | Stein et al. |
| 5,833,700 A | 11/1998 | Fogelberg et al. |
| 5,843,084 A | 12/1998 | Hart et al. |
| 5,921,997 A | 7/1999 | Fogelberg et al. |
| 5,951,574 A | 9/1999 | Stefanchik et al. |
| 5,993,476 A | 11/1999 | Groiso |
| 5,997,552 A | 12/1999 | Person et al. |
| 6,083,242 A | 7/2000 | Cook |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,425,900 B1 | 7/2002 | Knodel et al. |
| 6,616,669 B2 | 9/2003 | Ogilvie et al. |
| 6,666,872 B2 | 12/2003 | Barreiro et al. |
| 6,716,226 B2 | 4/2004 | Sixto et al. |
| 6,773,437 B2 | 8/2004 | Ogilvie et al. |
| 6,779,701 B2 | 8/2004 | Bailly |
| 7,104,999 B2 | 9/2006 | Overaker |
| 7,105,010 B2 | 9/2006 | Hart et al. |
| 7,112,214 B2 | 9/2006 | Peterson et al. |
| 8,579,920 B2 | 11/2013 | Nering et al. |
| 2002/0068947 A1 | 6/2002 | Kuhns et al. |
| 2002/0156500 A1 | 10/2002 | Storz-Irion et al. |
| 2004/0034357 A1 | 2/2004 | Beane et al. |
| 2004/0138705 A1 | 7/2004 | Heino et al. |
| 2004/0204723 A1 | 10/2004 | Kayan |
| 2004/0260343 A1 | 12/2004 | Leclair |
| 2005/0059984 A1 | 3/2005 | Chanduszko et al. |
| 2005/0182444 A1 | 8/2005 | Peterson et al. |
| 2005/0240222 A1 | 10/2005 | Shipp |
| 2005/0283189 A1 | 12/2005 | Rosenblatt |
| 2005/0288689 A1 | 12/2005 | Kammerer et al. |
| 2006/0079913 A1 | 4/2006 | Whitfield et al. |
| 2007/0088390 A1 | 4/2007 | Paz et al. |
| 2007/0142838 A1 | 6/2007 | Jordan |
| 2007/0208358 A1 | 9/2007 | Kayan |
| 2008/0045978 A1 | 2/2008 | Kuhns et al. |
| 2008/0065153 A1 | 3/2008 | Allard et al. |
| 2008/0065154 A1 | 3/2008 | Allard et al. |
| 2008/0217376 A1 * | 9/2008 | Clauson et al. ............ 227/181.1 |
| 2008/0275471 A1 | 11/2008 | Viola |
| 2009/0030434 A1 | 1/2009 | Paz et al. |
| 2009/0036903 A1 * | 2/2009 | Ino et al. .................. 606/143 |
| 2009/0118734 A1 | 5/2009 | Bhatnagar et al. |
| 2010/0270354 A1 | 10/2010 | Rimer et al. |
| 2010/0292710 A1 | 11/2010 | Daniel et al. |
| 2010/0292712 A1 | 11/2010 | Nering et al. |
| 2010/0292715 A1 | 11/2010 | Nering et al. |
| 2010/0327042 A1 | 12/2010 | Amid et al. |
| 2011/0079627 A1 | 4/2011 | Cardinale et al. |
| 2012/0071566 A1 | 3/2012 | Kelly et al. |
| 2012/0175401 A1 | 7/2012 | Bachman |
| 2013/0153627 A1 | 6/2013 | Euteneuer et al. |
| 2013/0153628 A1 | 6/2013 | Euteneuer |
| 2013/0218177 A1 | 8/2013 | Miksza et al. |

FOREIGN PATENT DOCUMENTS

| | | |
|---|---|---|
| EP | 1090591 | 6/2001 |
| EP | 1138263 | 10/2001 |
| JP | 06-233772 | 8/1994 |
| WO | 9944525 | 9/1999 |
| WO | 2007011994 | 1/2007 |

OTHER PUBLICATIONS

Sofradim I-Clip, www.surgicalproductsmag.com, 2 pp (2009).
Davol PermaSorb, www.bardnordic.com, 4 pp (2009).
Covidien AbsorbaTacks, www.covidien.com, 2 pp (2009).
Easy-Lap iMesh Tacker, www.easy-lap.com, 1p (2009).
International Search Report for International Application No. PCT/US2010/033963 dated Oct. 22, 2010, 5pp.
International Search Report for International Application No. PCT/US2010/033956 dated Jul. 22, 2010, 4 pp.
International Search Report for International Application No. PCT/US2010/033959 dated Aug. 2, 2010, 5pp.
International Search Report for International Application No. PCT/US2010/033960 dated Aug. 2, 2010, 5pp.

* cited by examiner

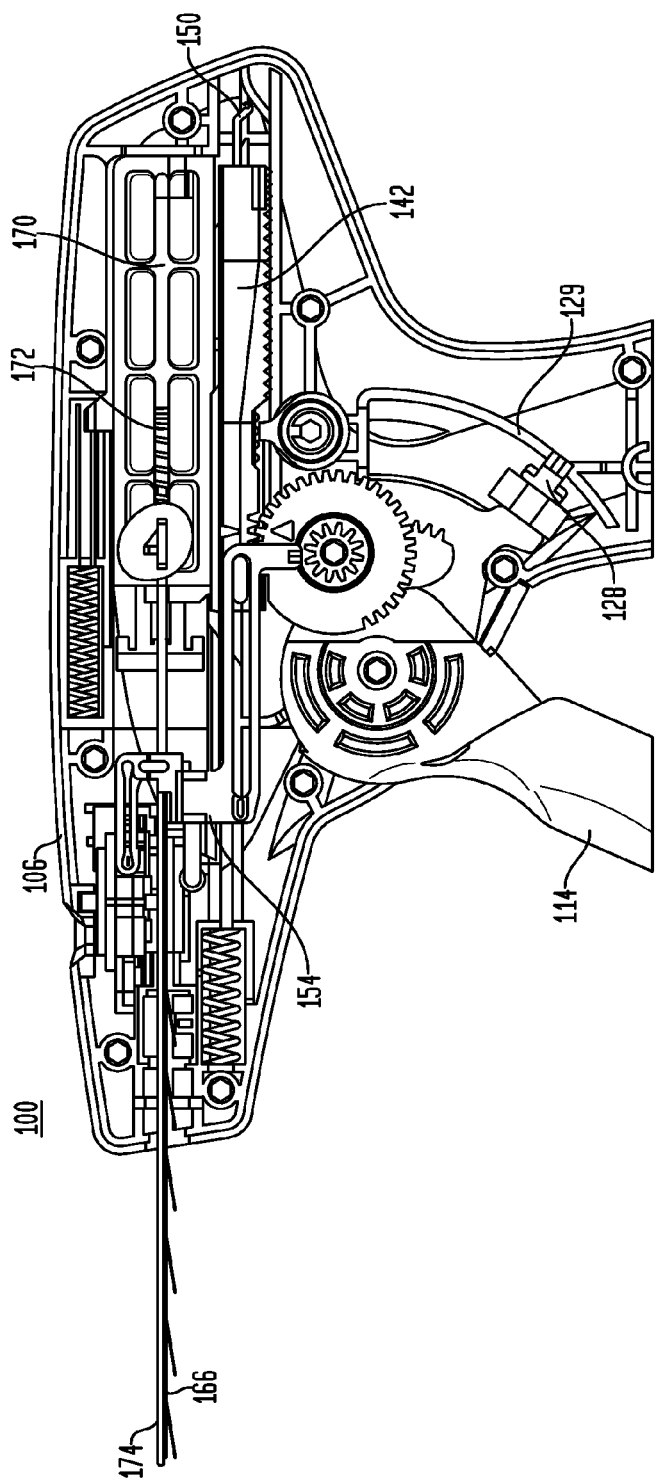
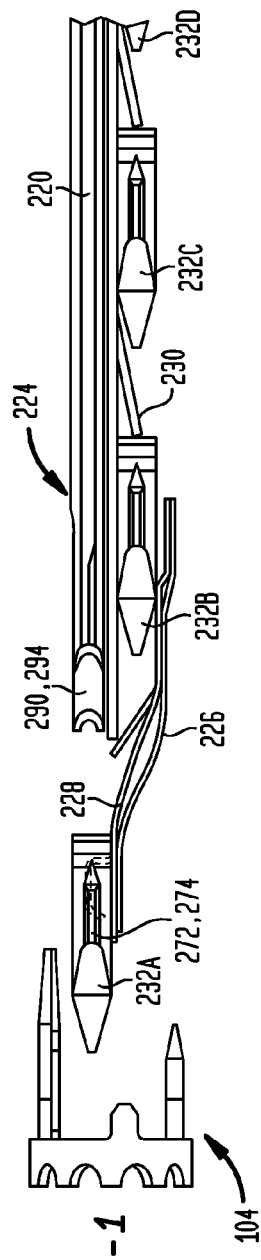
FIG. 11A
FIG. 11A-1

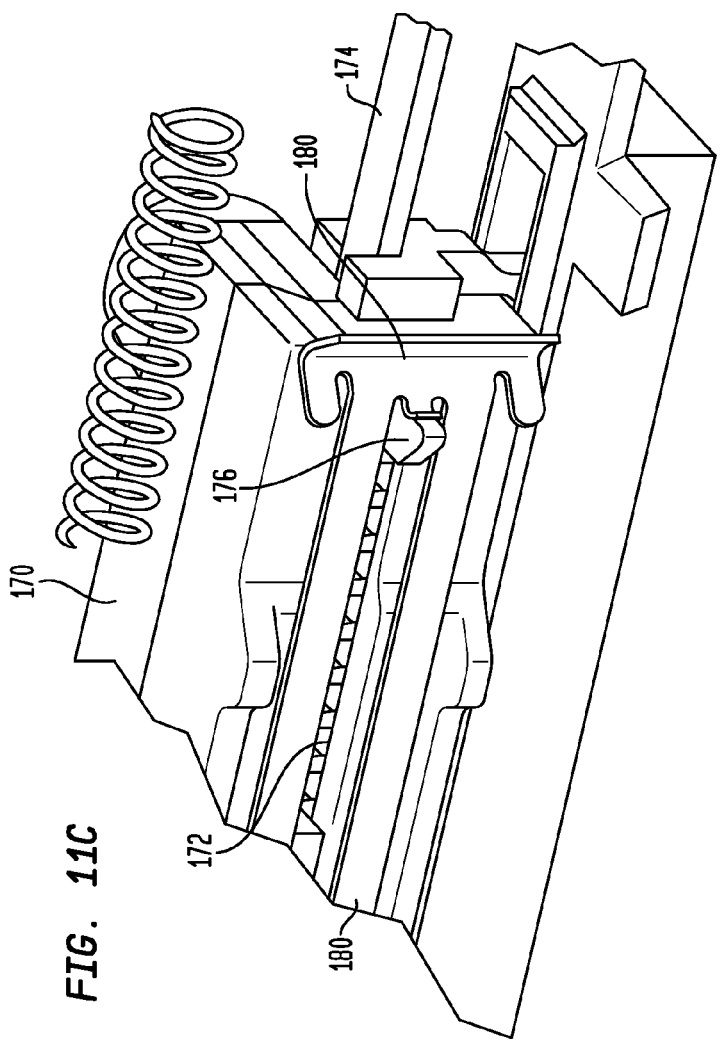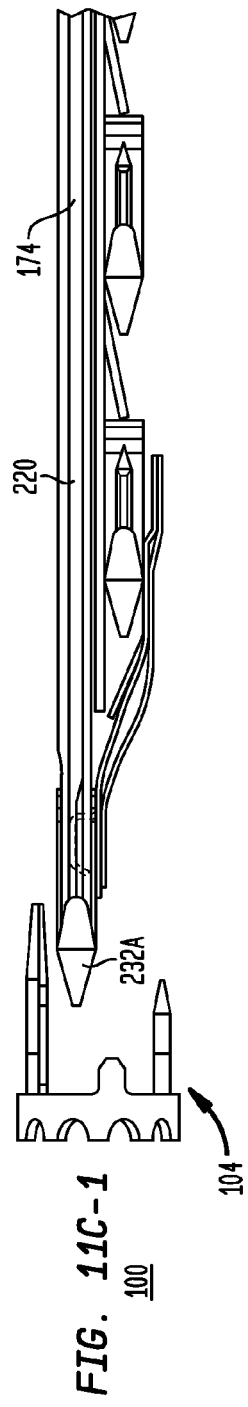

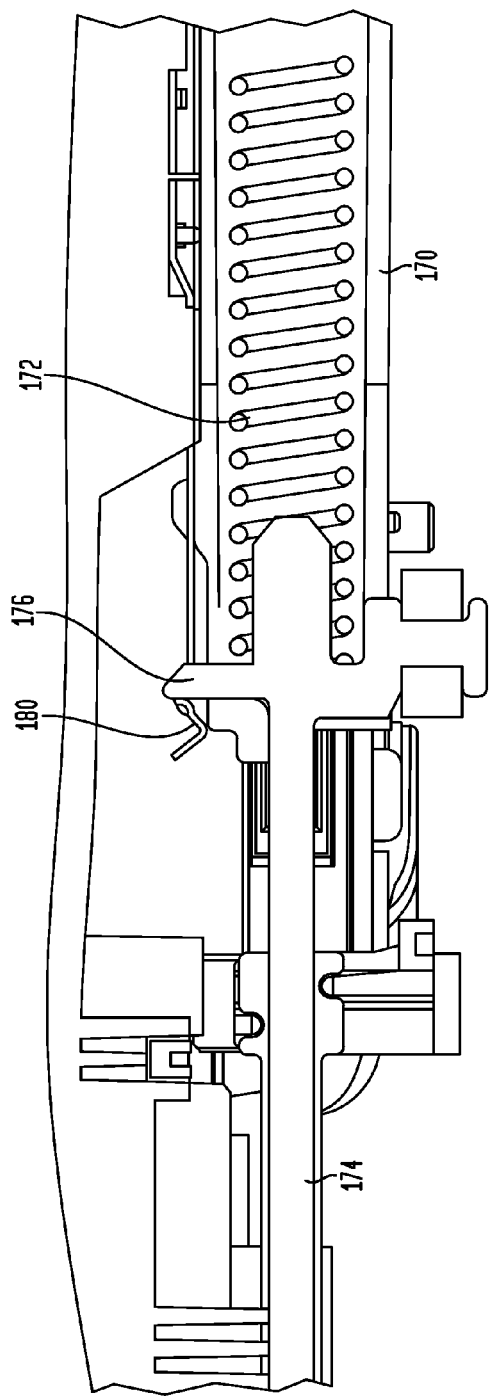
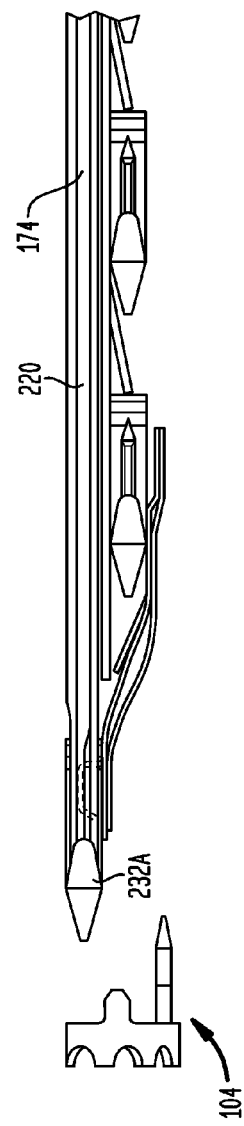
FIG. 11D
FIG. 11D-1

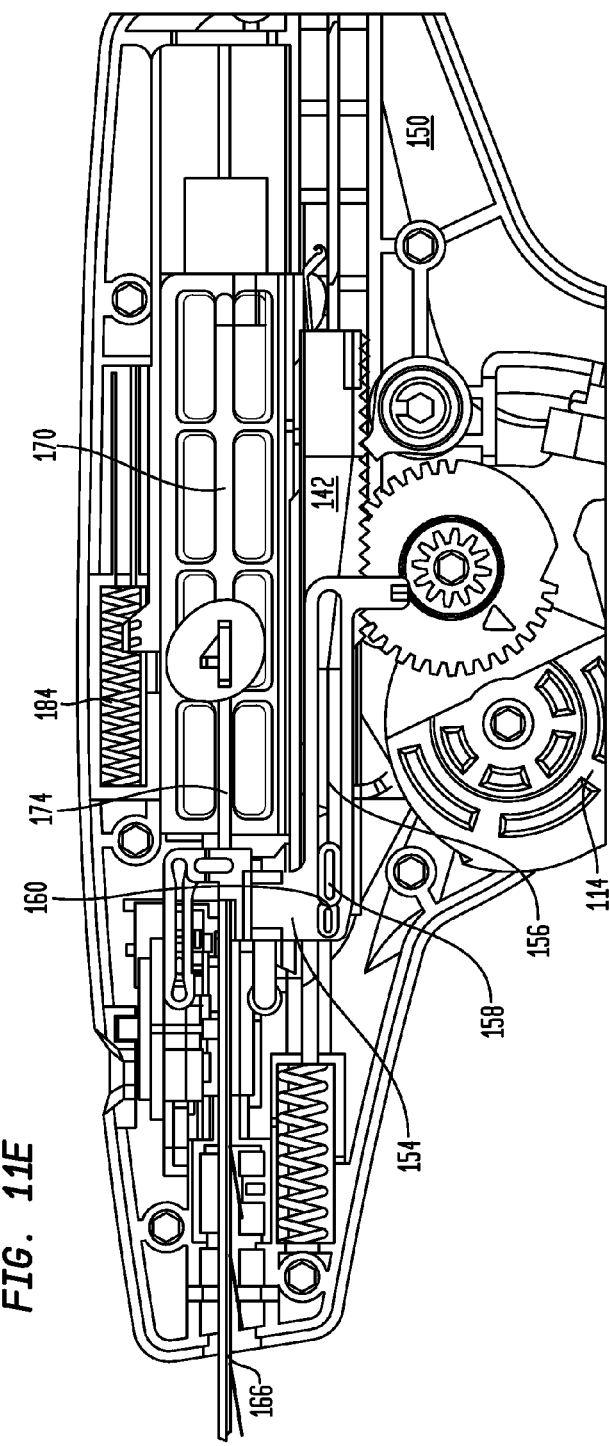
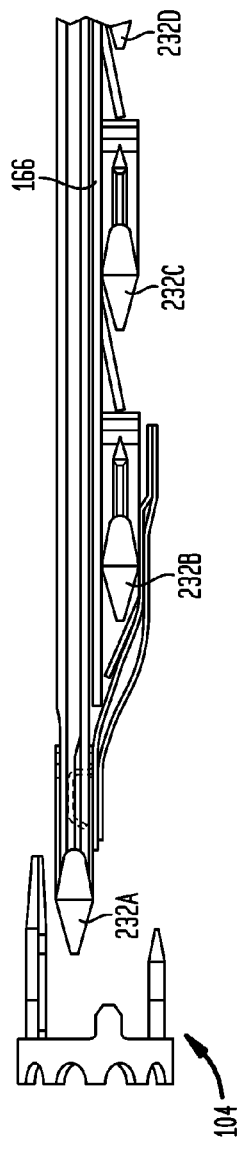
FIG. 11E
FIG. 11E-1

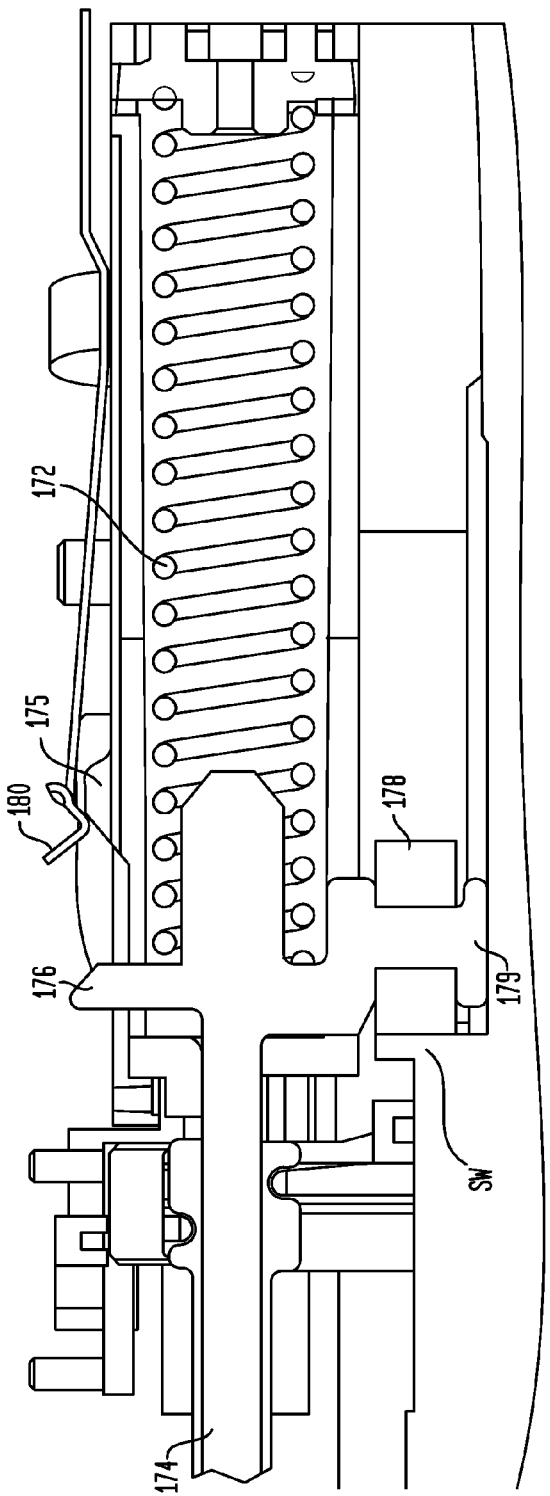
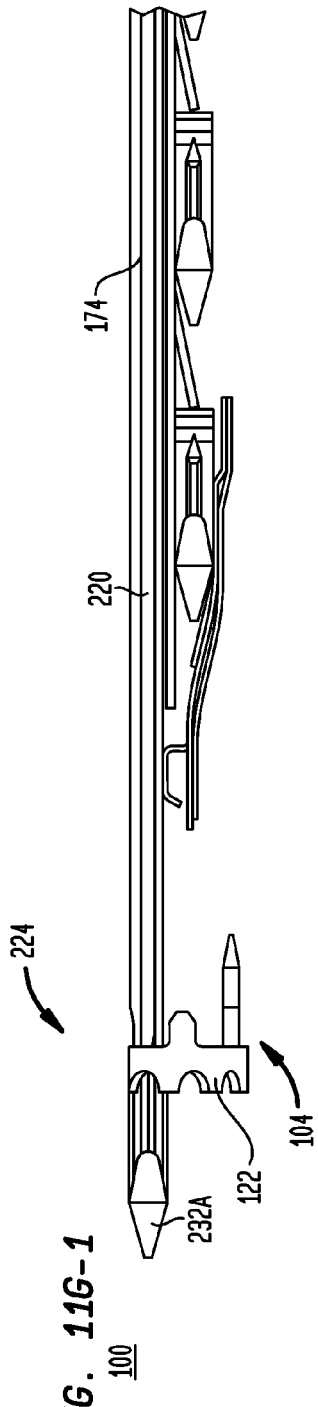
FIG. 11G
FIG. 11G-1

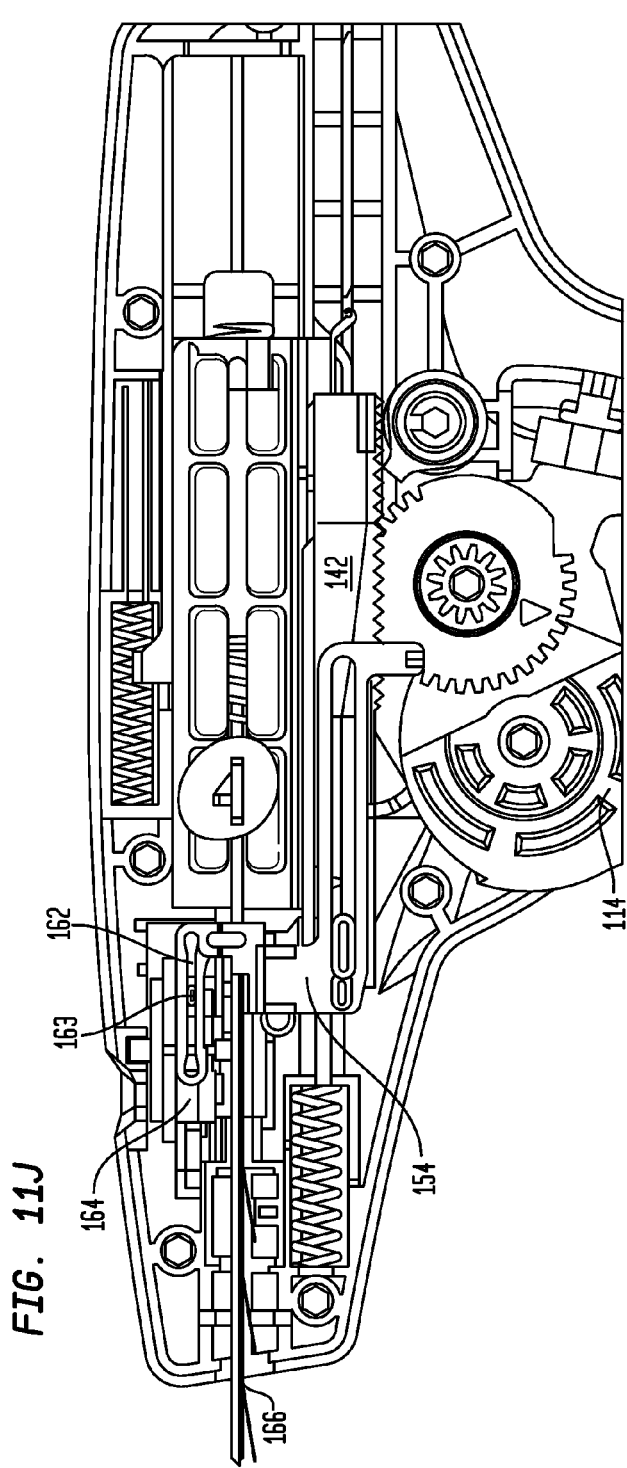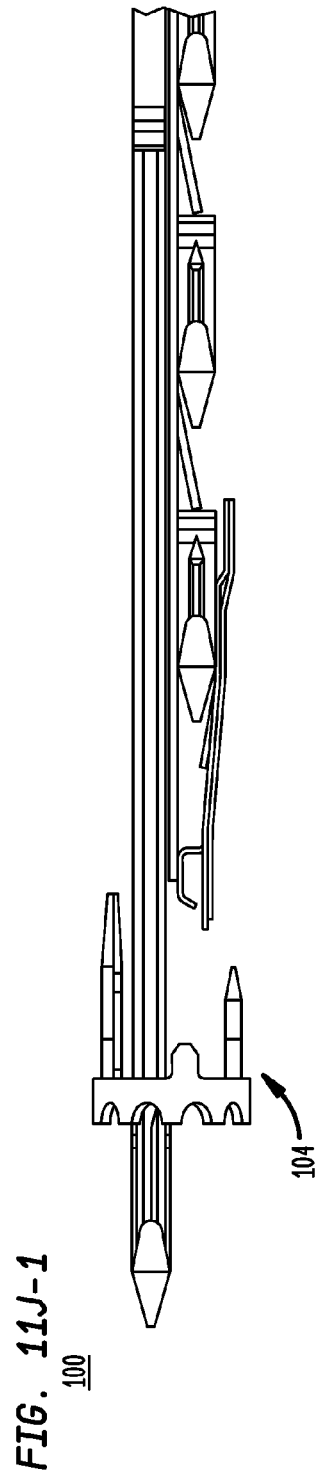

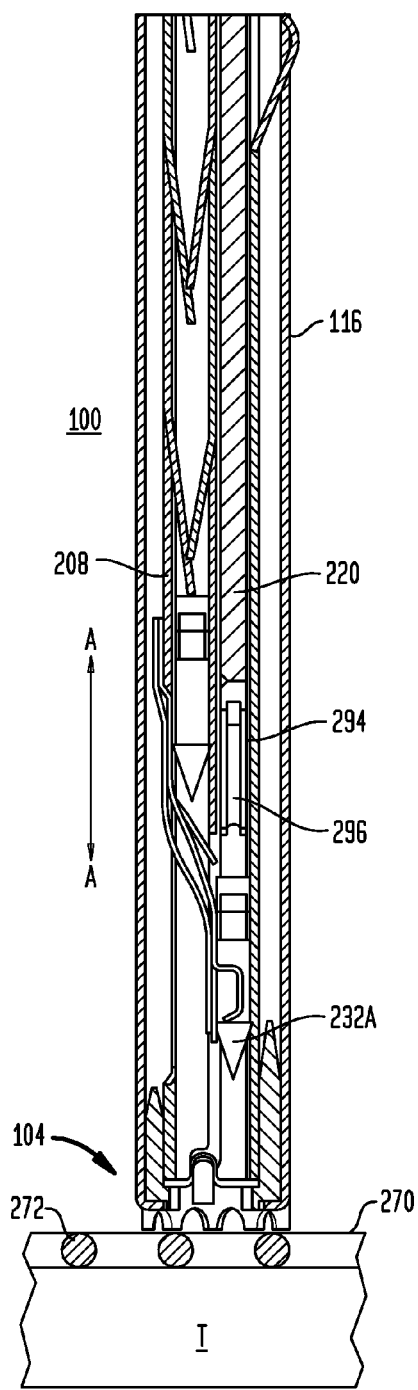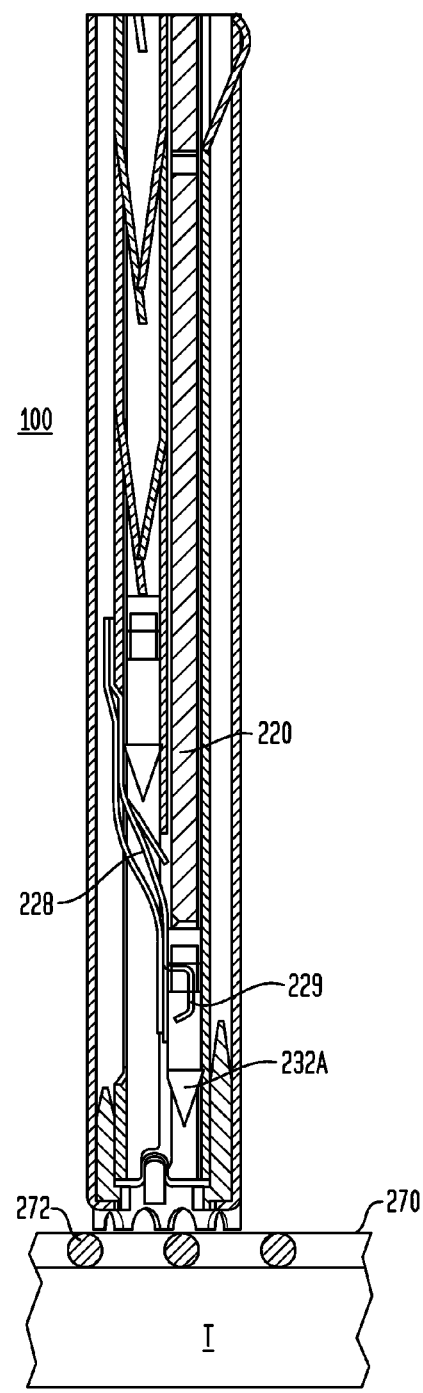

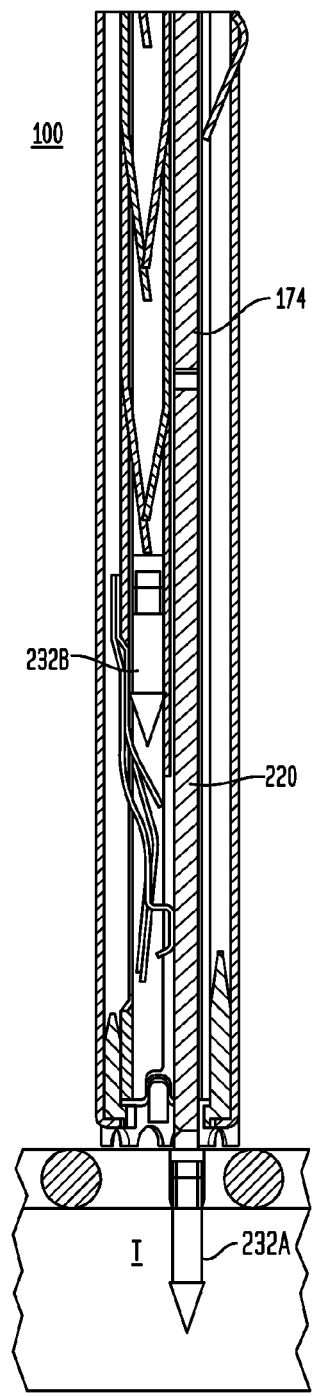
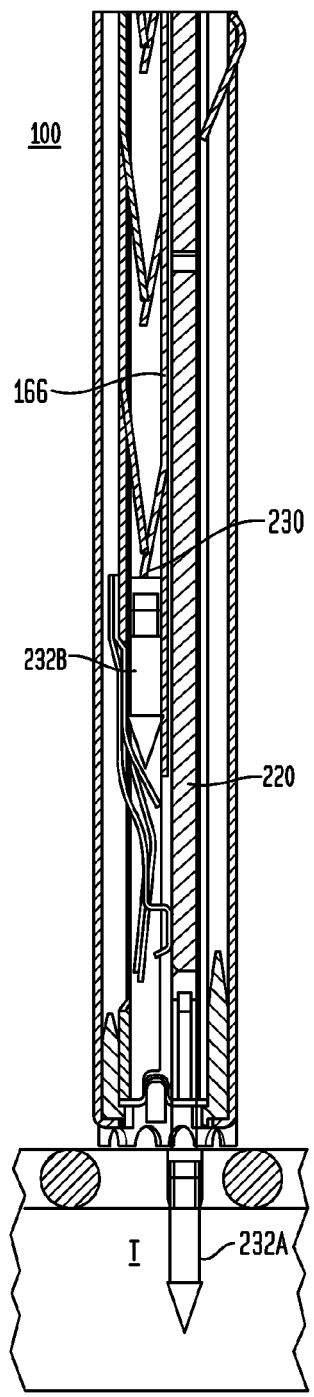
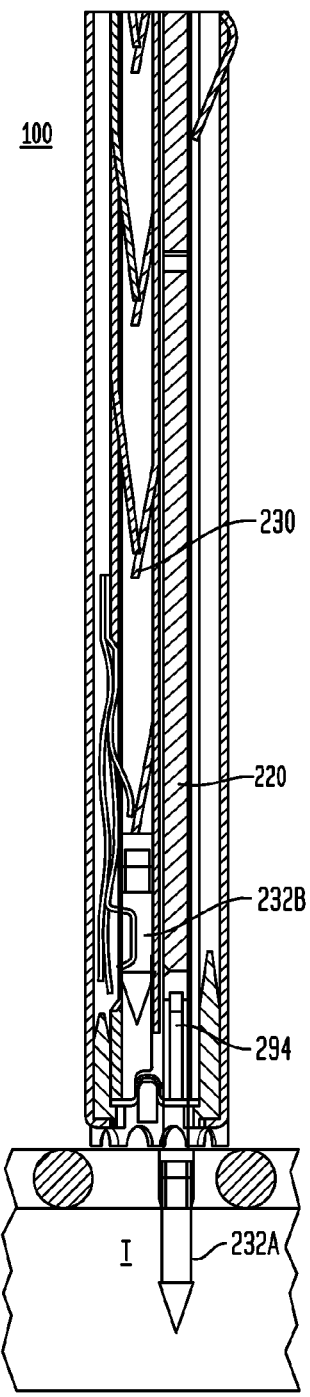

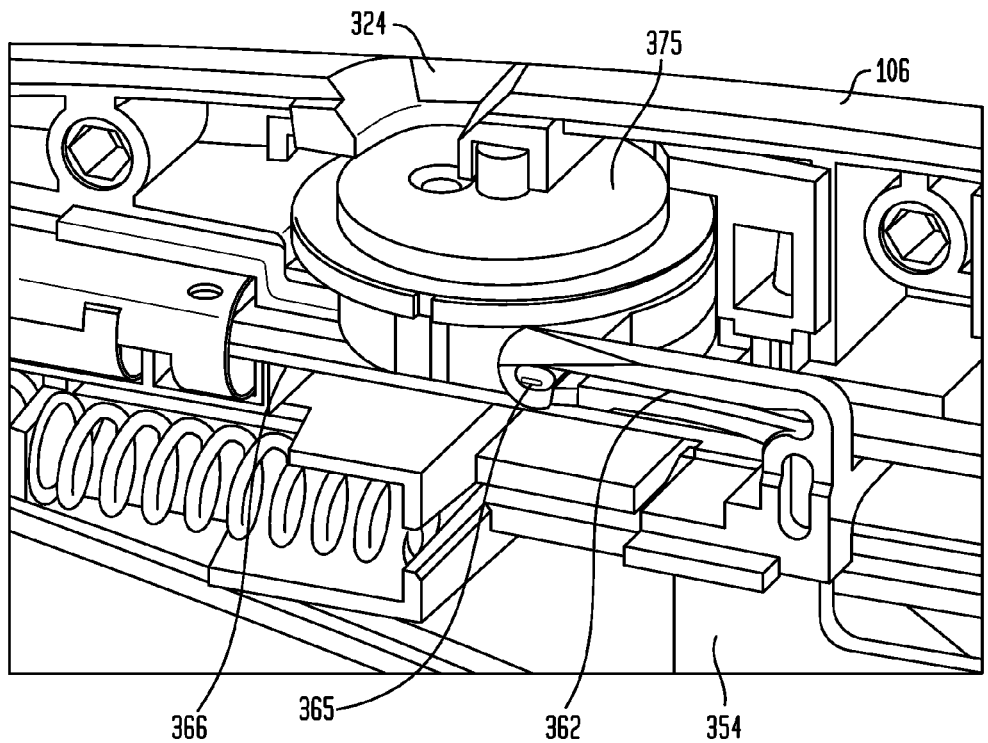
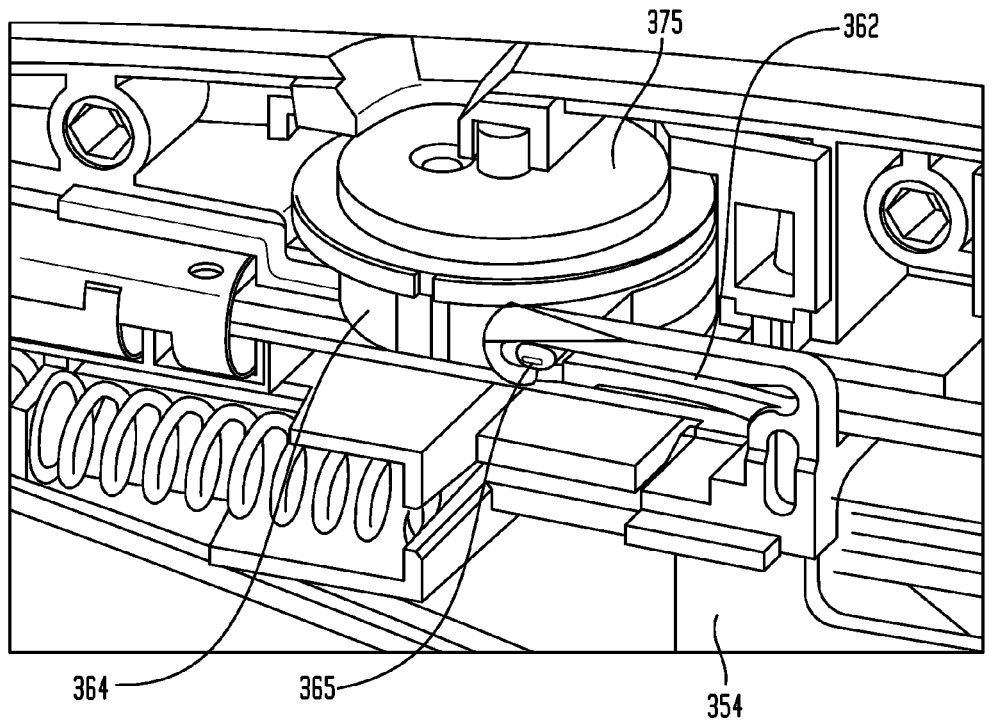

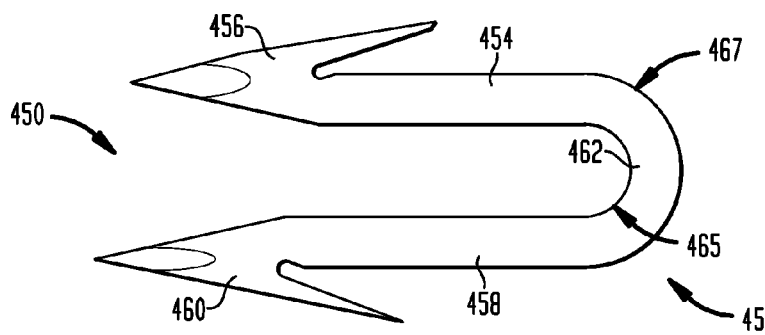 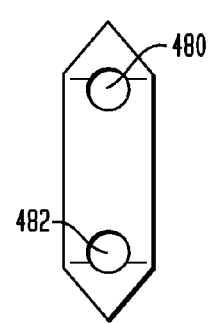
FIG. 16A / FIG. 16B
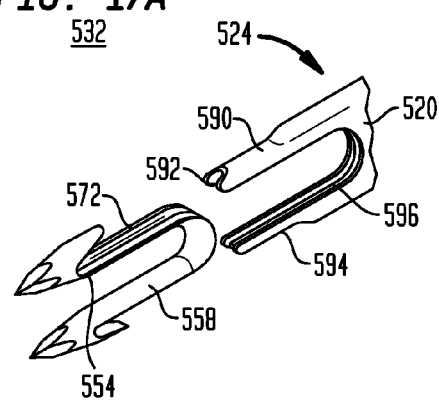 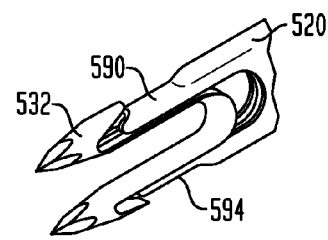
FIG. 17A / FIG. 17B
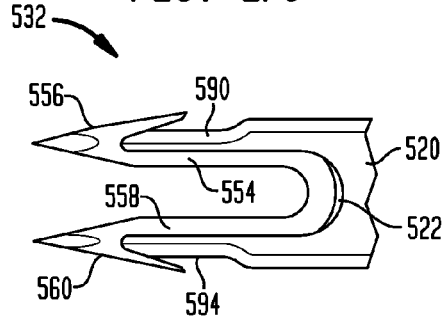
FIG. 17C

632

632

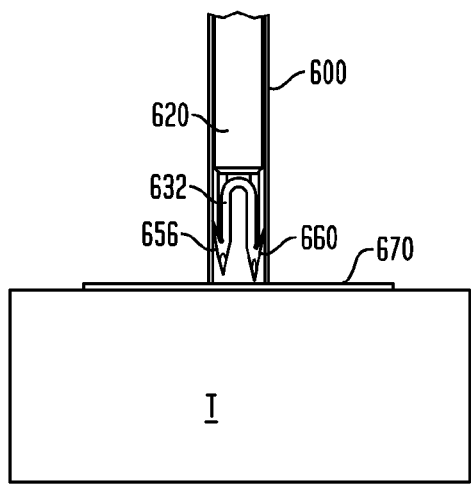
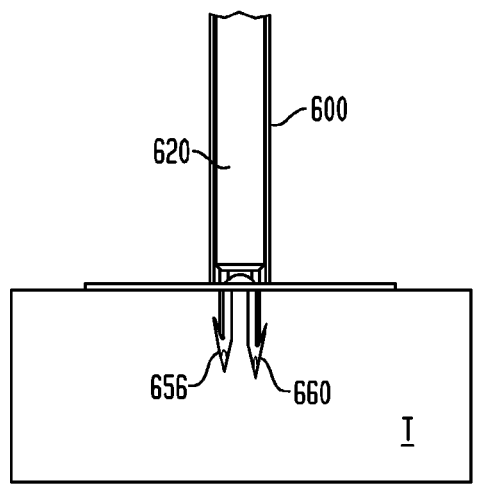
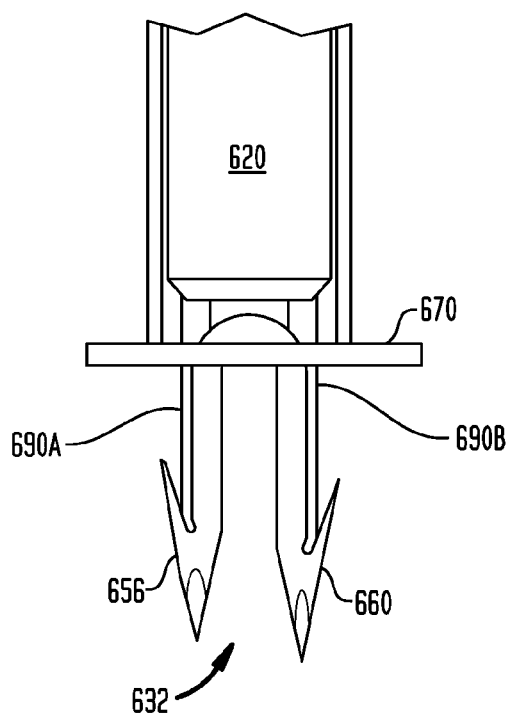
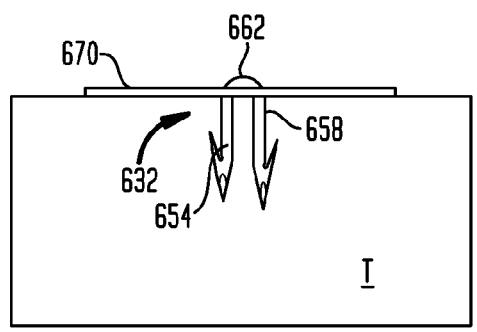

1132

SURGICAL FASTENERS, APPLICATOR INSTRUMENTS, AND METHODS FOR DEPLOYING SURGICAL FASTENERS

CROSS REFERENCE TO RELATED APPLICATIONS

The present application is related to the following commonly assigned U.S. patent applications filed on even date herewith: U.S. patent application Ser. No. 12/464,143, filed May 12, 2009 , U.S. patent application Ser. No 12/464,151, filed May 12, 2009 , and U.S. patent application Ser. No. 12/464,165, filed May 12, 2009. The disclosures of the above-identified patent applications are hereby incorporated by reference herein.

BACKGROUND OF THE INVENTION

1. Field of the Invention

The present invention generally relates to surgical fasteners, and more specifically relates to applicator instruments, systems and methods for deploying surgical fasteners.

2. Description of the Related Art

Hernia is a condition where a small loop of bowel or intestine protrudes through a weak place or defect within the abdominal muscle wall or groin of a patient. This condition commonly occurs in humans, particularly males. Hernias of this type may result from a congenital defect whereby the patient is born with this problem, or may be caused by straining or lifting heavy objects. Heavy lifting may be known to create a large amount of stress upon the abdominal wall and can cause a rupture or tearing at a weak point of the abdominal muscle to create the defect or opening. In any case, the patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution to the above-described problem may be surgery. During a surgical procedure, the defect is accessed and carefully examined, either through an open incision or endoscopically through an access port such as a trocar. In either case, careful examination is required due to the network of vessels and nerves which exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the open defect, and attaching the mesh patch to the abdominal wall or inguinal floor with conventional suture or with surgical fasteners. The mesh patch acts as a barrier and prevents expulsion of bowel through the defect. Suturing of the mesh patch to the inguinal floor can be well suited to open procedures but can be much more difficult and time consuming with endoscopic procedures. With the adoption of endoscopic surgery, endoscopic surgical instruments that apply surgical fasteners can be used. However, the tissue of the inguinal floor may offer special challenges to the surgeon when a needle or fastener is used to penetrate structures such as Cooper's ligament.

At present, there are a variety of surgical instruments and fasteners available for the surgeon to use in an endoscopic or open procedure to attach the mesh patch to the inguinal floor. One of the earliest types of endoscopic surgical instruments used is a surgical stapler. A plurality or stack of these unformed staples may be generally contained within a stapling cartridge in a serial fashion, and may be sequentially advanced or fed within the instrument by a spring mechanism. A secondary valving or feeding mechanism may be employed to separate the distal most staple from the stack, to hold the remainder of the spring loaded stack, and may be used to feed the distal most staples into the staple forming mechanism. Feeding mechanisms of this type are found in U.S. Pat. No. 5,470,010 to Rothfuss et al., and in U.S. Pat. No. 5,582,616, also to Rothfuss et al.

Another hernia mesh attachment instrument uses a helical wire fastener that resembles a small section of spring. Multiple helical wire fasteners may be stored serially within the 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. No. 5,582,616 to Bolduc et al., U.S. Pat. No. 5,810,882 to Bolduc et al., and in U.S. Pat. No. 5,830,221 to Stein et al.

Whereas the above surgical instruments may be used for hernia fastening applications, they use a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, but may require an additional secondary valving mechanism or protrusion to separate and feed one fastener from the stack.

Other surgical fasteners may be used for hernia mesh attachment but utilize either a reloadable single shot instrument or a rotary magazine that holds a small number of fasteners. These types of surgical fastening instruments can be found in U.S. Pat. Nos. 5,203,864 and 5,290,297, both to Edward Phillips. These instruments have not gained acceptance by the surgical community, possibly due to their single shot capabilities and the large size of the rotary magazine, which can restrict such an instrument to an open procedure.

Whereas all the above surgical instruments may be used for hernia fastening applications, they either use a spring mechanism to feed the plurality of fasteners through the surgical instrument, or a rotary magazine in lieu of a feeding mechanism. Other types of surgical fasteners may be available, such as surgical clips, and they can utilize feeding mechanisms that do not require the use of a spring to feed the clips distally. A reciprocating feeding mechanism is described in U.S. Pat. Nos. 5,601,573; 5,833,700; and 5,921,997 to Fogelberg et al. The Fogelberg et al. references teach a clip applier with a feeding mechanism that utilizes a reciprocating feed bar to feed a serial stack of clips. A feeder shoe may operably engage with and move with the distally moving feed bar and may slidingly engage with the proximally moving feed bar. Thus, the feeder shoe may index or push the stack of clips distally with the distally moving feed bar and remains stationary relative to the proximally moving feed bar. A valving mechanism may be also required to separate the distal-most clip from the stack and to hold the stack stationary as the distal most clip may be applied onto a vessel. Whereas the Fogelberg et al. references teach a reciprocating feeding mechanism with a single reciprocating member, they do not teach the use of the clip applier in the attachment of hernia mesh, nor do they teach the individual driving or feeding of each clip by a moving member.

Another fastener feeding mechanism that uses reciprocation is that disclosed in U.S. Pat. No. 4,325,376 to Klieman et al. A clip applier that stores a plurality of clips in a serial fashion within a clip magazine is disclosed. The clips are in a stack wherein the proximal most clip may be pushed or fed distally by a pawl that may be ratcheted or indexed distally by a reciprocating member or ratchet blade with each actuation of the instrument. As the pawl indexes distally, it can push the stack of clips distally. A secondary valving mechanism may be also described. Thus, the feeding mechanism of Klieman et al. teaches the use a single reciprocating member and pawl to push or feed the stack of clips distally, and may require a secondary valving mechanism to feed the distal most clip.

U.S. Pat. No. 3,740,994 to DeCarlo Jr. describes a novel reciprocating feeding mechanism that may index a plurality of staples or clips, and may ready them for discharge by reciprocating one of a pair of opposing leaf spring assemblies. The staples reside serially within a guide rail with a fixed leaf spring assembly extending into the plane of the guide rail. A reciprocating leaf spring assembly may opposedly extend inwardly towards the fixed leaf spring assembly. As the reciprocating leaf spring assembly moves distally, each of individual leaf springs of the assembly may engage a staple and move it distally. The distally moving staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent proximal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 to DiGiovanni et al. and U.S. Pat. No. 4,471,780 to Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Commonly assigned U.S. Patent Application Publication No. 2002/0068947, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the at least one surgical fasteners has a proximal end and a distal end. The device also has an actuator having at least two sequential positions. A first position for moving the moving member distally and piercing tissue, and a second position for moving the moving member proximally, thereby deploying the distal end of the fastener.

Tacks for fixing meshes used laparoscopically have generally been made of metal, such as stainless steel, nitinol, or titanium. The metal tacks were necessary to provide for sufficient holding strength, penetration of various prosthetic meshes, and for ease of manufacture. Until recently, there were no absorbable tacks available on the market, and surgeons could only use absorbable sutures in order to provide a fixation means that did not permanently stay in the body. However, using sutures is exceedingly difficult for laparoscopic procedure, and so they are generally not used unless the repair is done in an open fashion. With surgical trends leading to more minimally invasive techniques with minimum foreign body accumulation, an absorbable tack with minimum profile that can be applied laparoscopically is needed.

In spite of the above advances, there remains a need for further improvements. In particular, there remains a need for surgical fasteners having a minimum profile, surgical fasteners that may be applied laparoscopically, and surgical fasteners that are absorbable.

SUMMARY OF THE INVENTION

In one embodiment, the present invention discloses an applicator instrument and methods for consistently deploying surgical fasteners. In one embodiment, the applicator instrument is used to hold a prosthetic device such as surgical mesh in place over tissue. In one embodiment, the applicator instrument includes a mechanism for positioning a surgical fastener in line with a firing rod. The applicator instrument preferably includes a firing system that initially advances the firing rod toward the surgical fastener at a first speed. In one embodiment, energy may be stored in the firing system as the firing rod is advanced or piloted toward the surgical fastener. The firing system desirably engages the surgical fastener with the firing rod while maintaining the surgical fastener in a stationary position. The firing system preferably releases the stored energy to advance the firing rod at a second speed that is greater than the first speed to deploy the surgical fastener into tissue. In one embodiment, one surgical fastener is dispensed during one cycle of the firing system. A plurality of surgical fasteners may be dispensed for securing a prosthesis such as a surgical mesh to tissue.

In one embodiment, an applicator instrument for dispensing surgical fasteners preferably includes a housing, and an elongated shaft extending from the housing having a proximal end coupled with the housing and a distal end remote therefrom. The applicator instrument desirably includes a firing system for dispensing surgical fasteners from the distal end of the elongated shaft. The firing system preferably includes a firing rod disposed in the elongated shaft, and desirably has a firing cycle with a first stage for advancing the firing rod toward the distal end of the elongated shaft at a first rate of speed and a second stage for advancing the firing rod toward the distal end of the elongated shaft at a second rate of speed that is greater than the first rate of speed.

In one embodiment, a distal end of the firing rod includes an insertion fork. The applicator instrument is adapted to slowly pilot the insertion fork into a lead surgical fastener followed by quick firing of the surgical fastener through a prosthetic device and into tissue. Prior art devices rapidly advance a pushing element in one motion through a fastener in a hammer-like manner while continuing to drive the fastener into tissue, or slowly engage a fastener at the same rate for slowly driving the fastener into tissue. The first type of prior art device is limited in its ability to engage the fastener in a secure manner to assure the fastener's proper insertion into tissue. The first "hammer-like" prior art device may also damage the surgical fastener due to impact force or may require the use of a massive fastener adapted to withstand impact forces. The second type of prior art device does not advance the fastener fast enough to avoid tissue tenting and to enable proper tissue penetration. Both of these prior art approaches do not lend themselves to consistent and repeatable fastener penetration into tissue. In one embodiment, the present invention solves these limitations by slowly piloting an insertion fork into a lead surgical fastener, which assures proper engagement of the insertion fork with the surgical fastener. After proper engagement, the present invention also provides for quick firing of the surgical fastener through a prosthetic device and into tissue. As a result, each surgical fastener is preferably inserted the same way regardless of the speed of a user's trigger squeeze.

In one embodiment, the distal end of the firing rod is coupled with at least one of the surgical fasteners during the first stage of the firing cycle, and the distal end of the firing rod dispenses the at least one of the surgical fasteners from the distal end of the elongated shaft during the second stage of the firing cycle. The firing system may include an energy storing element such as a firing spring coupled with the firing rod, whereby the firing system is adapted to store energy in the firing spring before the second stage of the firing cycle and transfer the stored energy from the firing spring to the firing rod during the second stage of the firing cycle. In certain embodiments, the energy storing element may also include a pneumatic device, a hydraulic device and/or a compressed gas device.

In one embodiment, the applicator instrument includes an actuator movable between a first position and a second position for activating the firing system. The actuator may be a squeezable trigger that activates the firing system. In one embodiment, the firing spring is at least partially compressed prior to the first stage of the firing cycle, and the firing rod advances distally at a rate that is proportional to movement of the actuator during the first stage of the firing cycle. The firing spring is preferably compressible for storing energy therein as the actuator moves from the first position to the second position. The energy stored in the firing spring is released during the second stage of the firing cycle for rapidly driving the firing rod toward the distal end of the elongated shaft. Although many of the embodiments disclosed herein refer to a "firing spring", it is contemplated that other energy storing devices, such as those disclosed above may be used and still fall within the scope of the present invention.

In one embodiment, the firing system preferably includes a release latch that constrains the firing rod from moving toward the distal end of the elongated shaft after the first stage of the firing cycle and before the second stage of the firing cycle. At a preferred stage of the firing cycle, and preferably after energy is stored in the firing system, the release latch desirably releases the firing rod for moving distally.

In one embodiment, the applicator instrument may include an advancer coupled with the actuator and extending through the elongated shaft for advancing the surgical fasteners toward the distal end of the elongated shaft. The advancer is preferably adapted to move toward the distal end of the elongated shaft as the actuator moves from the first position to the second position. The advancer is preferably adapted to move toward the proximal end of the shaft as the actuator moves from the second position to the first position. The advancer desirably includes a plurality of advancer tabs projecting toward a distal end of the advancer, whereby each advancer tab is adapted to engage one of the surgical fasteners for urging the surgical fasteners toward the distal end of the elongated shaft.

In one embodiment, the surgical fasteners are disposed within the elongated shaft for being urged toward the distal end of the elongated shaft by the advancer. In one embodiment, a most distal one of the surgical fasteners is engageable by the staging assembly for aligning the most distal one of the surgical fasteners with the distal end of the firing rod. In one embodiment, the distal end of the firing rod includes an insertion fork having spaced tines that are adapted to engage the most distal one of the surgical fasteners.

In one embodiment, a surgical fastener includes a first leg having a distal end with a first insertion tip, a proximal end, and a first insertion tool seating surface located adjacent the first insertion tip. The surgical fastener preferably includes a second leg having a distal end with a second insertion tip, a proximal end, and a second insertion tool seating surface located adjacent the second insertion tip. The surgical fastener also desirably includes a bridge connecting the proximal ends of the first and second legs for forming a closed proximal end of the surgical fastener. In one embodiment, tines of an insertion fork are preferably seatable against the first and second insertion tool seating surfaces of the surgical fastener for applying an insertion force upon the surgical fastener at a location that is closer to the distal end of the surgical fastener than the proximal end of the surgical fastener.

In one embodiment, an applicator instrument may include a lockout system coupled with the firing system for preventing operation of the firing system after all of the surgical fasteners have been dispensed. In one embodiment, the lockout system locks an actuator or trigger in a closed position after all of the surgical fasteners have been dispensed.

In one embodiment, an applicator instrument for dispensing surgical fasteners includes a housing having a handle section and a trigger, and an elongated shaft for dispensing the surgical fasteners. The elongated shaft includes a proximal end coupled with the housing and a distal end remote therefrom. The elongated shaft may include a surgical fastener delivery conduit extending therethrough for delivering or dispensing the surgical fasteners from the distal end of the elongated shaft. The applicator instrument preferably includes a firing system actuatable by the trigger, whereby the firing system includes a firing rod and an energy storing assembly coupled with the firing rod. In one embodiment, the firing system desirably has a firing cycle including a first stage for moving the firing rod toward the distal end of the elongated shaft at a first speed and a second stage for transferring energy from the energy storing assembly to the firing rod for driving the firing rod toward the distal end of the elongated shaft at a second speed that is greater than the first speed. In one embodiment, energy may be stored in the energy storing assembly during the initial piloting stage when the firing rod moves forward at the first speed.

In one embodiment, the applicator instrument may include a staging assembly disposed within the elongated shaft for aligning the surgical fasteners with a distal end of the firing rod. The surgical fasteners are preferably advanced through an elongated conduit in the elongated shaft and toward the distal end of the elongated shaft. The applicator instrument may include an advancer coupled with the firing system for incrementally advancing the surgical fasteners toward the distal end of the elongated shaft each time the trigger is squeezed. In one embodiment, the firing rod preferably moves distally as the trigger is squeezed from an open position to a closed position, and the firing rod moves proximally as the trigger returns from the closed position to the open position.

In one embodiment, a method of dispensing surgical fasteners includes providing an applicator instrument having a housing, an elongated shaft projecting from the housing, and a firing system including a firing rod for dispensing surgical fasteners from a distal end of the elongated shaft. The method preferably includes aligning a first surgical fastener with a distal end of the firing rod, advancing the distal end of the firing rod toward the first surgical fastener at a first speed for engaging the surgical fastener, and after the firing rod advancing step and while constraining the firing rod from moving toward the distal end of the elongated shaft, storing energy in the firing system. The method desirably includes releasing the firing rod for distal movement and transferring the stored energy to the firing rod for driving the firing rod distally at a second speed that is greater than the first speed so as to dispense the first or lead surgical fastener from the distal end of the elongated shaft.

In one embodiment, the firing system desirably includes a compressible firing spring coupled with the firing rod, and an actuator coupled with the firing spring for selectively compressing the firing spring for storing energy in the firing system. In one embodiment, the energy for advancing the firing rod is stored in a spring. In one embodiment, the spring is a firing spring that is preferably pre-loaded or pre-compressed prior to actuation of the applicator instrument.

In one embodiment, the applicator instrument includes a lockout mechanism to prevent operation of the applicator instrument when no more surgical fasteners are available (e.g. all of the surgical fasteners have been dispensed). In one embodiment, the lockout mechanism preferably locks the trigger in a closed position when the device is empty. The lockout mechanism may also include a mechanical or electronic counter that displays how many surgical fasteners have been dispensed and/or how many surgical fasteners remain available.

In one embodiment, the distal end of the applicator instrument, such as the distal end of the elongated shaft, includes one or more markings for orientation. The distal end of the elongated shaft may also include one or more features provided on the distal tip to assist with device orientation and/or to capture one or more mesh strands. In one embodiment, the applicator instrument includes one or more protuberances to capture one or more strands of mesh.

In one embodiment, a surgical fastener includes a first leg having a distal end, a proximal end and a first insertion tip at the distal end of the first leg. The surgical fastener preferably includes a second leg having a distal end, a proximal end, and a second insertion tip at the distal end of the second leg. A bridge desirably connects the proximal ends of the first and second legs for forming a closed end of the surgical fastener. The first insertion tip preferably includes a first insertion tool seating surface and the second insertion tip preferably includes a second insertion tool seating surface.

In one embodiment, the first and second legs extend along respective longitudinal axes, and the first and second insertion tips are skewed or angulated outwardly relative to the respective longitudinal axes of the first and second legs. As a result, in one embodiment, the spacing between the insertion tips is greater than the spacing between the first and second legs, which may enhance the capture of strands or fibers between the legs. In one embodiment, at least one of the first and second insertion tips includes a blunt distal piercing point. In one embodiment, both of the first and second insertion tips include blunt distal piercing points.

In one embodiment, the first insertion tip includes a proximal end with the first insertion tool seating surface, and the second insertion tip includes a proximal end including the second insertion tool seating surface. In one embodiment, the first insertion tool seating surface is closer to the distal end of the first leg than the proximal end of the first leg, and the second insertion tool seating surface is closer to the distal end of the second leg than the proximal end of the second leg. The first and second insertion tool seating surfaces preferably face toward the proximal ends of the respective first and second legs and are adapted to be engaged by the distal end of an insertion tool, such as the distal ends of tines or an insertion fork.

In one embodiment, the first insertion tool seating surface includes an opening facing toward the proximal end of the first leg, and the second insertion tool seating surface includes a second opening facing toward the proximal end of the second leg. The openings in the insertion tool seating surfaces may be blind openings that are closed at one end (e.g. at the distal end). In one embodiment, the first insertion tool seating surface includes a first aperture that extends completely through the first insertion tip, and the second insertion tool seating surface includes a second aperture that extends completely through the second insertion tip.

In one embodiment, the first leg of a surgical fastener preferably includes a first alignment guide extending between the proximal end of the first leg and the first insertion tool seating surface, and the second leg preferably includes a second alignment guide extending between the proximal end of the second leg and the second insertion tool seating surface. The first alignment guide on the first leg is preferably in substantial alignment with the first insertion tool seating surface, and the second alignment guide on the second leg is preferably in substantial alignment with the second insertion tool seating surface. The first and second alignment guides may include ribs extending between the distal and proximal ends of the legs, grooves extending between the distal and proximal ends of the legs, or a combination of ribs and grooves.

In one embodiment, the first and second insertion tips have distal ends that are staggered from one another, which may reduce the amount of force required to anchor the surgical fastener in tissue. In one embodiment, the bridge adjacent the proximal end of the surgical fastener defines a third insertion tool seating surface engageable by a surface on an insertion tool.

In one embodiment, the first leg of a surgical fastener includes a first barb projecting toward the proximal end of the first leg, and the second leg of the surgical fastener includes a second barb projecting toward the proximal end of the second leg, whereby the first and second barbs are staggered from one another. In one embodiment, the first and second barbs on the respective first and second legs project outwardly away from one another. In another embodiment, the first and second barbs on the respective first and second legs project inwardly toward one another.

In one embodiment, a surgical fastener for anchoring prosthetic devices to tissue includes a first leg having a distal end, a proximal end, a first alignment guide extending between the distal and proximal ends of the first leg, and a first insertion tip at the distal end of the first leg. The surgical fastener desirably includes a second leg having a distal end, a proximal end, a second alignment guide extending between the distal and proximal ends of the second leg, and a second insertion tip at the distal end of the second leg. The surgical fastener preferably includes a bridge connecting the proximal ends of the first and second legs for forming a closed end of the surgical fastener.

In one embodiment, the first insertion tip has a proximal end with a first insertion tool seating surface and the second insertion tip has a proximal end with a second insertion tool seating surface. The first and second insertion tool seating surfaces may include convex surfaces facing toward the proximal ends of the first and second legs, concave surfaces facing toward the proximal ends of the first and second legs, openings facing toward the proximal ends of the first and second legs, blind vias facing toward the proximal ends of the first and second legs, and/or apertures extending through the first and second insertion tips.

In one embodiment, the first and second alignment guides are selected from the group of alignment guides including ribs extending between the distal and proximal ends of the legs, and grooves extending between the distal and proximal ends of the legs. The first and second alignment guides are substantially aligned with the respective first and second insertion tool seating surfaces. In one embodiment, the first and second seating surfaces are desirably closer to the distal end of the surgical fastener than the proximal end of the surgical fastener.

In one embodiment, an applicator instrument for dispensing surgical fasteners includes a housing, and an elongated shaft extending from the housing, the elongated shaft having a proximal end, a distal end, and a longitudinal axis extending between the proximal and distal ends. The applicator instrument desirably includes a firing rod disposed inside the elongated shaft and that is moveable within a first plane between a retracted position and an extended position. The elongated shaft preferably includes an advancer disposed inside the elongated shaft that is moveable within a second plane between a retracted position and an extended position. The applicator instrument preferably includes a staging assembly located adjacent the distal end of the elongated shaft that is adapted to align surgical fasteners with a distal end of the firing rod. The staging assembly is preferably held below the second plane by the advancer when the advancer is in the extended position, and the staging assembly is preferably adapted to move into at least partial alignment with the distal end of the firing rod when the advancer moves toward or is in the retracted position.

The applicator instrument preferably includes a plurality of surgical fasteners disposed within the elongated shaft, whereby the advancer is adapted to move the surgical fasteners one position toward the distal end of the elongated shaft each time the advancer moves from the retracted position to the extended position. In one embodiment, the plurality of surgical fasteners desirably include a lead surgical fastener located adjacent the distal end of the elongated shaft and a series of trailing surgical fasteners located between the lead surgical fastener and the proximal end of the elongated shaft.

In one embodiment, the advancer includes a plurality of advancer tabs whereby each of the advancer tabs is preferably adapted to engage one of the surgical fasteners for urging the surgical fasteners toward the distal end of the elongated shaft as the advancer moves from the retracted position to the extended position. In one embodiment, the advancer tabs project toward the distal end of the elongated shaft. In one embodiment, the advancer is moveable into the extending position for moving the lead surgical fastener into contact with the staging assembly.

In one embodiment, a floor of the elongated shaft includes a plurality of anti-backup tabs, whereby the anti-backup tabs are adapted to prevent the surgical fasteners in the elongated shaft from moving toward the proximal end of the elongated shaft. In one embodiment, the anti-backup tabs project toward the distal end of the elongated shaft.

In one embodiment, the advancer urges the lead surgical fastener into contact with the staging assembly, and the staging assembly is adapted to lift the lead surgical fastener into substantial alignment with the distal end of the firing rod as the advancer returns to the retracted position.

In one embodiment, the elongated shaft includes at least one guide surface adapted to engage and/or contact the firing rod for guiding distal and proximal movement of the firing rod. In one embodiment, the at least one guide surface includes a pair of opposing guide flanges adapted to engage opposites sides of the firing rod for guiding distal and proximal movement of the firing rod.

In one embodiment, the distal end of the firing rod includes an insertion tool, such as an insertion fork, having a first tine with a distal end adapted to engage the first insertion tool seating surface, and a second tine having a distal end adapted to engage the second insertion tool seating surface. In one embodiment, the bridge of the surgical fastener has a proximal face defining a third insertion tool seating surface, and the insertion tool includes a distal surface extending between the proximal ends of the first and second tines adapted to engage the third insertion tool seating surface.

In one embodiment, an applicator instrument for dispensing surgical fasteners includes a housing, an elongated shaft extending from the housing, the elongated shaft including a proximal end and a distal end remote therefrom, and a plurality of surgical fasteners disposed within the elongated shaft for being dispensed from the distal end of the elongated shaft. The applicator instrument preferably includes an advancer disposed inside the elongated shaft that is moveable between the proximal and distal ends of the elongated shaft, whereby the advancer is adapted to shift the surgical fasteners one position closer to the distal end of the elongated shaft each time the advancer moves distally. The applicator instrument preferably includes a firing rod disposed inside the elongated shaft and overlying the advancer, the firing rod being moveable between the proximal and distal ends of the elongated shaft. The applicator instrument desirably includes a staging assembly located adjacent the distal end of the elongated shaft that is adapted to receive a leading one of the surgical fasteners from the advancer as the advancer moves distally and to shift the received leading surgical fastener into substantial alignment with a distal end of the firing rod when the advancer moves proximally.

In one embodiment, the distal end of the firing rod is adapted to move distally at a first rate of speed for engaging the leading surgical fastener, and then to move distally at a second rate of speed that is faster than the first rate of speed for dispensing the leading surgical fastener from the distal end of the elongated shaft.

In one embodiment, the first leg of the surgical fastener includes a first alignment guide extending between the proximal end of the first leg and the first insertion tool seating surface, and the second leg of the surgical fastener includes a second alignment guide extending between the proximal end of the second leg and the second insertion tool seating surface. The first alignment guide on the first leg is preferably in substantial alignment with the first insertion tool seating surface and the second alignment guide on the second leg is preferably in substantial alignment with the second insertion tool seating surface. In one embodiment, the first alignment guide includes a first rib extending between the distal and proximal ends of the first leg, and the second alignment guide includes a second rib extending between the distal and proximal ends of the second leg, whereby the first and second tines at the distal end of the firing rod have opposing inner surfaces with opposing grooves adapted to engage the first and second ribs on the respective first and second legs for engaging the surgical fastener with the insertion tool.

In one embodiment, a method of dispensing a surgical fastener includes providing an applicator instrument having a housing and an elongated shaft extending from the housing, the elongated shaft including a proximal end and a distal end remote therefrom, and providing surgical fasteners in the elongated shaft for being dispensed one at a time from the distal end of the elongated shaft. The method preferably includes advancing the surgical fasteners within a first plane toward the distal end of the elongated shaft. After advancing a leading one of the surgical fasteners to a location adjacent the distal end of the elongated shaft, the leading surgical fastener is preferably shifted from the first plane into a second plane in which the leading surgical fastener is substantially aligned with a distal end of a firing rod. The firing rod is then desirably moved distally for engaging the leading surgical fastener with the firing rod and dispensing the leading surgical fastener from the distal end of the elongated shaft.

In one embodiment, the method includes loading the surgical fasteners in the elongated shaft. In one embodiment, the step of moving the firing rod distally includes a first distal movement stage during which the firing rod moves distally at a first rate of speed for engaging the leading surgical fastener, and a second distal movement stage that follows the first distal movement stage during which the firing rod moves distally at a second rate of speed for dispensing the leading surgical fastener from the distal end of the elongated shaft, whereby the second rate of speed is greater than the first rate of speed.

In one embodiment, after the advancing step, and while constraining the firing rod from moving toward the distal end of the elongated shaft, energy is stored in the firing system. The firing rod may later be unconstrained or released so that it is able to move in the distal direction and the stored energy may be transferred to the firing rod for driving the firing rod distally at the second speed that is greater than the first speed for dispensing the first surgical fastener from the distal end of the elongated shaft.

In one embodiment, the firing system includes an energy storing element such as a compressible firing spring coupled with the firing rod, and an actuator coupled with the firing spring for selectively compressing the firing spring so as to store energy in the firing system.

In one embodiment, a method of affixing a prosthesis to tissue includes providing an applicator instrument for dispensing surgical fasteners having a housing, an elongated shaft extending from the housing, the elongated shaft having a proximal end coupled with the housing and a distal end remote therefrom, and a firing system for dispensing surgical fasteners from the distal end of the elongated shaft. The firing system preferably includes a firing rod disposed in the elongated shaft, the firing system having a firing cycle with a first stage for advancing the firing rod toward the distal end of the elongated shaft at a first rate of speed and a second stage for advancing the firing rod toward the distal end of the elongated shaft at a second rate of speed that is greater than the first rate of speed. The method preferably includes positioning a prosthesis, such as a surgical mesh, over tissue, and operating the applicator instrument for dispensing at least one of the surgical fasteners from the distal end of the elongated shaft for affixing the prosthesis to the tissue. In one embodiment, a plurality of surgical fasteners may be dispensed for affixing the prosthesis to the tissue.

In one embodiment, a firing system for an applicator instrument adapted to dispense surgical fasteners includes a housing, an elongated shaft extending from the housing, a firing rod disposed within the elongated shaft, a firing rod release engageable with the firing rod for preventing distal movement of the firing rod during at least one stage of a firing cycle, a trigger mounted to the housing, and a firing spring having a first end connected with the firing rod and a second end adapted for being sequentially coupled and decoupled from the trigger during the firing cycle. In one embodiment, the firing cycle desirably includes an initial stage in which the trigger is open and decoupled from the firing spring and the firing spring is at least partially compressed, and a piloting stage during which the firing rod release is disengaged from the firing rod for enabling distal movement of the firing rod. The trigger is preferably compressible a first distance for coupling the trigger with the firing spring for moving the at least partially compressed firing spring distally, which, in turn, moves the firing rod distally at a first rate of speed that is proportional to the movement of the trigger. In one embodiment, an energy storing element such as a pneumatic or hydraulic device may be used in place of or in combination with the firing spring.

In one embodiment, the firing cycle includes, after the piloting stage, an energy storing stage in which the firing rod release engages the firing rod for preventing distal movement of the firing rod, and the trigger is further moveable a second distance for further compressing and storing energy in the firing spring. The firing cycle preferably includes a firing stage in which the firing rod release disengages from the firing rod so that the firing rod is free to move toward the distal end of the elongated shaft and the firing spring transfers the energy stored therein to the firing rod for rapidly advancing the firing rod toward the distal end of the elongated shaft at a second rate of speed that is greater than both the first rate of speed and the movement of the trigger.

In one embodiment, the firing cycle includes a decoupling stage during which the trigger is further compressible a third distance for decoupling the trigger from the firing spring whereupon the firing rod is free to move toward the proximal end of the elongated shaft.

In one embodiment, the firing system includes an advancer disposed within the elongated shaft and that is moveable in proximal and distal directions along the elongated shaft. The firing cycle preferably includes, after the firing stage, a surgical fastener advancing stage during which the trigger is further compressible a fourth distance for moving the advancer toward the distal end of the elongated shaft so as to move the surgical fasteners toward the distal end of the elongated shaft.

In one embodiment, the firing cycle preferably includes, after the surgical fastener advancing stage, a retraction stage during which the trigger moves from a compressed position to the open position of the initial stage for moving the advancer in a proximal direction.

In one embodiment, the firing system preferably includes a spring block disposed within the housing and engageable with a proximal end of the firing spring. The spring block is preferably adapted to move proximally and distally along the longitudinal axis defined by the elongated shaft. In one embodiment, during the energy storing stage, the trigger is coupled with the spring block for moving the spring block distally, which, in turn, further compresses the firing spring.

In one embodiment, the firing system includes a primary latch coupled with the trigger. The primary latch is preferably adapted to couple the trigger with the spring block during the piloting, energy storing, and firing stages, and decouple the trigger from the spring block during the decoupling, surgical fastener advancing, and retraction stages. In one embodiment, at the beginning of the firing stage, the spring block contacts the firing rod release for disengaging the firing rod release from the firing rod so that the firing rod may move distally.

In one embodiment, a firing system for a surgical fastener applicator instrument includes a housing and an elongated shaft extending from the housing. The firing system desirably includes a firing rod disposed within the elongated shaft and being moveable proximally and distally along a longitudinal axis, a firing spring block disposed within the housing and being adapted to move in proximal and distal directions along the longitudinal axis, and a firing spring having a distal end connected with the firing rod and a proximal end engageable with the firing spring block. The firing system preferably includes a trigger mounted to the housing for driving the firing system, whereby the trigger includes a primary latch for sequentially coupling and decoupling the trigger from the firing spring block during a firing cycle.

In one embodiment, the firing cycle preferably includes an initial stage in which the trigger is open, the trigger is decoupled from the firing spring block, and the firing spring is at least partially compressed. The firing system preferably includes a piloting stage in which the firing rod is free to move distally, and the trigger is compressible a first distance for coupling the trigger with the firing spring block so as to move the at least partially compressed firing spring distally, which, in turn, moves the firing rod distally at a first rate of speed that is proportional to the movement of the trigger. In one embodiment, the compression level of the firing spring remains unchanged during the piloting stage. In one embodiment, the firing spring may be compressed during the piloting stage.

In one embodiment, the firing cycle includes, after the piloting stage, an energy storing stage in which the trigger is further compressible a second distance for further compressing and/or storing energy in the firing spring while the firing rod release engages the firing rod for preventing distal movement of the firing rod.

The firing cycle preferably includes, after the energy storing stage, a firing stage in which the firing rod release disengages from the firing rod so that the firing rod is free to move toward the distal end of the elongated shaft and the firing spring transfers the energy stored therein to the firing rod for rapidly advancing the firing rod toward the distal end of the elongated shaft at a second rate of speed that is greater than the first rate of speed.

The firing cycle preferably includes, after the firing stage, a decoupling stage during which the trigger is further compressible a third distance for decoupling the trigger from the firing spring and the firing rod so that said firing rod may move proximally.

In one embodiment, the firing system includes an advancer disposed within the elongated shaft. The advancer is preferably moveable between the proximal and distal ends of the elongated shaft for moving surgical fasteners toward the distal end of the elongated shaft. The firing cycle may include, after the firing stage, a surgical fastener advancing stage during which the trigger is further compressible a fourth distance for moving the advancer toward the distal end of the elongated shaft, which, in turn, moves the surgical fasteners toward the distal end of the elongated shaft.

In one embodiment, the firing system preferably includes a spring block disposed within the housing. The spring block is preferably adapted to move proximally and distally along the longitudinal axis. The spring block preferably engages the firing spring, and during the energy storing stage, the trigger is coupled with the spring block for moving the spring block distally, which, in turn, compresses the firing spring. The firing system may also include a primary latch coupled with the trigger. The primary latch is preferably adapted to couple the trigger with the spring block during the piloting, energy storing, and firing stages, and decouple the trigger from the spring block during the decoupling, surgical fastener advancing, and retraction stages.

In one embodiment, a method of dispensing surgical fasteners from an applicator instrument includes providing a housing, an elongated shaft extending from the housing, a firing rod disposed within the elongated shaft that is moveable proximally and distally for dispensing surgical fasteners from the distal end of the elongated shaft, a trigger for operating the applicator instrument, and an energy storing element disposed between the trigger and the firing rod. The method preferably includes compressing the trigger for piloting the firing rod toward the distal end of the elongated shaft at a first rate of speed, and after piloting the firing rod, preventing the firing rod from moving distally while further compressing the trigger for storing energy in the energy storing element. The method preferably includes releasing the firing rod for distal movement, and transferring the energy stored in the energy storing element to the firing rod for moving the firing rod toward the distal end of the elongated shaft at a second rate of speed that is greater than the first rate of speed. In one embodiment, during the piloting stage, the firing rod moves distally at a first rate of speed that is proportional to the movement of the trigger.

In one embodiment, the energy storing element is a firing spring disposed between the trigger and the firing rod. In one embodiment, the firing spring is at least partially compressed before piloting the firing rod toward the distal end of the elongated shaft and the firing spring has a compression level that does not change during the piloting step. As noted herein, the energy storing element may also include a pneumatic device, a hydraulic device, a compressed gas device, or combinations thereof.

In one embodiment, the method includes providing a plurality of surgical fasteners within the elongated shaft, and providing an advancer disposed within the elongated shaft. The advancer is preferably coupled with the trigger and is adapted to move toward the distal end of the elongated shaft when the trigger is compressed and move toward the proximal end of the elongated shaft when the trigger is opened. The method preferably includes compressing the trigger for moving the advancer toward the distal end of the elongated shaft, whereby the distally moving advancer shifts each of the surgical fasteners one position closer to the distal end of the elongated shaft. In one embodiment, the trigger may not return to the open position until it is completely squeezed to the closed position.

The applicator instrument may be made in various lengths and diameters. Shorter lengths may be more suitable for open surgical procedures. In one embodiment, the diameter of the shaft of the applicator instrument is preferably between about 3-10 mm, and more preferably between about 3-5 mm. In one embodiment, the applicator instrument includes more than one surgical fastener and may be pre-loaded with a plurality of fasteners such as 10, 25, 100 or more surgical fasteners. In one embodiment, the applicator instrument is pre-loaded with 10 surgical fasteners for open procedures. In one embodiment, the applicator instrument is pre-loaded with 30 surgical fasteners for standard laparoscopic procedures. In one embodiment, the surgical fasteners may be housed in cartridges for easy loading and/or re-loading. In certain embodiments, the applicator instrument may include a stay suture device as part of the handle, or a device/handle that dispenses a skin adhesive such as the tissue adhesive sold under the trademark Dermabond™ for use for trocar wound closure.

In one embodiment, a surgical fastener preferably has a very small profile, may be semi-rigid, and may be fully resorbable. The resorbable nature of the surgical fastener preferably decreases chronic pain caused by permanent fixation. In addition, the low profile of the surgical fastener reduces adhesions of the viscera. As is well known to those skilled in the art, it is very common to see excessive adhesions caused by permanent tackers during re-ops.

In one embodiment, a surgical fastener provides two points of fixation with a connecting back span extending between the two points of fixation so as to spread the tissue holding forces over a greater area. The span between the two points of fixation makes it possible to span the tack across the edge of a mesh, which minimizes exposure of tissue to mesh ends that may be the source of tissue irritation.

In one embodiment, an applicator instrument deploys one or more soft tissue surgical fasteners. The surgical fasteners provide low profile soft tissue fixation of prosthetic materials onto the human body. In one embodiment, the applicator instrument provides for tension-free laparoscopic hernia repair using mesh. In one embodiment, a prosthetic mesh is placed over an abdominal defect and attached to tissue with either permanent or resorbable surgical fasteners. In one embodiment, the surgical fasteners are made of relatively soft materials such as plastic or absorbable polymers.

The present invention provides a number of benefits. In one embodiment, male features on a surgical fastener mate with female features on an inserter device, which reduces the cost for molding the surgical fasteners. In one embodiment, pins or tines on an insertion device provide rigidity during insertion of the surgical fastener and leaves less absorbable mass in tissue as compared with tack systems and methods that do not use inserter pins or tines for stiffening.

In one embodiment, the surgical fasteners have rounded proximal ends. Specifically, each surgical fastener has a connecting bridge or back span at the proximal end of the surgical fastener that is rounded and results in a very low profile after insertion into tissue. The low profile design and small diameter of the surgical fastener results in the surgical fastener having the appearance of a suture stitch once the surgical fastener is implanted. The lower profile also preferably reduces the possibility of forming adhesions in the body.

In one embodiment, surgical fasteners have insertion pin holes or recesses formed in the proximal portion of each insertion tip of the surgical fasteners. The insertion pin holes or recesses are preferably located directly over the center of each insertion tip. As a result, the insertion pin holes or recesses are substantially aligned with the insertion tip to avoid tip bending and to direct forces for insertion directly behind each of the penetrating insertion tips.

In prior art fasteners having a single head, the single head may fall through the large pores of the prosthetic mesh. In one embodiment, surgical fasteners of the present invention have a connecting back span or bridge between two insertion tips. The connecting back span or bridge makes the surgical fastener more compatible for use with large pore surgical prosthetic meshes.

In one embodiment, surgical fasteners have blind holes that are filled by metal inserters, probes, or tines during application. The metal inserters preferably provide rigidity to the surgical fastener during insertion, allowing the surgical fastener itself to be made of a softer material, such as an absorbable polymer. In another embodiment, rigid inserters, probes or tines support the tips and/or legs of the surgical fastener during anchoring into tissue.

In one embodiment, surgical fasteners have lead-in channels that are aligned with blind holes or tool seating surfaces. The lead-in channels are axially open on at least one side, which enables less material to be used for forming the surgical fasteners, and which provides a space for tissue in-growth to maximize fixation strength.

In one embodiment, surgical fasteners have staggered tips, which preferably reduce the necessary penetration force by staggering the peak forces encountered during insertion. In one embodiment, surgical fasteners have staggered barbs improve anchoring in tissue by requiring greater pull out forces.

In one embodiment, surgical fasteners have barbs set out of plane from each other, which increase the force necessary for pull out of the surgical fasteners. In one embodiment, surgical fasteners have insertion tips with through openings extending therethrough. The through openings are preferably adapted to receive one or more needles for needle-assisted insertion.

In one embodiment, surgical fasteners have one or more barbs with "living hinge" features. The living hinges enable the barbs to collapse easily during insertion but flare outwardly during attempts to remove the surgical fasteners.

In one embodiment, the pointed insertion tips of the surgical fasteners are cut or have defined chisel points, which enable the insertion tips to cut during insertion, thereby improving the ability of the surgical fasteners to penetrate difficult materials such as GORE® dual mesh. Insertion tips having compound cut or chiseled angles may also be used to allow for stronger, yet shorter tip designs.

In one embodiment, surgical fasteners may have conical-shaped insertion tips that create a puncture rather than a cut, thereby improving holding force. Although the present invention is not limited by any particular theory of operation, it is believed that conical-shaped insertion tips create only a single point of stress concentration, whereby the section of the surgical fastener that follows must expand the hole radially. It is believed that this may make it harder for the rest of the surgical fastener to make it through the hole, but may potentially increase retention forces by making a tighter hole.

In one embodiment, a surgical fastener includes a pair of spaced insertion points having internally facing barbs. The internally facing barbs desirably protect the barbs from external forces, and make the surgical fasteners easier to multi-feed without damaging the barbs. These embodiments may have straight side walls and back spans that enable the surgical fasteners to remain properly aligned within a laparoscopic tube.

In one embodiment, surgical fasteners may incorporate active agents such anti-microbials and anti-adhesion materials. In one embodiment, surgical fasteners may incorporate radio-opacity to enable the surgical fasteners to be visible on x-ray imaging machines.

In one embodiment, ribs are formed on the outside of each leg of the surgical fastener, and an insertion fork has a mating channel that straddles each of the ribs. The ends of each fork tine bottom out in recesses or seating surfaces formed in the insertion tips of the surgical fastener. This above design transfers the complexity of manufacturing recesses from the legs of the surgical fastener to the tines of the insertion tool. This feature is especially important because the applicator instrument will preferably dispense multiple surgical fasteners (as opposed to just one insertion fork).

In one embodiment, an insertion tool includes a bridge that extends between proximal ends of fork tines. The shape of the bridge on the insertion tool may substantially conform to the proximal face of the bridge at the proximal end of the surgical fastener. In one embodiment, the insertion fork is designed so that the bridge element of the insertion fork comes into contact with the proximal end of the surgical fasteners at the time, or just prior to when, the distal ends of each fork bottoms out or engages the seating surfaces formed in the insertion tips of the surgical fastener. In one embodiment, the bridge of the insertion fork may include a softer (with respect to the durometer of the rest of the insertion fork) elastomeric material to reduce the required dimensional precision necessary to assure contact of the bridge and distal fork ends with the surgical fastener at about the same time. This configuration preferably enables the driving force behind the surgical fastener to be distributed along a greater surface area of the surgical fastener so as to reduce the pressure generated between the insertion tool and the surgical fastener.

These and other preferred embodiments of the invention will be described in more detail below.

BRIEF DESCRIPTION OF THE DRAWINGS

FIG. 8C-1 shows an enlarged view of the insertion tip shown in FIG. 8C.

FIGS. 11A-1 through 11N-1 show a cross-sectional side view of a distal end of an applicator instrument during the stages of a firing cycle shown in respective FIGS. 11A-11N.

FIGS. 12A-12E show a method of using an applicator instrument for dispensing surgical fasteners for securing a prosthetic device to tissue, in accordance with one embodiment of the present invention.

FIG. 13A shows a perspective view of a lockout system for an applicator instrument, in accordance with one embodiment of the present invention.

FIG. 13B shows a side view of the lockout system shown in FIG. 13A.

FIGS. 16A-16B show a surgical fastener, in accordance with one embodiment of the present invention.

FIGS. 17A-17C show a method of dispensing a surgical fastener using an insertion tool, in accordance with one embodiment of the present invention.

FIGS. 20A-20C show a method of implanting the surgical fastener of FIGS. 18A-18B using the insertion tool of FIGS. 19A-19C, in accordance with one embodiment of the present invention.

FIG. 20B-1 shows an expanded view of the surgical fastener and the distal end of the insertion tool shown in FIG. 20B.

DETAILED DESCRIPTION

Figure 1A:
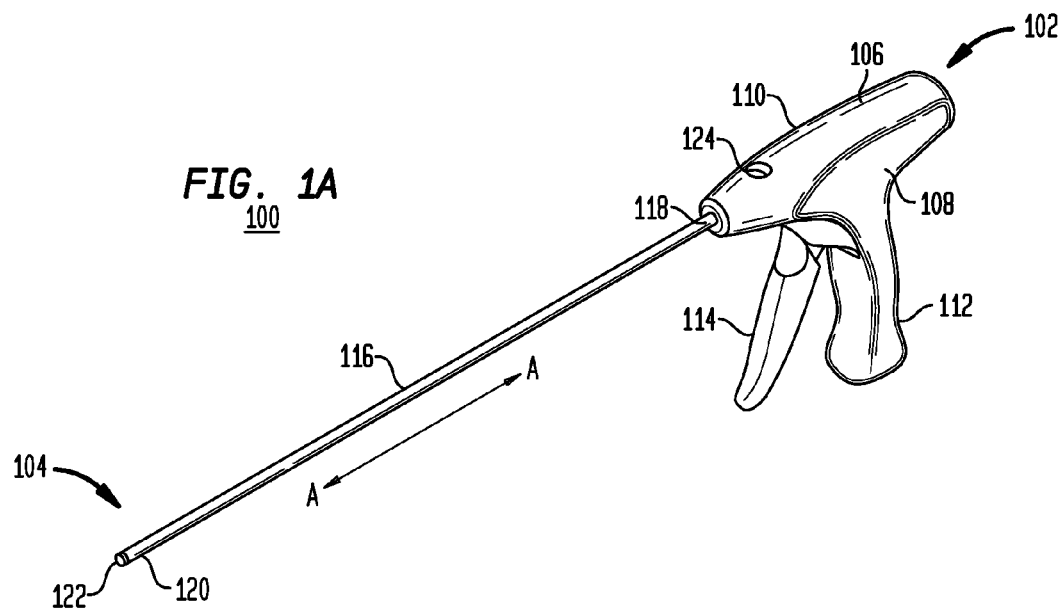
FIG. 1A shows a perspective view of an applicator instrument for dispensing surgical fasteners, in accordance with one embodiment of the present invention.
Figure 1B:
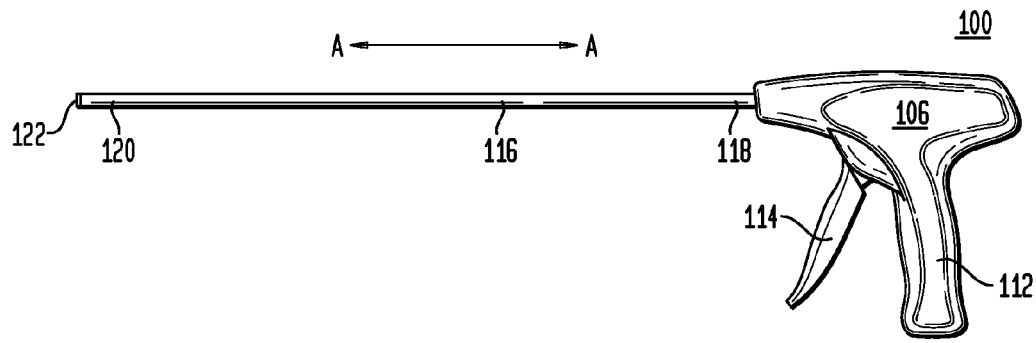
FIG. 1B shows a left side view of the applicator instrument shown in FIG. 1A.
Figure 1C:
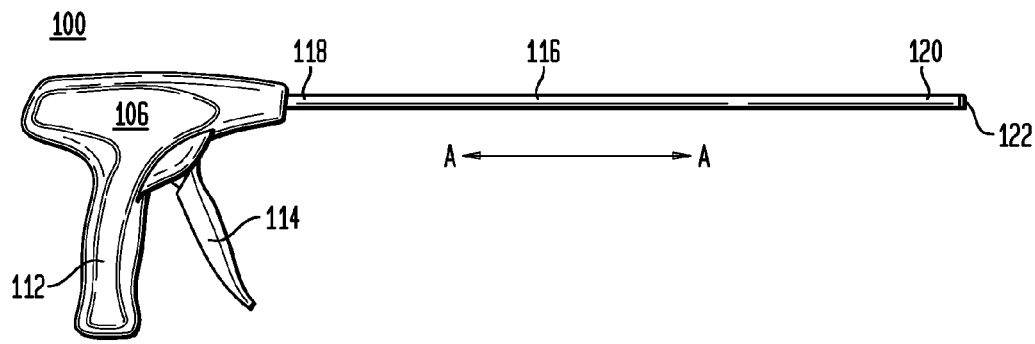
FIG. 1C shows a right side view of the applicator instrument shown in FIG. 1A.

Referring to FIGS. 1A-1C, in one embodiment, an applicator instrument 100 for dispensing surgical fasteners has a proximal end 102 and a distal end 104. The applicator instrument 100 includes a housing 106 that contains a firing system for deploying the surgical fasteners. The housing 106 has a left cover 108 and a right cover 110. The left and right covers 108, 110 have lower ends forming a hand grip 112. The applicator instrument 100 preferably includes a trigger 114 that may be squeezed for dispensing the surgical fasteners from the distal end 104 of the instrument. In one embodiment, the applicator instrument 100 holds a plurality of surgical fasteners, whereby a single surgical fastener is dispensed from the distal end 104 of the applicator instrument each time the trigger 114 is squeezed. In one embodiment, the applicator instrument holds a plurality of surgical fasteners that are advanced toward the distal end of the outer tube 116 each time the trigger 114 is squeezed. The surgical fasteners preferably advance one position each time the trigger is squeezed.

In one embodiment, the applicator instrument 100 desirably includes an elongated outer shaft or tube 116 having a proximal end 118 coupled with a distal end of the housing 106 and a distal end 120 adapted to dispense the surgical fasteners. The distal-most end of the elongated outer tube 116 preferably has an end cap 122 secured thereto. The applicator instrument preferably has a longitudinal axis designated A-A that extends between the proximal and distal ends 102, 104 thereof. The outer tube 116 desirably extends along the longitudinal axis A-A.

Referring to FIG. 1A, in one embodiment, the housing 106 may include a lockout indicator opening 124 that provides visual access to a lockout indicator. In one embodiment, the applicator instrument initially holds a plurality of surgical fasteners that are dispensed from the distal end 120 of the outer tube 116. The lockout indicator preferably moves toward a lockout condition that occurs after all of the surgical fasteners have been dispensed. The lockout indicator opening 124 may provide an indication of how many surgical fasteners have been dispensed, how many surgical fasteners remain in the applicator instrument, and/or when the lockout condition is reached.

Figure 2:
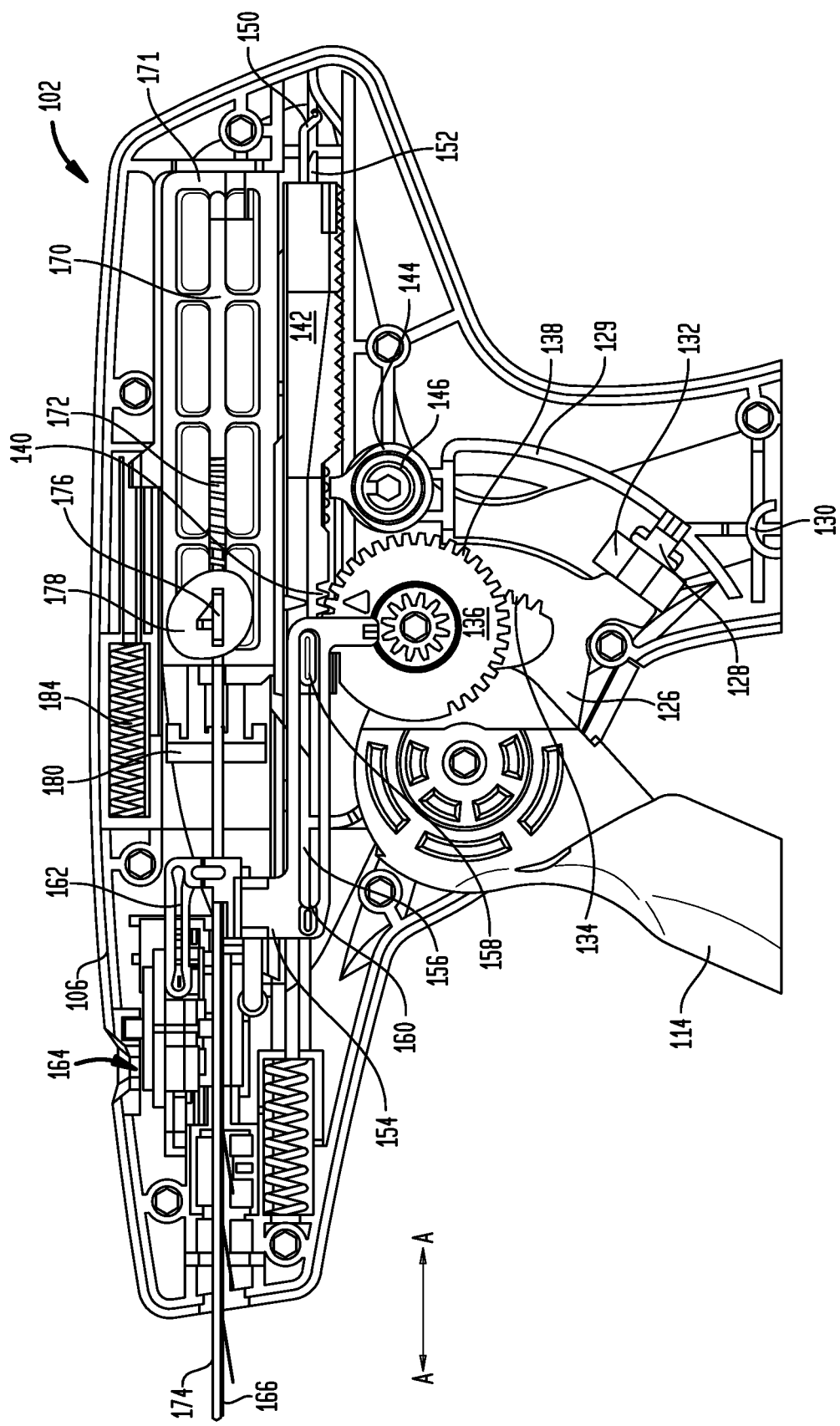
FIG. 2 shows a cross sectional view of a proximal end of the applicator instrument shown in FIGS. 1A-1C, in accordance with one embodiment of the present invention.

Referring to FIG. 2, in one embodiment, the housing 106 preferably contains a firing system for dispensing one or more surgical fasteners from the distal end of the instrument. As will be described in more detail below, many of the components of the firing system move along the longitudinal axis A-A, between the proximal and distal ends of the instrument. The components generally move toward the distal end 104 as the trigger 114 is pulled or squeezed and reverse direction to move toward the proximal end as the trigger opens.

In FIG. 2, the left cover 108 (FIG. 1A) of the housing 106 has been removed to reveal at least some of the components of the firing system. In one embodiment, the firing system includes the trigger 114 having a trigger gear 126 coupled therewith. The trigger gear 126 preferably includes a trigger return projection 128 adapted to travel within a trigger guide path 129. The trigger return projection 128 is desirably coupled with an upper end of a trigger return spring 130. In one embodiment, the trigger return spring 130 is stretched as the trigger 114 is squeezed for storing energy in the trigger return spring. When the trigger is free to return to the open position, the trigger return spring 130 preferably pulls the trigger return projection 128 toward the initial position shown in FIG. 2. The firing system preferably includes a trigger dampening element 132 coupled with the trigger return projection 128 for dampening movement of the trigger 114 as it approaches the ends of the trigger guide path 129. The trigger dampening element 132 may be made of a compliant material such as a polymer or rubber.

The trigger gear 126 includes trigger gear teeth 134 adapted to engage a first set of teeth (not shown) provided on a drive gear 136. The drive gear 136 includes a second set of teeth 138 adapted to mesh with teeth 140 providing on an underside of a yoke 142. The drive gear 136 is driven by the trigger gear 126. As the trigger 114 is squeezed, the trigger gear 126 rotates the drive gear 136 in a counter clockwise direction. As the trigger 114 opens, the trigger gear 126 rotates the drive gear 136 in a clockwise direction.

In one embodiment, the firing system includes a yoke 142 that is adapted to move distally and proximally along the longitudinal axis A-A of the applicator instrument. In one embodiment, the yoke 142 is directly coupled to the trigger 114 through the trigger gear 126 and the drive gear 136. As the trigger 114 is squeezed to the closed trigger position, the trigger gear 126 and the drive gear 136 move the yoke 142 distally (to the left in FIG. 2). As the trigger 114 returns to the open trigger position, the trigger gear 126 and the drive gear 136 move the yoke 142 proximally (to the right in FIG. 2).

In one embodiment, the firing system preferably includes a ratchet pawl 144 having a ratchet pawl projection 145 that engages teeth on an underside of the yoke 142. The ratchet pawl is desirably coupled with a ratchet pawl torsion spring 146. As will be described in more detail below, during at least one stage of a firing cycle, the ratchet pawl 144 constrains the yoke 142 from changing direction until the trigger 114 is completely closed or completely open. In one embodiment, as the trigger 114 is pulled, the yoke 142 is required to move distally beyond the projection 145 on the ratchet pawl 144 before the yoke is able to change directions and move proximally.

The firing system preferably includes a primary latch 150 that projects from a distal end of the yoke 142. The primary latch 150 is connected to the yoke 142 and moves simultaneously in distal and proximal directions with the yoke. In one embodiment, the primary latch 150 is adapted to move around a primary latch racetrack 152 formed in the housing 106 for systematically coupling and de-coupling the yoke 142 from another component of the firing system, as will be described in more detail below. In one embodiment, as the yoke 142 moves distally, the primary latch 150 preferably moves over the primary latch racetrack 152. As the yoke 142 moves proximally, the primary latch 150 preferably moves under the primary latch racetrack 152.

The firing system preferably includes an indexer 154 that is adapted to move in distal and proximal directions along the longitudinal axis A-A of the applicator instrument. The indexer 154 includes a lower slot 156 that is in communication with a boss 158 extending from a side of the yoke 142, hereinafter referred to as the yoke boss 158. The yoke boss 158 is adapted to slide within the lower slot 156 of the indexer 154. In one embodiment, when the yoke boss 158 reaches a distal end 160 of the lower slot 156 of the indexer, the yoke boss 158 urges the indexer 154 to move toward the distal end of the applicator instrument 100. The indexer 154 includes an upper slot 162 coupled with a lockout indicator system, as will be described in more detail below.

In one embodiment, the indexer 154 is directly coupled to an advancer 166 that is adapted to advance surgical fasteners toward the distal end of the applicator instrument. As the indexer 154 moves distally, the advancer 166 moves simultaneously with the indexer toward the distal end of the applicator instrument. As the indexer moves proximally, the advancer 166 moves simultaneously with the indexer toward the proximal end of the applicator instrument. In one embodiment, the advancer 166 is adapted to move the surgical fasteners toward the distal end of the applicator instrument so that the surgical fasteners may be dispensed from the distal end of the instrument. In one embodiment, the surgical fasteners are advanced one position each time the advancer moves proximally.

In one embodiment, the firing system desirably includes a spring block 170 that is selectively coupled with the yoke 142 through the primary latch 150. The spring block is preferably adapted to move distally and proximally along the longitudinal axis designated A-A. In one embodiment, when the primary latch 150 is coupled with the spring block, the yoke and the spring block preferably move simultaneously with one another as a unit. When the primary latch 150 is de-coupled from the spring block 170, the yoke 142 and the spring block preferably move independently of one another.

In one embodiment, the firing system also preferably includes a firing spring 172 disposed within the spring block 170. The firing spring 172, which is pre-compressed within the spring block, desirably has a distal end coupled with a firing rod 174 and a proximal end that engages a proximal end wall 171 of the spring block. In one embodiment, the proximal end of the firing rod 174 desirably has a cruciform-shaped coupling 176 that is connected with the distal end of the firing spring 172. One or more firing rod dampers 178 may be connected with the cruciform-shaped coupling 176 for dampening movement of the firing rod 174 as it reaches the distal and/or proximal ends of its travel path.

In one embodiment, the firing system includes a firing spring release latch 180 that constrains distal movement of the firing rod. During one stage of a firing cycle, the firing spring release latch constrains the firing rod from distal movement as energy is stored in the firing spring 172. During a later stage of the firing cycle, the firing spring release latch releases the firing rod 174 for distal movement. As will be described in more detail below, in one embodiment, the firing latch 180 preferably engages an outer surface of the spring block 170. The outer surface of the spring block preferably urges the firing latch into a release position so as to release the firing rod 174 for distal movement.

In one embodiment, the firing system desirably includes a firing rod return spring 184 that engages the spring block 170 for returning the spring block 170 to the initial, proximal position shown in FIG. 2. As the spring block 170 moves distally (to the left), energy is stored in the firing rod return spring 184. The energy is later released for moving the spring block proximally. At this stage, the firing rod may move proximally with the spring block. The firing system also desirably includes one or more dampening springs 186 that are adapted to engage one or more components of the firing system for dampening movement of the components toward the ends of travel ranges. The dampening springs preferably minimize noise, vibration, violent movements, etc. during firing cycles.

Figure 3A:
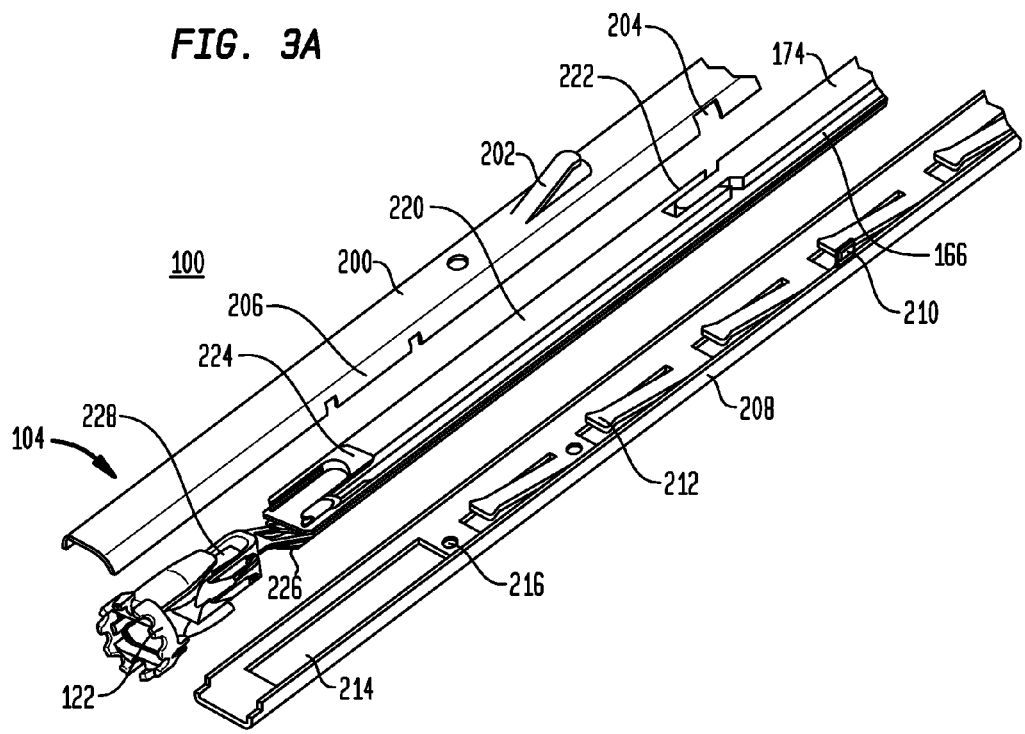
FIG. 3A shows an exploded perspective view of a distal end of the applicator instrument shown in FIGS. 1A-1C, in accordance with one embodiment of the present invention.

Referring to FIG. 3A, in one embodiment, a distal end 104 of the applicator instrument 100 is adapted to deliver surgical fasteners 232. The outer tube (FIG. 1A) that normally surrounds the components shown in FIG. 3A has been removed to more clearly show the internal components. In the particular embodiment shown in FIG. 3A, the internal components at the distal end 104 of the applicator instrument 100 have been exploded for more clearly showing the parts and the operation of the applicator instrument.

Referring to FIG. 3A, in one embodiment, the applicator instrument 100 includes a ceiling stamping 200 having one or more ceiling stamping spring tabs 202 provided along the length thereof. The ceiling stamping 200 preferably includes one or more ceiling stamping assembly notches 204 formed in side walls thereof for facilitating assembly of the applicator instrument. The ceiling stamping 200 preferably includes a pair of opposed alignment guides that 206 that are adapted to guide distal and proximal movement of the firing rod, as will be described in more detail below.

The applicator instrument also preferably includes an anti-backup stamping 208 that is assembled with the ceiling stamping 200. The anti-backup stamping 208 includes side walls having assembly tabs 210 projecting therefrom. The assembly tabs 210 are adapted to be aligned with the assembly grooves 204 on the ceiling stamping 200 to facilitate proper alignment and assembly of the ceiling stamping with the anti-backup stamping. The anti-backup stamping 208 desirably includes anti-backup tabs 212 provided along the length thereof. The anti-backup tabs preferably project toward the distal end of the applicator instrument and allow the surgical fasteners to move in only one direction, namely distally. The anti-backup tabs 212 desirably constrain the surgical fasteners from moving toward the proximal end of the applicator instrument.

Referring to FIG. 3A, the anti-backup stamping 208 preferably includes a staging leaf opening 214 provided adjacent a distal end of the anti-backup stamping 208, and an aperture 216 proximal the staging leaf opening 214 that is desirably used for securing a staging leaf assembly to the anti-backup stamping 208, as will be described in more detail below.

The applicator instrument preferably includes the firing rod 174 having an insertion fork 220 at a distal end thereof. The insertion fork 220 has a proximal end 222 coupled with a distal end of the main section of the firing rod 174, and a distal end 224 adapted to engage the surgical fasteners. The distal end of the application instrument also preferably includes the staging leaf assembly including a staging leaf support 226 and a staging leaf 228. Proximal ends of the respective staging leaf support 226 and the staging leaf 228 are aligned with the aperture 216 in the anti-backup stamping 208.

The applicator instrument also preferably includes the advancer 166, which is adapted to advance surgical fasteners toward the distal end of the instrument. The advancer desirably has advancer tabs 230 adapted to engage the surgical fasteners for urging the surgical fasteners toward the distal end of the application instrument. In one embodiment, the advancer 166 advances the surgical fastener one position toward the distal end of the applicator instrument each time the trigger is squeezed closed.

Figure 3B:
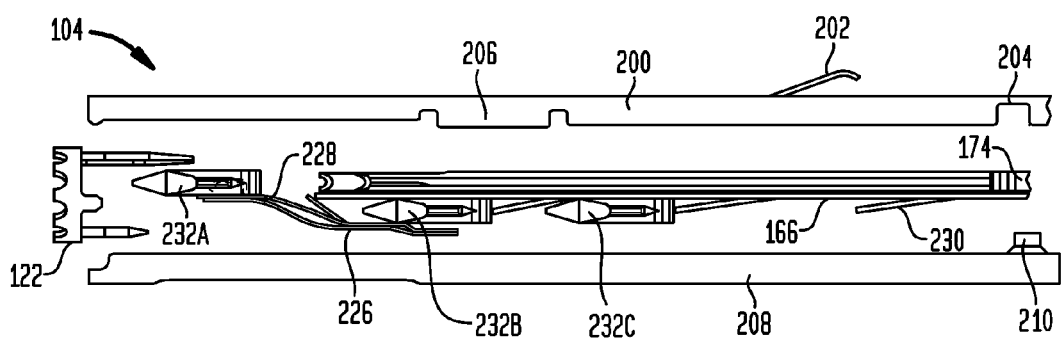
FIG. 3B shows an exploded left side view of the distal end of the applicator instrument shown in FIG. 3A.

FIG. 3B shows an exploded side view of the distal end 104 of the applicator instrument 100. The ceiling stamping 200 is adapted for assembly with the opposed anti-backup stamping 208. The assembly grooves 204 on the ceiling stamping 200 are preferably aligned with the assembly tabs 210 on the anti-backup stamping 208. The firing rod 174 including the insertion fork 220, the advancer 166, the staging leaf support 226 and the staging leaf spring 228 are preferably at least partially disposed between the ceiling stamping 200 and the anti-backup stamping 208. After the components shown in FIG. 3B have been assembled together, the components are desirably disposed within the outer tube 116 shown in FIGS. 1A-1C. In one embodiment, the end cap 122 is desirably assembled with distal-most ends of the outer tube 116, the ceiling stamping 200, and the anti-backup stamping 208. In one embodiment, the ceiling stamping spring tabs 202 preferably press against the inner surface of the outer tube for minimizing movement of the internal components within the outer tube.

Referring to FIG. 3B, in one embodiment, the advancer 166 includes a series of advancer tabs 230 projecting from an underside of the advancer. The advancer tabs 230 preferably project toward the distal end of the advancer 166. The advancer tabs 230 desirably engage surgical fasteners 232 disposed within the outer tube for urging the surgical fasteners toward the distal end of the applicator instrument. In one embodiment, a plurality of surgical fasteners 232A-232D are desirably provided within the applicator instrument. Each time the trigger is squeezed, the advancer tabs 230 urge the surgical fasteners 232A-232D toward the distal end of the instrument for being dispensed from the distal end of the instrument. When a trailing surgical fastener (e.g. the fastener designated 232B) is advanced sufficiently to become a lead surgical fastener (e.g. the lead fastener designated 232A), it is advanced into contact with the staging leaf 228, which is adapted to move the lead surgical fastener 232A into alignment with tines at the distal end of the insertion fork 220.

Figure 4A:
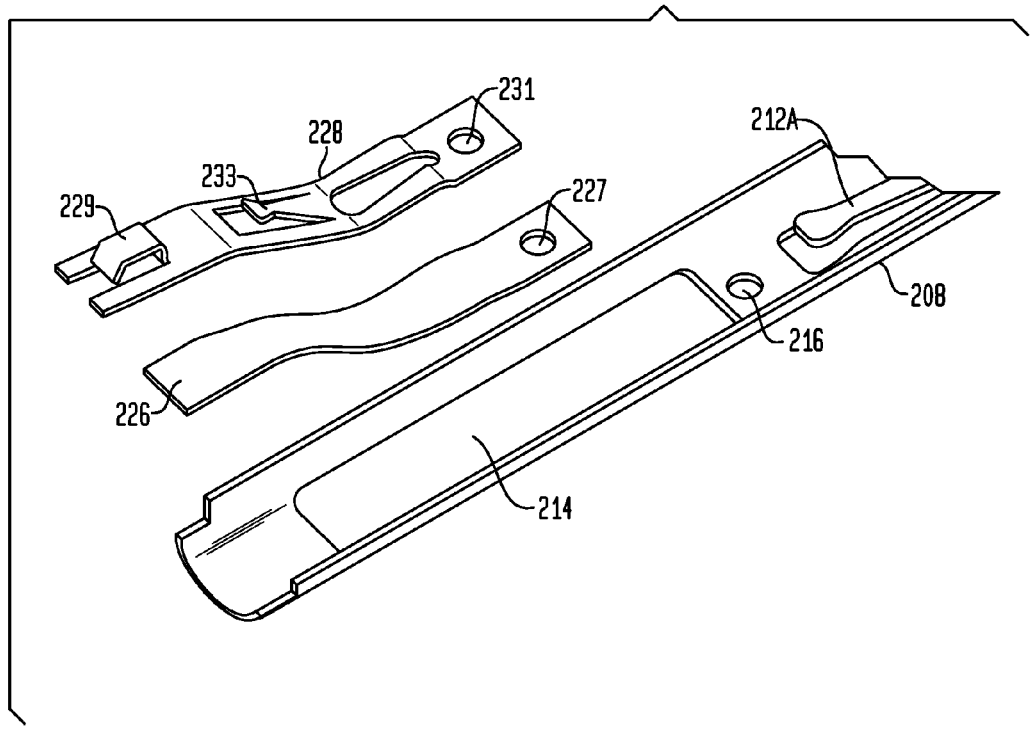
FIGS. 4A-4E show a staging leaf assembly for the applicator instrument shown in FIGS. 1A-1C, in accordance with one embodiment of the present invention.

Referring to FIGS. 4A-4E, in one embodiment, the applicator instrument includes the staging leaf assembly located adjacent the distal end of the anti-backup stamping 208. Referring to FIG. 4A, in one embodiment, the anti-backup stamping 208 includes the anti-backup tabs 212 projecting toward the distal end of the anti-backup stamping 208. The anti-backup stamping 208 includes the staging leaf opening 214 preferably disposed between the final anti-backup tab 212A and the distal end of the anti-backup stamping 208. The anti-backup stamping 208 also preferably includes the opening 216 proximal the staging leaf opening 214. The aperture is preferably adapted to be aligned with a proximal end of the staging leaf support 226 and the staging leaf 228.

Referring to FIG. 4A, as noted above, the staging leaf assembly preferably includes the staging leaf support 226 and the staging leaf 228. The staging leaf support 226 has an opening 227 at a proximal end thereof that is desirably aligned with the opening 216 in the anti-backup stamping 208. The staging leaf 228 desirably includes a distal end having a staging leaf tab 229 and a proximal end including an opening 231 that is adapted to be aligned with the opening 216 in the anti-backup stamping and the opening 227 in the staging leaf support. The staging leaf 228 also includes a staging leaf anti-backup tab 233 projecting toward the distal end of the staging leaf 228.

Figure 4B:
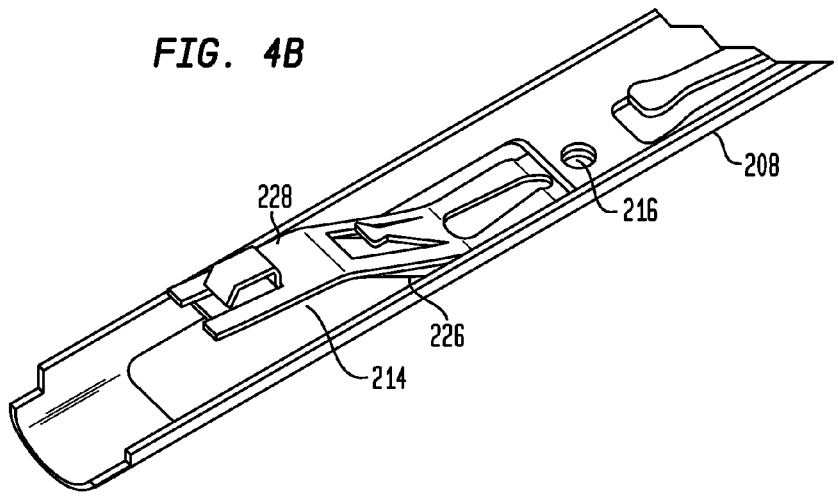
Figure 4C:
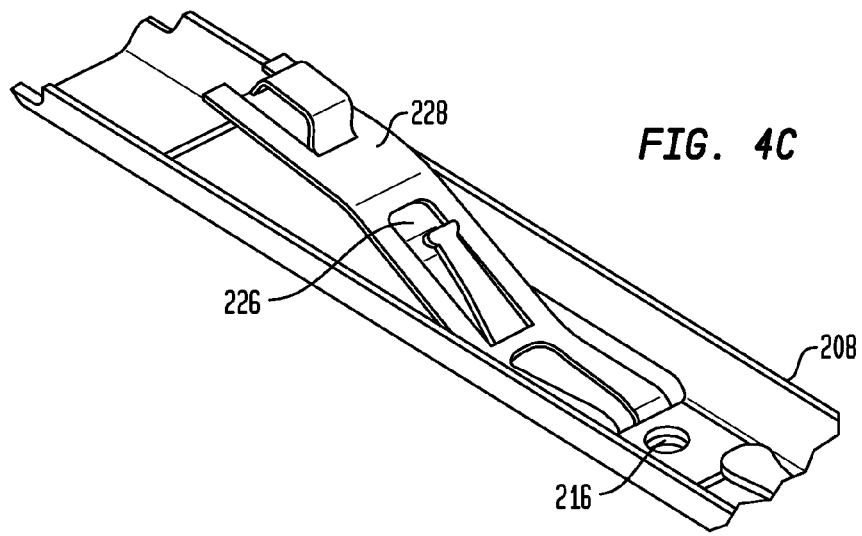

FIGS. 4B-4E show how the staging leaf support 226 and the staging leaf 228 are assembled with the anti-backup stamping 208. As shown in FIGS. 4B and 4C, in one embodiment, the staging leaf 228 is positioned over the staging leaf support 226 and the proximal ends of the assembled components are passed through the staging leaf opening 214 so that the openings 227, 231 at the proximal ends of the staging leaf support 226 and the staging leaf 228 are aligned with the opening 216 in the anti-backup stamping 208.

Figure 4D:
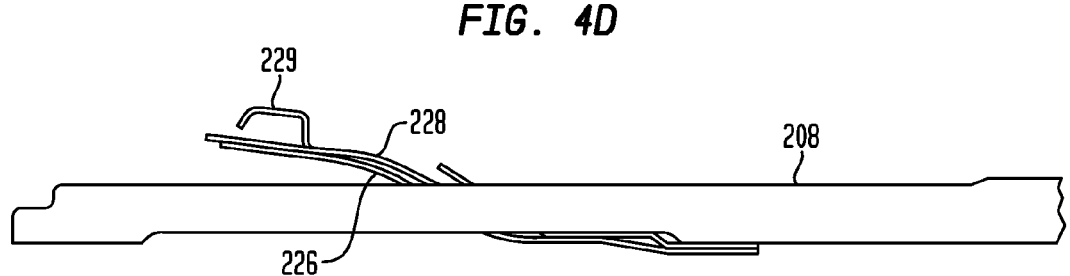
Figure 4E:
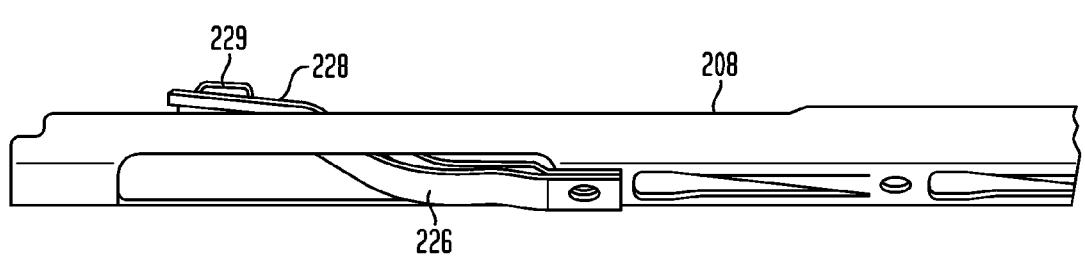

Referring to FIGS. 4D and 4E, the proximal ends of the staging leaf 228 and the staging leaf support 226 underlie a bottom surface of the anti-backup stamping 208, and are preferably permanently connected to the underside surface of the anti-backup stamping. The connection may be made using a fastener, such as a screw, or other well-known connecting methods such as welding. As shown in FIGS. 4D and 4E, the distal ends of the staging leaf 228 and the staging leaf support 226 extend through the staging leaf opening 214, with the staging leaf tab 229 normally projecting above the anti-backup stamping 208.

Although the present invention is not limited by any particular theory of operation, it is believed that the staging leaf assembly provides a spring-like device at the distal end of the anti-backup stamping for urging and/or moving a lead surgical fastener into alignment with the tines at the distal end of the insertion fork. The staging leaf assembly may be deflected downwardly by the distal ends of the advancer and the insertion fork when those components are extended toward the distal end of the applicator instrument. When the insertion fork and the advancer are retracted proximal to the staging leaf assembly, however, the staging leaf assembly desirably springs upwardly to the position shown in FIGS. 4B-4E. As the staging leaf assembly springs upwardly, a lead surgical fastener positioned atop the staging leaf assembly is moved into alignment with the distal end of the insertion fork. In one embodiment, the staging leaf tab 229 and the staging leaf anti-backup tab 233 stabilize the lead surgical fastener and hold the lead surgical fastener in place as the insertion fork is advanced to secure the lead surgical fastener.

Figure 5A:
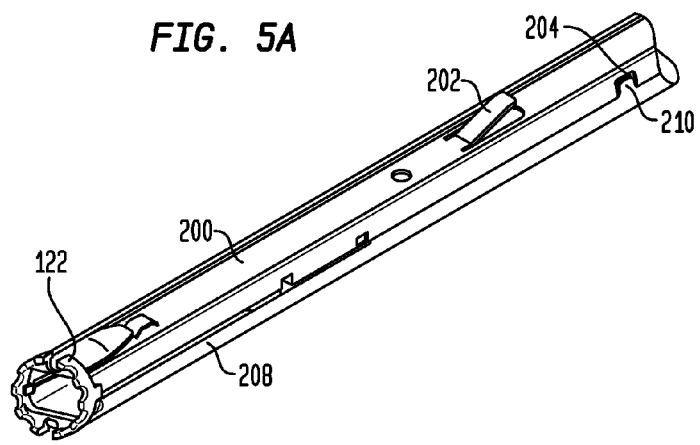
FIG. 5A shows a perspective view of a distal end of an applicator instrument for dispensing surgical fasteners, in accordance with one embodiment of the present invention.
Figure 5B:
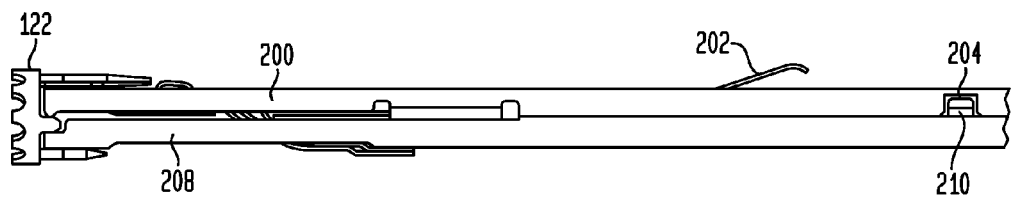
FIG. 5B shows a side view of the distal end of the applicator instrument shown in FIG. 5A.
Figure 5C:
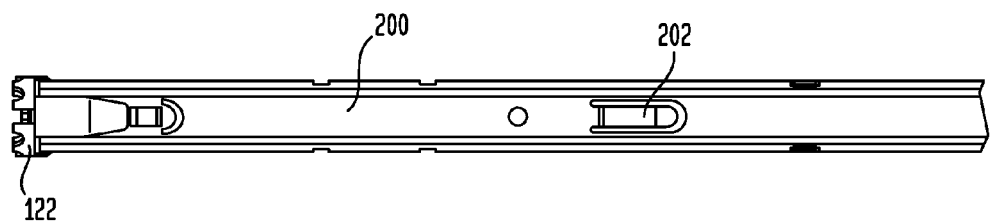
FIG. 5C shows a top plan view of the distal end of the applicator instrument shown in FIGS. 5A and 5B.

Referring to FIGS. 5A-5C, in one embodiment, the ceiling stamping 200 is assembled with the anti-backup stamping 208. The ceiling stamping 200 includes at least one assembly groove 204 that is aligned with at least one assembly tab 210 on the anti-backup stamping 208 for ensuring proper alignment of the stampings 200, 208 with one another. The distal-most ends of the ceiling stamping 200 and the anti-backup stamping 208 are preferably held together by the end cap 122. In one embodiment, the ceiling stamping has ceiling stamping spring tabs 202 that preferably engage an inner surface of the outer tube (not shown) for enhancing the stability of the applicator instrument and preventing the ceiling stamping and the anti-backup stamping from moving relative to the outer tube. In one embodiment, the end cap 122, and the distal-most ends of the ceiling stamping and the anti-backup stamping have one or more tongue and groove structures for assembling the end cap 122 with the ceiling and anti-backup stampings 200, 208.

Figure 6:
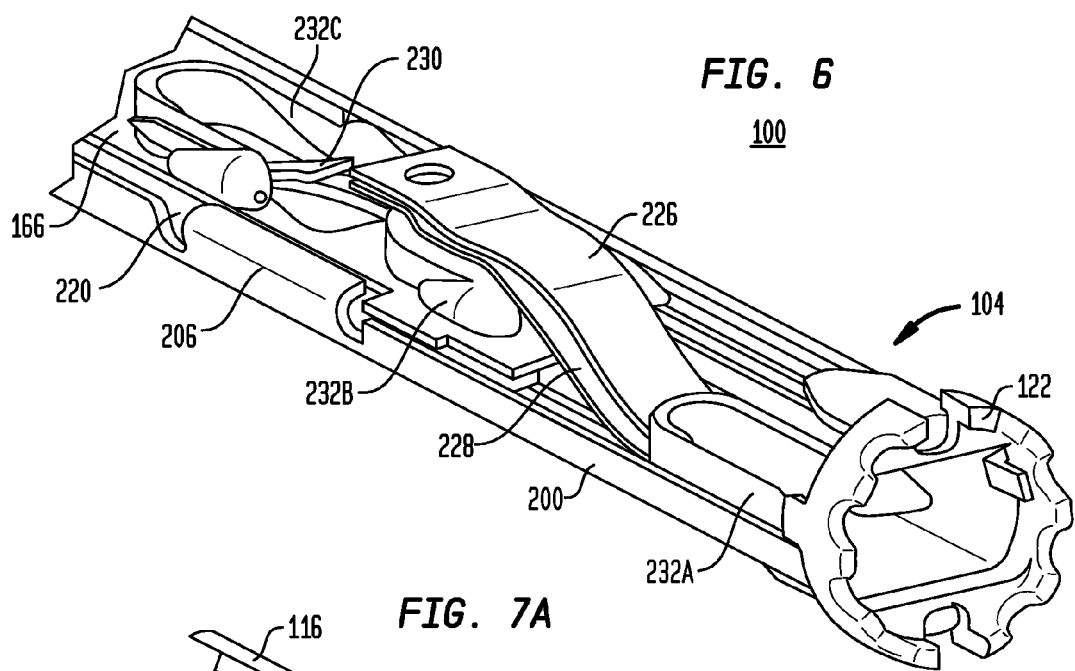
FIG. 6 shows a perspective view of a distal end of an applicator instrument, in accordance with one embodiment of the present invention.

Referring to FIG. 6, in one embodiment, distal-most ends of the ceiling stamping 200 and the anti-backup stamping 208 are held together by the end cap 122. In one embodiment, the ceiling stamping 200 may include a pair of guide flanges 206 that preferably conform to the side walls of the insertion fork 220 as the firing rod moves distally and proximally. In one embodiment, the guide flanges 206 preferably guide the distal and proximal movement of the insertion fork 220 to ensure proper alignment of the tines of the insertion fork with the lead surgical fastener 232A. The applicator instrument 100 desirably includes the staging leaf assembly including the staging leaf support 226 and the staging leaf 228. As noted above, proximal ends of the staging leaf support 226 and the staging leaf 228 are desirably coupled with the anti-backup stamping 208. In one embodiment, the advancer 166 is desirably positioned between the staging leaf assembly and the insertion fork 220. The advancer 166 includes advancer tabs 230 that engage the surgical fasteners 232 for advancing the surgical fasteners toward the distal end 104 of the applicator instrument 100. Each time the advancer moves distally, the advancer tabs preferably advance the surgical fasteners one position toward the distal end of the applicator instrument.

Figure 7A:
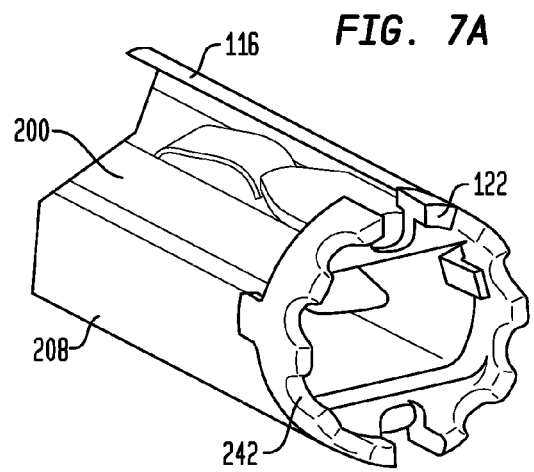
FIG. 7A shows a distal end of an applicator instrument including an outer tube, in accordance with one embodiment of the present invention.

Referring to FIG. 7A, in one embodiment, the outer tube 116 is disposed around the ceiling stamping 200 and the anti-backup stamping 208. In FIG. 7A, the outer tube 116 is transparent so that the ceiling stamping and the anti-backup stamping are visible. The end cap 122 is secured over the distal end of the outer tube 116 and includes assembly flanges that are disposed between the outer tube 116, and the ceiling stamping and anti-backup stamping. The end cap 122 preferably engages the ceiling stamping 200 and the anti-backup stamping 208 so as to provide stability at the distal end of the applicator instrument 100. In one embodiment, the end cap 122 preferably includes castling 242 formed in a distal end face thereof. The castling 242 is adapted to engage surfaces (e.g. mesh) so as to prevent the distal end of the applicator instrument from sliding or moving relative to the opposing surfaces. The castling 242 may also be used for aligning the distal end of the applicator instrument with a prosthetic device, such as a prosthetic mesh. In one embodiment, the castling may be used to align the distal end of the applicator instrument with one or more strands on a prosthetic device.

Figure 7B:
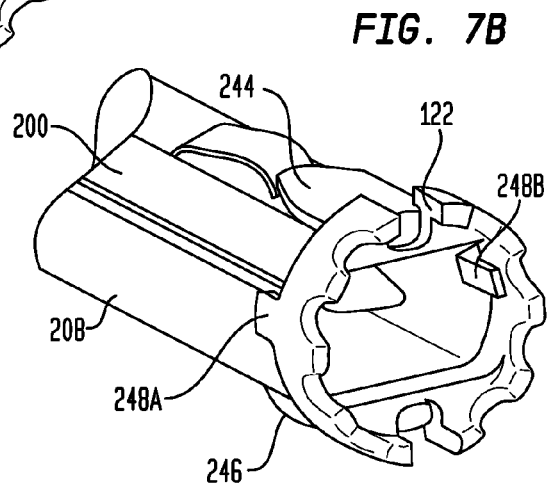
FIG. 7B shows the distal end of the applicator instrument of FIG. 7A with the outer tube removed.

FIG. 7B shows the distal end of the applicator instrument of FIG. 7A with the outer tube 240 removed. The end cap 122 includes a top assembly flange 244 that engages the ceiling stamping 200 and a bottom assembly flange 246 that engages the anti-backup stamping 208. The top and bottom assembly flanges 244, 246 preferably hold the distal-most ends of the ceiling stamping and the anti-backup stamping together for stabilizing the distal end of the applicator instrument. The inner face of the end cap 122 preferably includes a pair of side assembly tabs 248A, 248B that are disposed between the ceiling stamping and the anti-backup stamping. The side assembly tabs 248A, 248B may also enhance stability of the distal end of the applicator instrument.

Figure 8A:
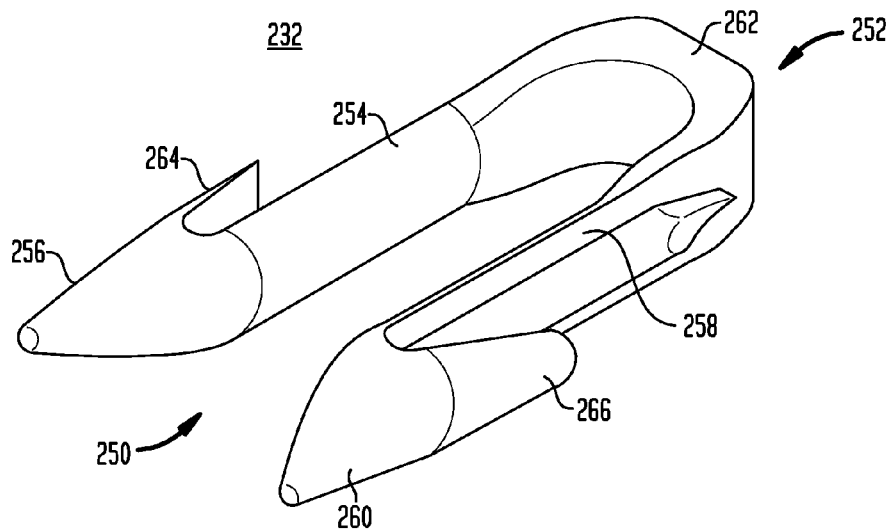
FIG. 8A shows a perspective view of a surgical fastener, in accordance with one embodiment of the present invention.
Figure 8B:
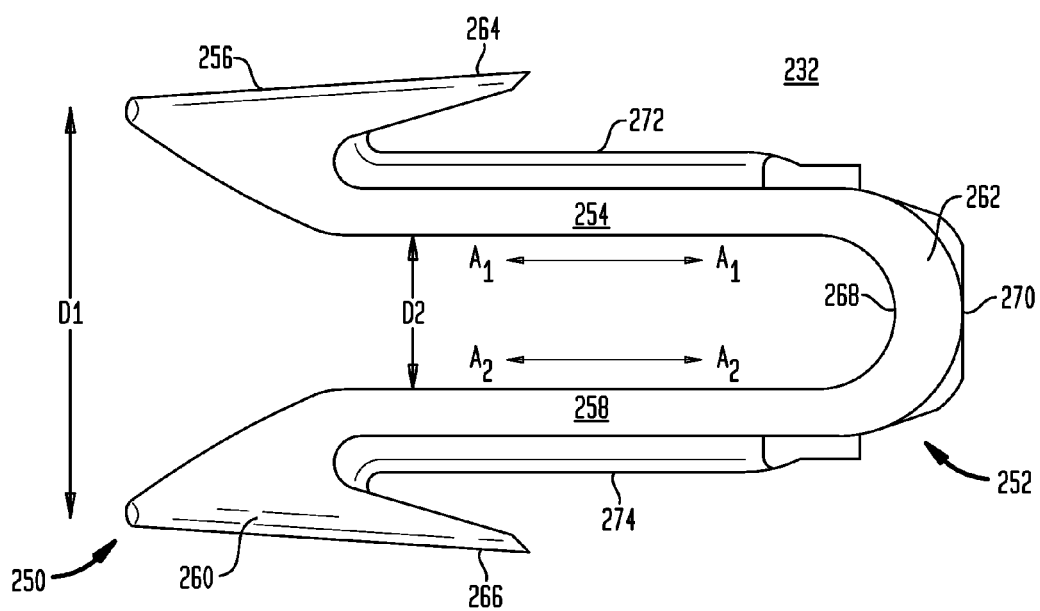
FIG. 8B shows a front view of the surgical fastener shown in FIG. 8A.

Referring to FIGS. 8A-8F, in one embodiment, the applicator instrument dispenses surgical fasteners from a distal end thereof. Referring to FIGS. 8A and 8B, in one embodiment, a surgical fastener 232 desirably includes a distal end 250 and a proximal end 252. The surgical fastener 232 preferably includes a first leg 254 having a first tip 256 provided at a distal end of the first leg, and a second leg 258 having a second tip 260 provided at a distal end of the second leg. In one embodiment, the cross-sectional dimension of each first and second leg diminishes when moving from the proximal ends toward the distal ends of the legs. The surgical fastener 232 preferably includes a bridge 262 adjacent the proximal end 252 of the surgical fastener that connects the proximal ends of the first and second legs 254, 258. In one embodiment, the bridge may be positioned between the proximal and distal ends of the surgical fastener so long as it interconnects the first and second legs. The surgical fastener 232 preferably includes at least one first barb 264 projecting rearwardly from the first tip 256 and at least one second barb 266 projecting rearwardly from the second tip 260. Although only one barb is shown on each leg, other surgical fasteners may have multiple barbs on each leg or tip. The first and second tips 256, 260 may be conical in shape. The respective tips may be formed with sharp leading points or may be more obtuse.

In one embodiment, the first and second tips 256, 260 have skewed distal piercing tips or insertion tips that are skewed with respect to longitudinal axes of the respective first and second legs 254, 258. In one embodiment, the distal piercing tips are skewed outwardly with respect to the longitudinal axes of the first and second legs. In one embodiment, the distance between the tips is greater than the distance between the legs for increasing the likelihood of fibers of a prosthetic device being captured between the legs. In one embodiment, the first and second tips 256, 260 have blunt distal piercing points. The blunt points enable the surgical fastener to penetrate tissue while minimizing unwanted penetration into the hand of an operator.

Referring to FIG. 8B, in one embodiment, the bridge 262 preferably includes a concave inner surface 268 facing toward the distal end 250 of the surgical fastener 232 and a convex outer surface 270 facing toward the proximal end 252 of the surgical fastener. The first leg 254 has an outer wall having a first rib 272 that extends along a longitudinal axis $A_1$ of the first leg. The second leg 258 includes an outer wall having a second rib 274 that extends along the longitudinal axis $A_2$ of the second leg. In one embodiment, the distance $D_1$ between the piercing points at the distal ends of the first and second tips 256, 260 is preferably greater than the distance $D_2$ between the opposing surfaces of the first and second legs 254, 256. The wider relative distance between the distal piercing points of the first and second tips 256, 260 preferably ensures that the surgical fastener will engage strands on a porous prosthetic device, such as the strands of a surgical mesh. In one embodiment, the outwardly skewed distal piercing tips provides increased capacity to capture surgical mesh fibers where the mesh fibers are separated from one another without the need to increase the span between each leg.

Figure 8C:
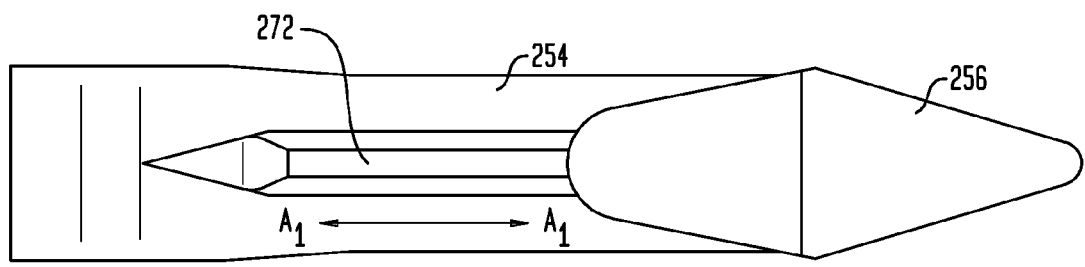
FIG. 8C shows a left side view of the surgical fastener shown in FIG. 8A including an insertion tip.

Referring to FIG. 8C, in one embodiment, the first leg 254 has the first rib 272 extending along the longitudinal axis $A_1$ of the first leg. When viewed from the side as shown in FIG. 8C, the first rib 272 is preferably in substantial alignment with a distal point of the first piercing tip 256.

Figures 1, 8C:
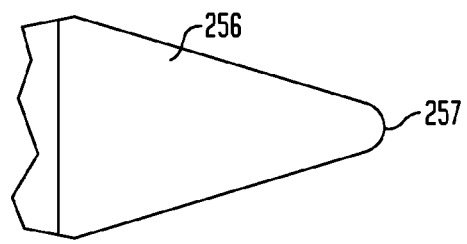

FIG. 8C-1 shows an enlarged view of the first piercing or insertion tip 256 including a blunt piercing point 257. In one embodiment, the blunt piercing point 257 enables the distal end of the surgical fastener to penetrate tissue while minimizing unwanted penetration into the hand of an operator.

Figure 8D:
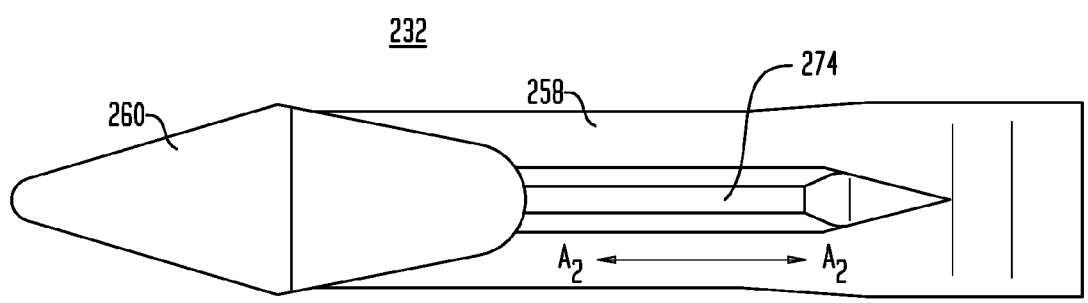
FIG. 8D shows a right side view of the surgical fastener shown in FIG. 8A.

Referring to FIG. 8D, in one embodiment, the second leg 258 has the second rib 274 extending along the longitudinal axis $A_2$ of the second leg 258. When viewed from the side as shown in FIG. 8D, the second rib 274 is preferably aligned with a distal point of the second tip 260.

Figure 8E:
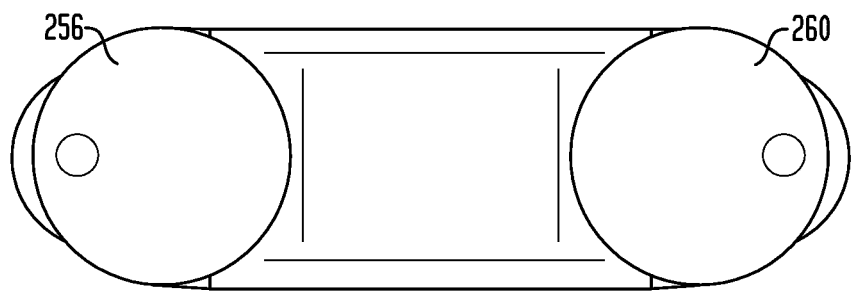
FIG. 8E shows a distal end view of the surgical fastener shown in FIG. 8A.

Referring to FIG. 8E, in one embodiment, the first and second piercing tips 256, 260 are preferably skewed outwardly from a center of the surgical fastener 232. In one embodiment, the first and second piercing tips 256, 260 are preferably asymmetrical and are configured to extend outwardly from the center of the surgical fastener 232.

Figure 8F:
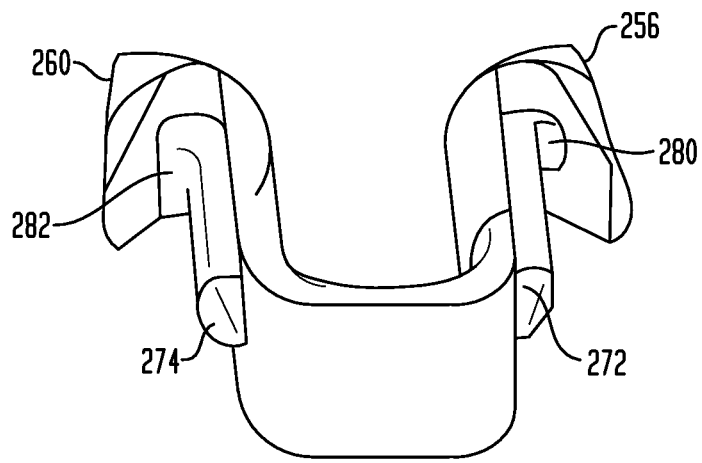
FIG. 8F shows a proximal end view of the surgical fastener shown in FIG. 8A.

Referring to FIG. 8F, in one embodiment, the rear face of the first insertion tip 256 includes a first seating surface 280 adapted to receive a distal end of a first tine of an insertion fork. The rear face of the second tip 260 preferably includes a second seating surface 282 adapted to receive a distal end of a second tine of the insertion fork. In one embodiment, the convex seating surfaces 280, 282 are preferably substantially aligned with the distal piercing points of the first and second piercing tips 256, 260. The distal ends of the tines of the insertion fork may have surfaces that conform to the respective seating surfaces 280, 282.

Figure 8G:
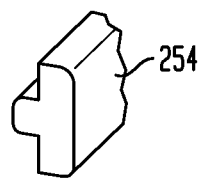
FIG. 8G shows a cross-sectional view of one of the legs of the surgical fastener shown in FIG. 8F.

Referring to FIG. 8G, in one embodiment, the first leg 254 has an inner face that is rounded and an outer face that is squared-off. Although the present invention is not limited by any particular theory of operation, it is believed that such a structure desirably increases the strength of the surgical fastener by increasing the section modulus. Providing legs having a cross-section with an inner rounded-off surface and an outer squared-off surface also preferably increases the force required to pull the surgical fastener out of tissue.

In one embodiment, the surgical fastener may be made of absorbable and/or non-absorbable materials. Preferred absorbable materials include PDS, PDS/lactide-glycolide blends, PLA, etc. In one embodiment, each surgical fastener is sized to fit inside of a 5 mm outer diameter tube (typically trocar cannula dimension). The surgical fastener is fabricated by molding, however, with small modifications, other processes such as casting, stamping, and machining may be used. In one embodiment, the surgical fasteners may be extruded into a general shape, and then formed.

Figure 9A:
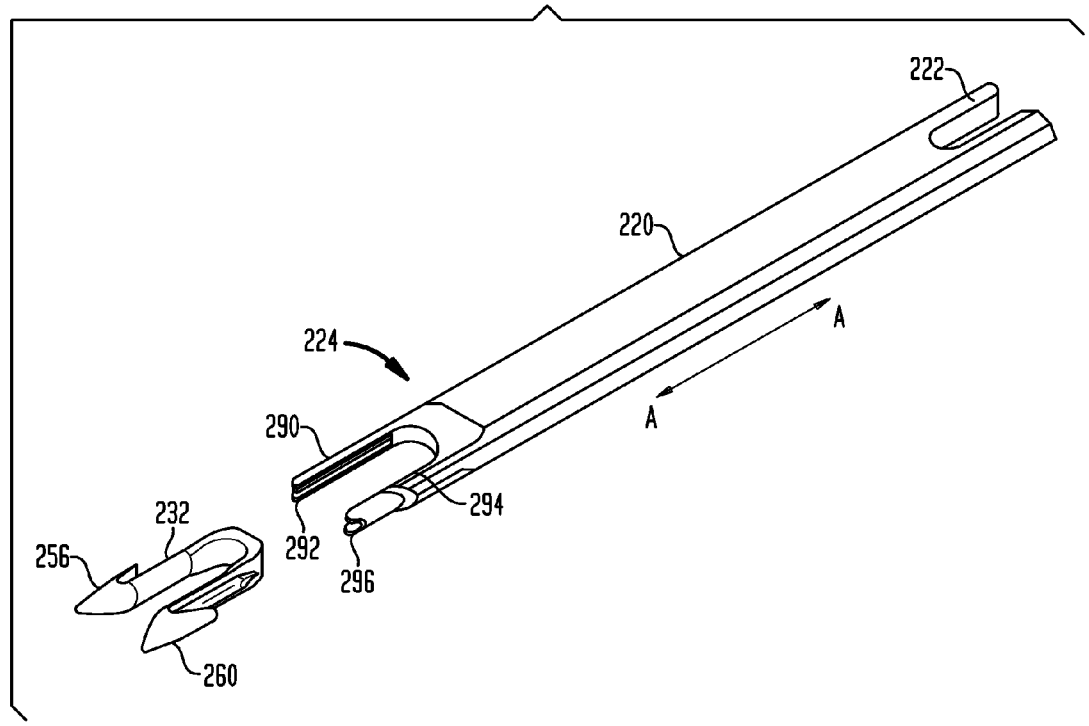
FIG. 9A shows a perspective view of an insertion fork aligned with a surgical fastener, in accordance with one embodiment of the present invention.
Figure 9B:
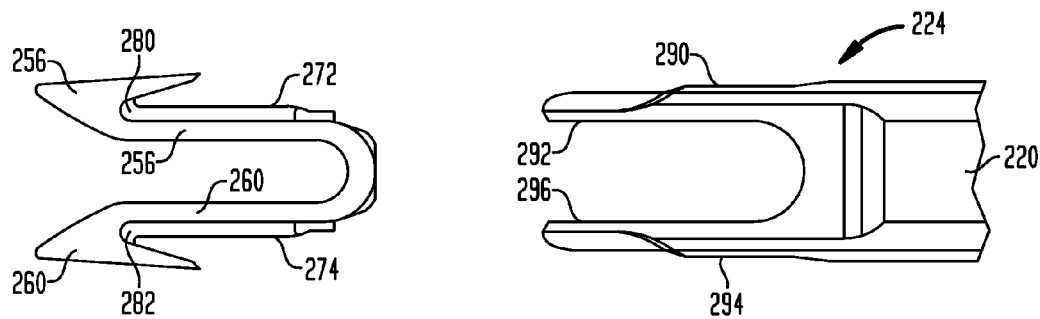
FIG. 9B shows a top plan view of the insertion fork and the surgical fastener shown in FIG. 9A.

Referring to FIGS. 9A and 9B, in one embodiment, the surgical fastener 232 is aligned with the insertion fork 220 at the distal end of the firing rod for being dispensed from the distal end of the applicator instrument. The insertion fork 220 includes a proximal end 222 adapted for connection with a distal end of a main section of a firing rod (not shown) and a distal end 224 adapted to engage one or more surfaces of the surgical fastener 232. In one embodiment, the distal end 224 of the insertion fork 220 includes a first tine 290 having a first inner groove 292 formed therein, and a second tine 294 having a second inner groove 296 formed therein. In one embodiment, the inner grooves 292, 296 preferably oppose one another and extend along axes that are parallel with the longitudinal axis A-A of the applicator instrument. In operation, the opposing inner grooves 292, 296 of the first and second tines 290, 294 are preferably adapted to slide over the ribs 272, 274 on the first and second legs 254, 258 of the surgical fastener. The engagement of the inner grooves 292, 296 with the ribs 272, 274 preferably aligns the surgical fastener element 232 with the distal end 224 of the insertion fork 220, and stabilizes the surgical fastener during implantation in tissue. In one embodiment, the distal-most tips of the first and second tines 290, 294 are advanced until they abut against the convex seating surfaces 280, 282 provided at the distal surfaces of the first and second tips 256, 260.

Although the present invention is not limited by any particular theory of operation, it is believed that providing an insertion fork with grooved tines that engage ribs on outer surfaces of the legs of a surgical fastener will enhance stability and control of the surgical fastener when dispensing the surgical fastener from the distal end of the applicator instrument. In addition, the insertion force is provided closer to the distal end of the surgical fastener and not only at the proximal end of the surgical fastener as is the case with prior art systems. This feature (i.e. providing insertion force on the surgical fastener near the distal end of the fastener) may enable smaller and/or lower profile surgical fasteners to be used.

Figure 10A:
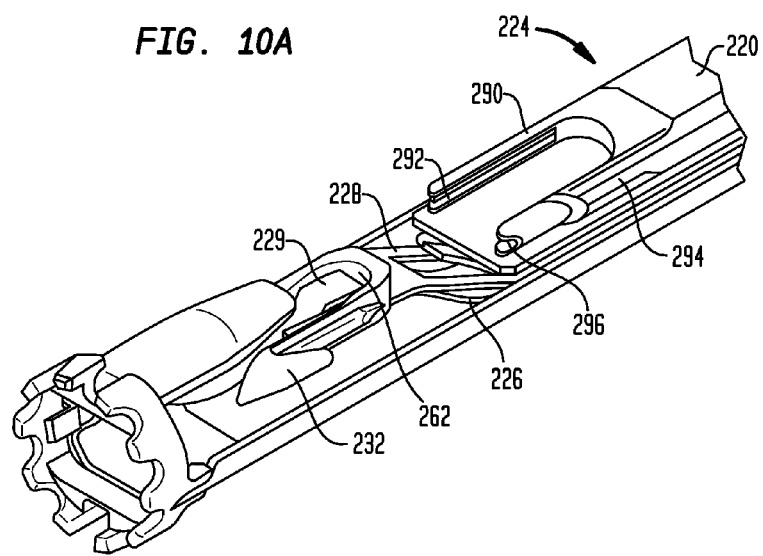
FIG. 10A shows a distal end of an applicator instrument for dispensing surgical fasteners, in accordance with one embodiment of the present invention.

Referring to FIG. 10A, in one embodiment, the staging leaf assembly includes a staging leaf support 226 and a staging leaf 228 adapted to lift a lead surgical fastener 232A into alignment with the tines at the distal end 224 of the insertion fork 220. The staging leaf 228 preferably includes a staging leaf tab 229 that may engage the inner surface of the bridge 262 of the surgical fastener 232. The ribs on the legs of the surgical fastener are preferably aligned with the opposing inner grooves 292, 296 on the opposing tines 290, 294 of the insertion fork 220.

Figure 10B:
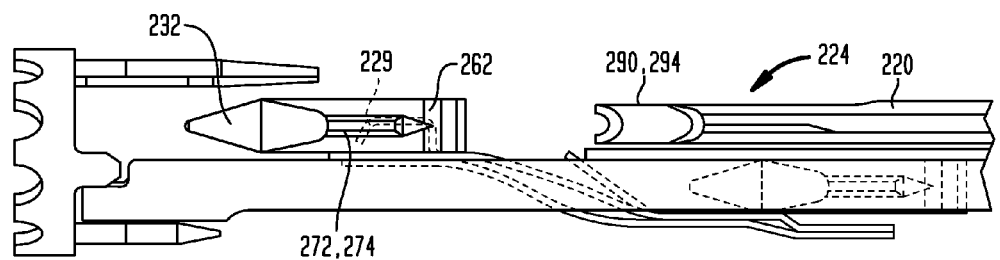
FIG. 10B shows a side view of the distal end of the applicator instrument shown in FIG. 10A.

Referring to FIG. 10B, in one embodiment, the staging leaf 228 aligns the ribs 272, 274 on the surgical fastener 232 with the inner grooves on the tines 290, 294 of the insertion fork 220. The staging leaf tab 229 preferably engages the bridge 262 of the surgical fastener 232 for stabilizing the surgical fastener 232 as the tines 290, 294 slide over the ribs 272, 274.

Figure 10C:
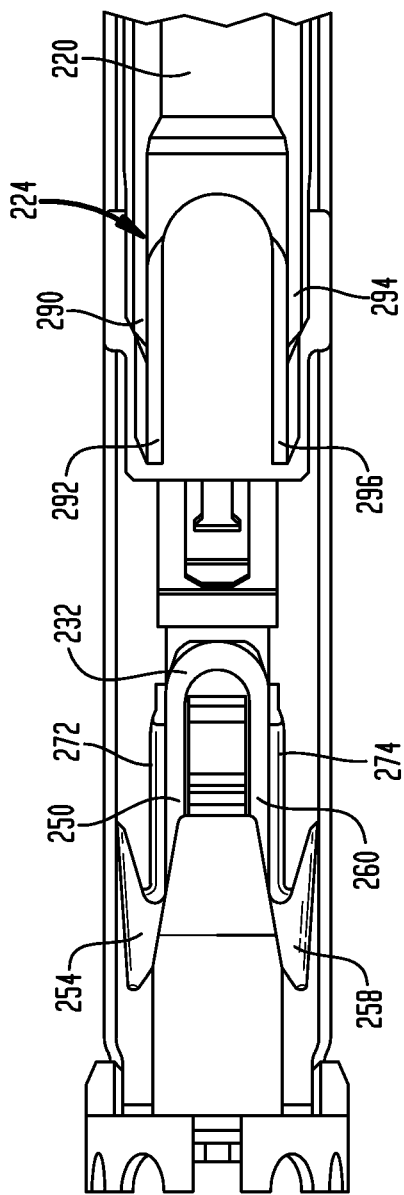
FIG. 10C shows a top plan view of the distal end of the applicator instrument shown in FIGS. 10A and 10B.

FIG. 10C shows a top plan view of the applicator instrument with the inner groove 292 of the first tine 290 aligned with the first rib 272 on the first leg 254 of the surgical fastener 232 and the inner groove 296 on the second tine 294 aligned with the second rib 274 on the second leg 258 of the surgical fastener. As the surgical fastener is held stationary by the staging leaf 228, the firing rod including the insertion fork 220 is advanced toward the surgical fastener until the distal-most ends of the tines 290, 294 are seated against the convex seating surfaces located behind the first and second tips 256, 260. After the tines 290, 294 are seated against the convex seating surfaces, the insertion fork 220 is ready for further advancement toward the distal end of the applicator instrument for dispensing the surgical fastener 232 from the applicator instrument.

Figure 11B:
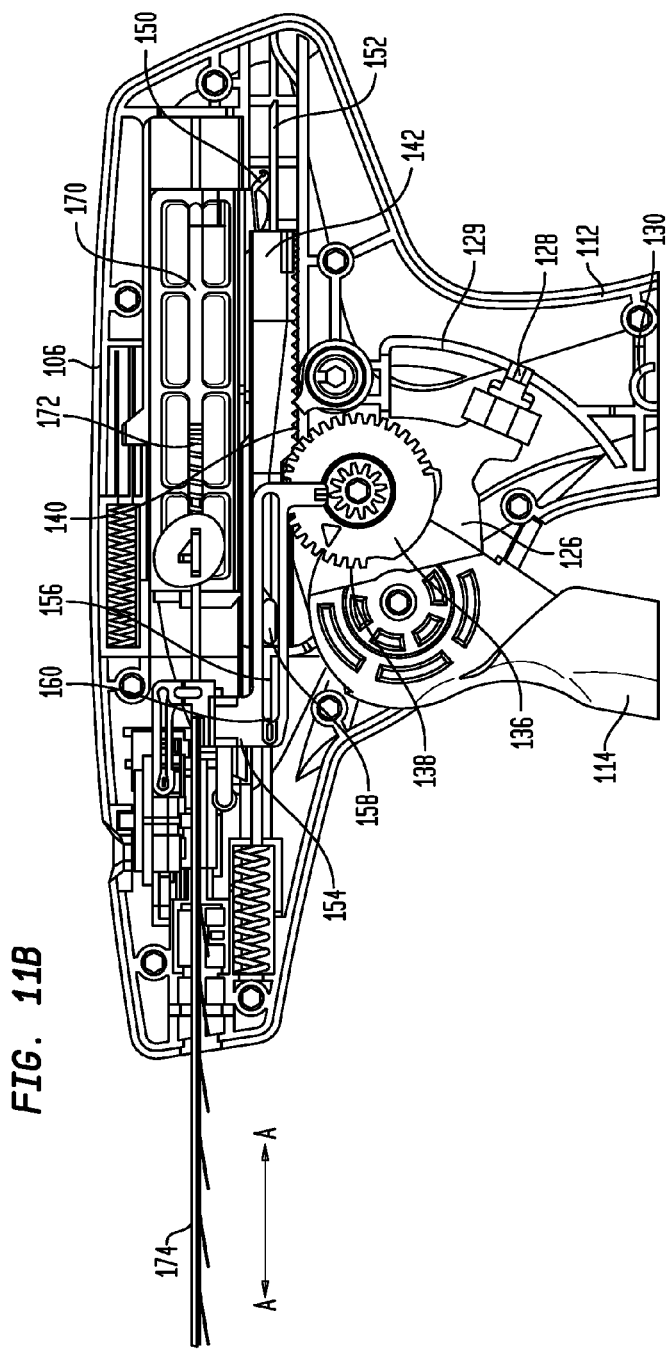
FIGS. 11A-11N show a cross-sectional view of a proximal end of an applicator instrument during stages of a firing cycle, in accordance with one embodiment of the present invention.
Figures 1, 11B:
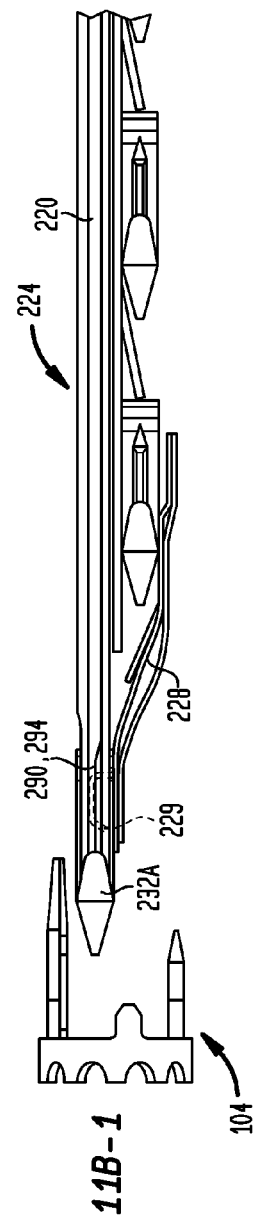
Figure 11F:
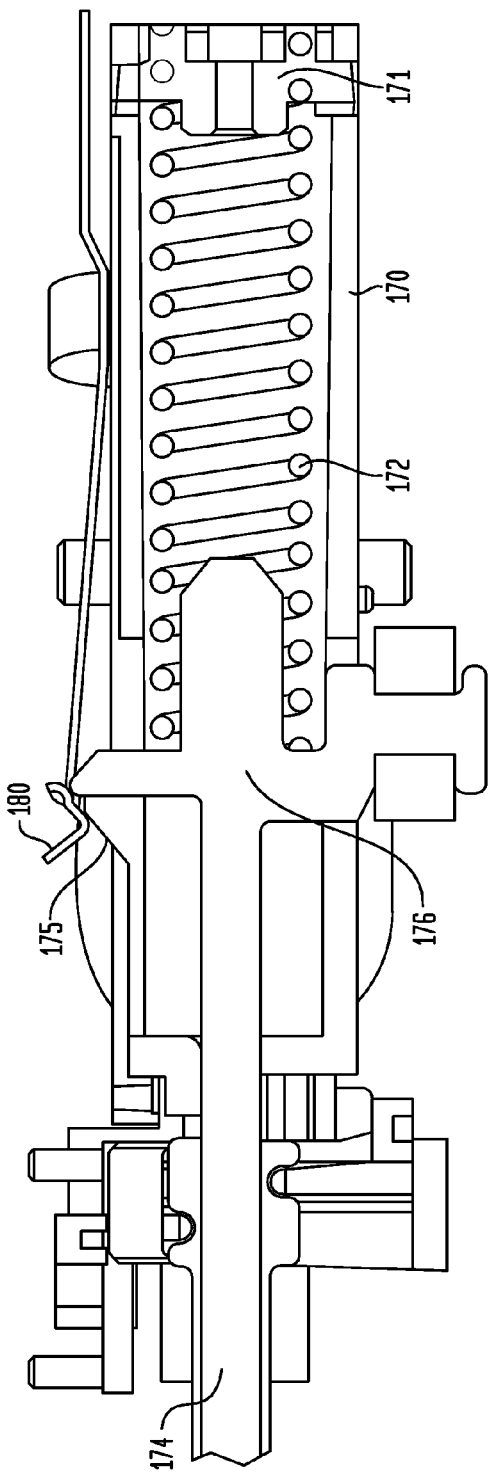
Figures 1, 11F:
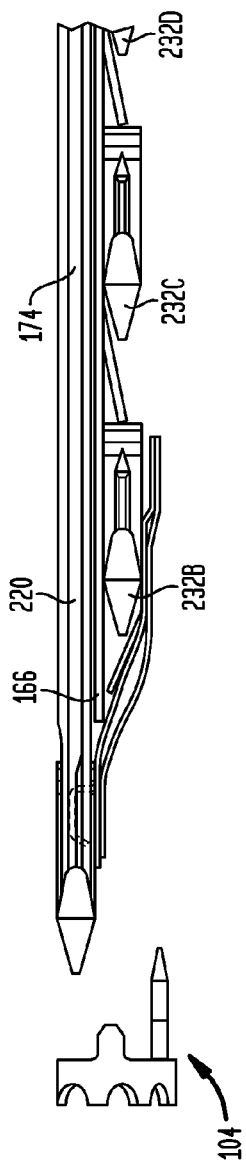
Figure 11H:
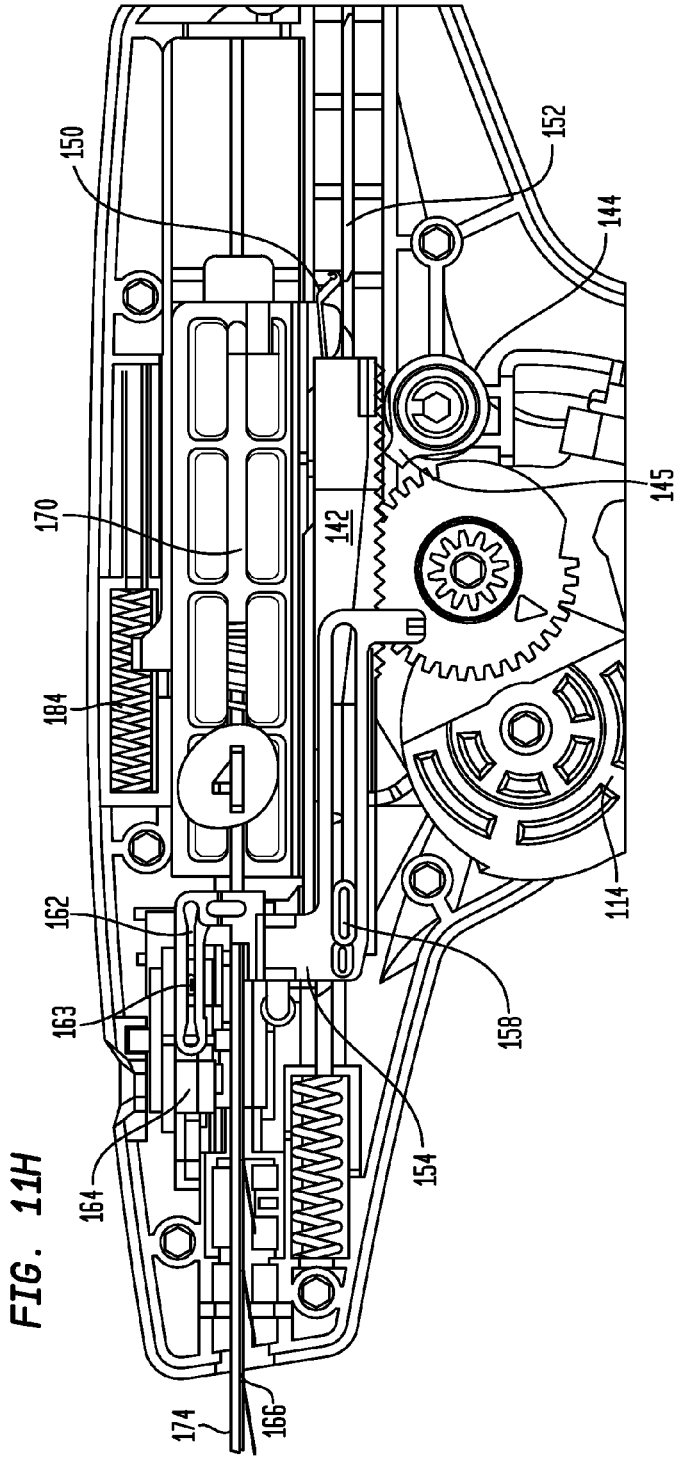
Figures 1, 11H:
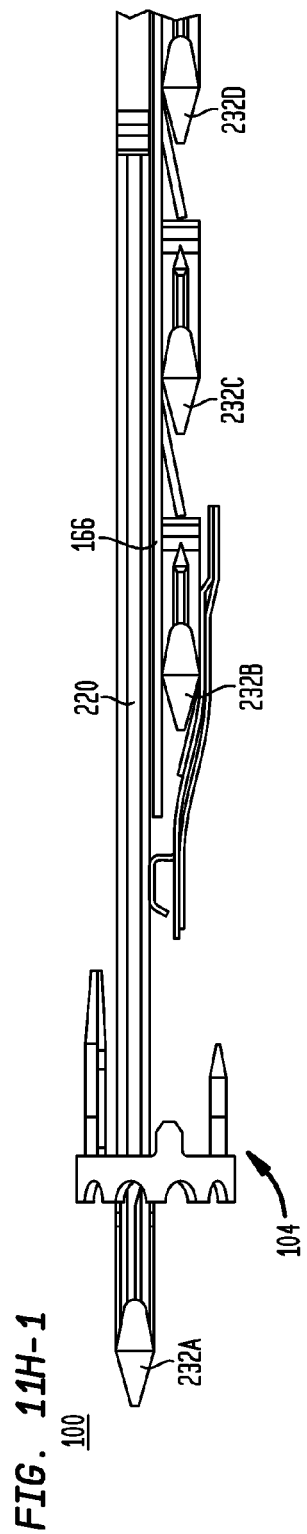
Figure 11I:
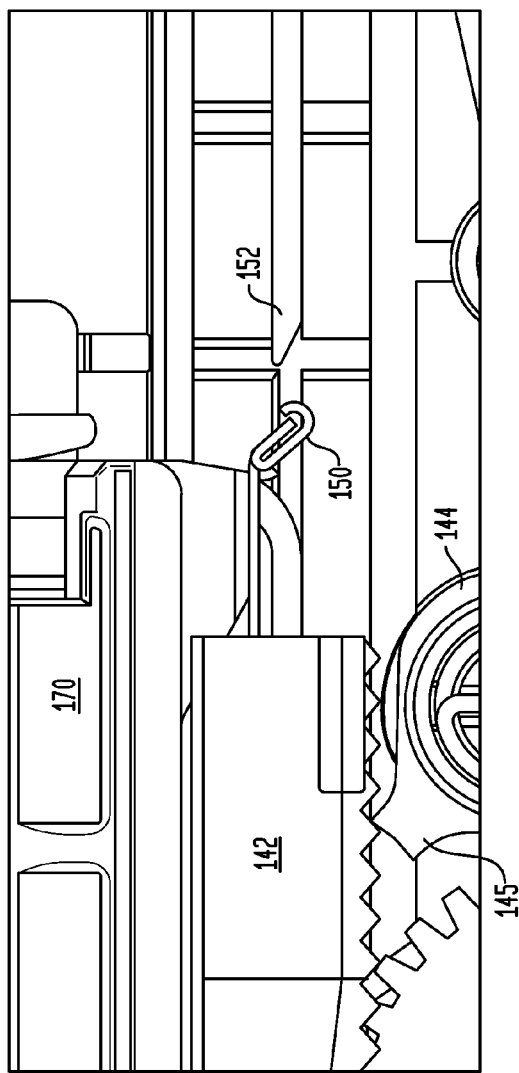
Figures 1, 11I:
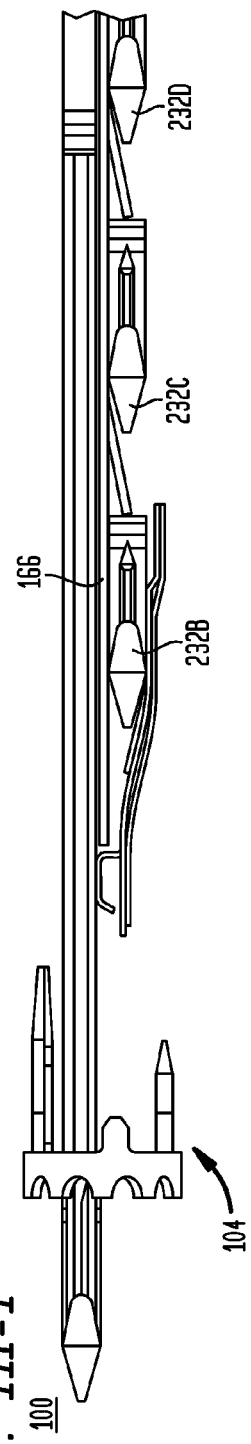
Figure 11K:
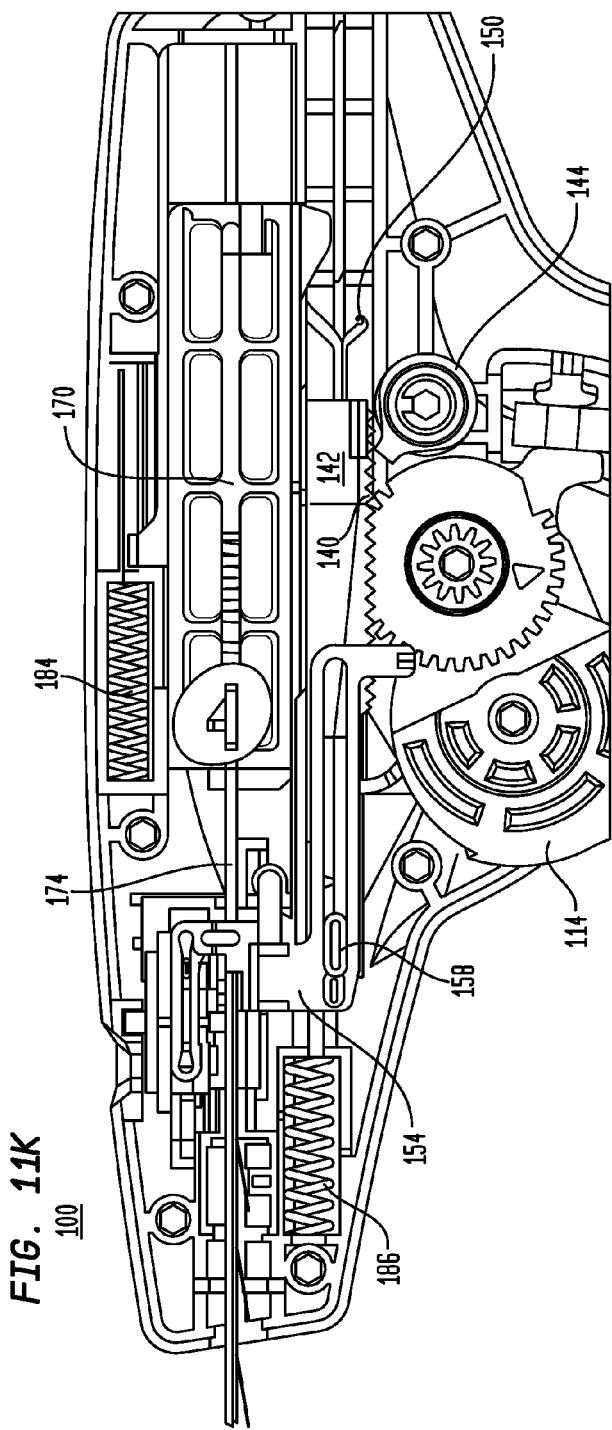
Figures 1, 11K:
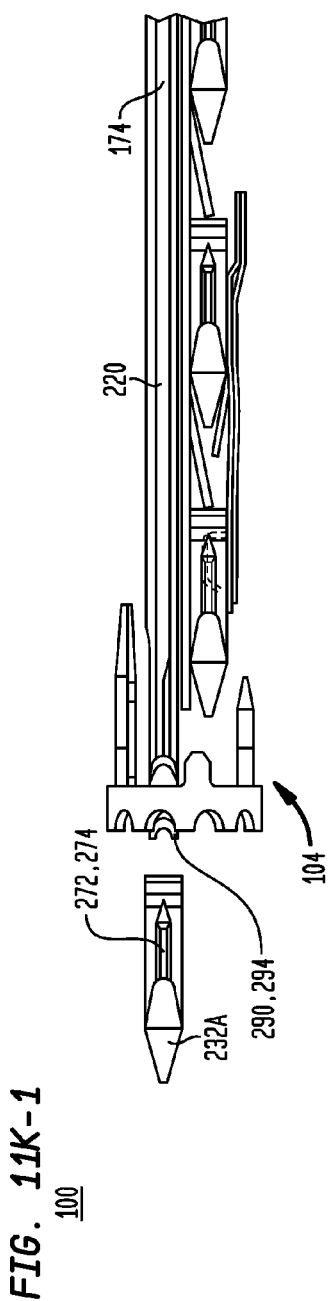
Figure 11L:
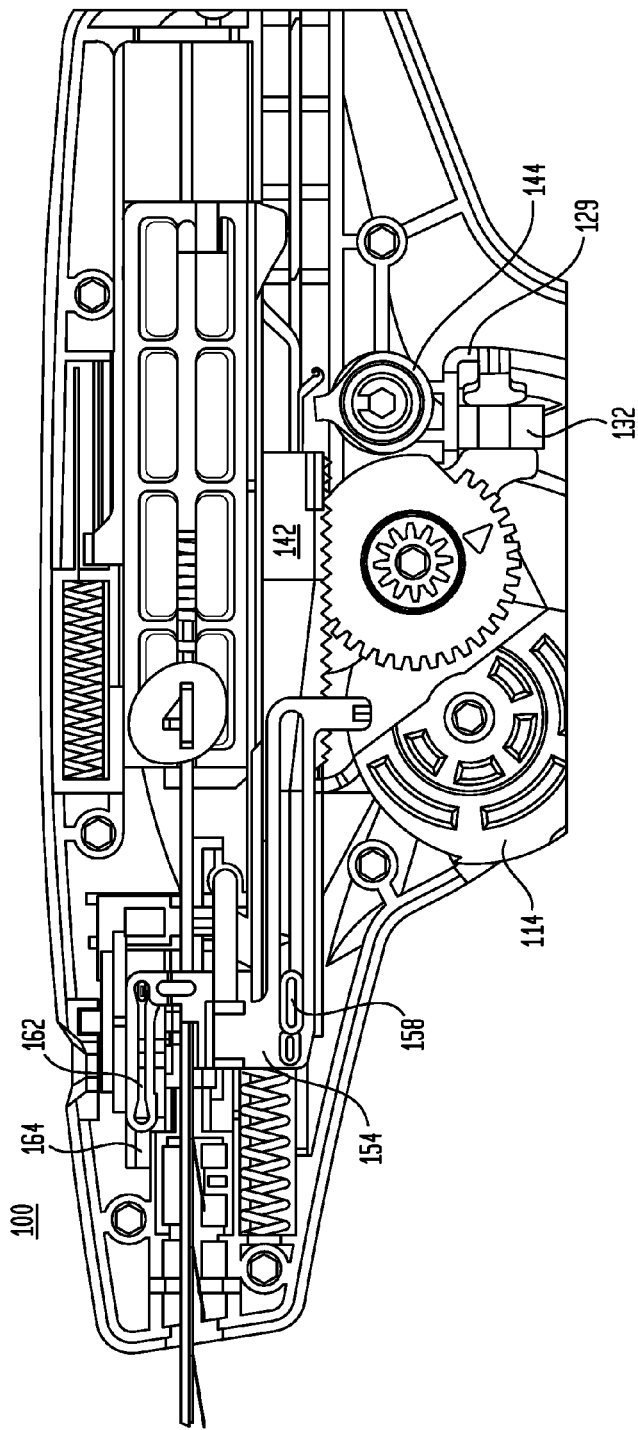
Figures 1, 11L:
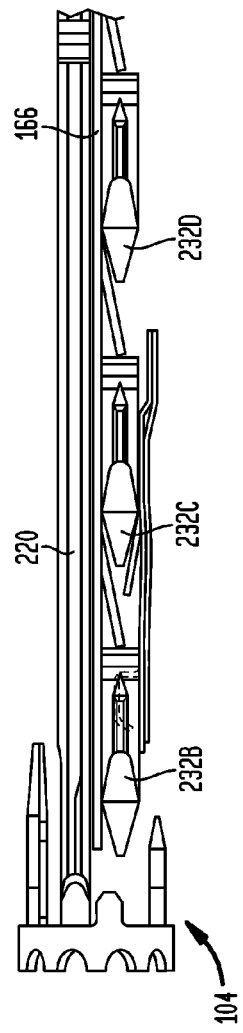
Figure 11M:
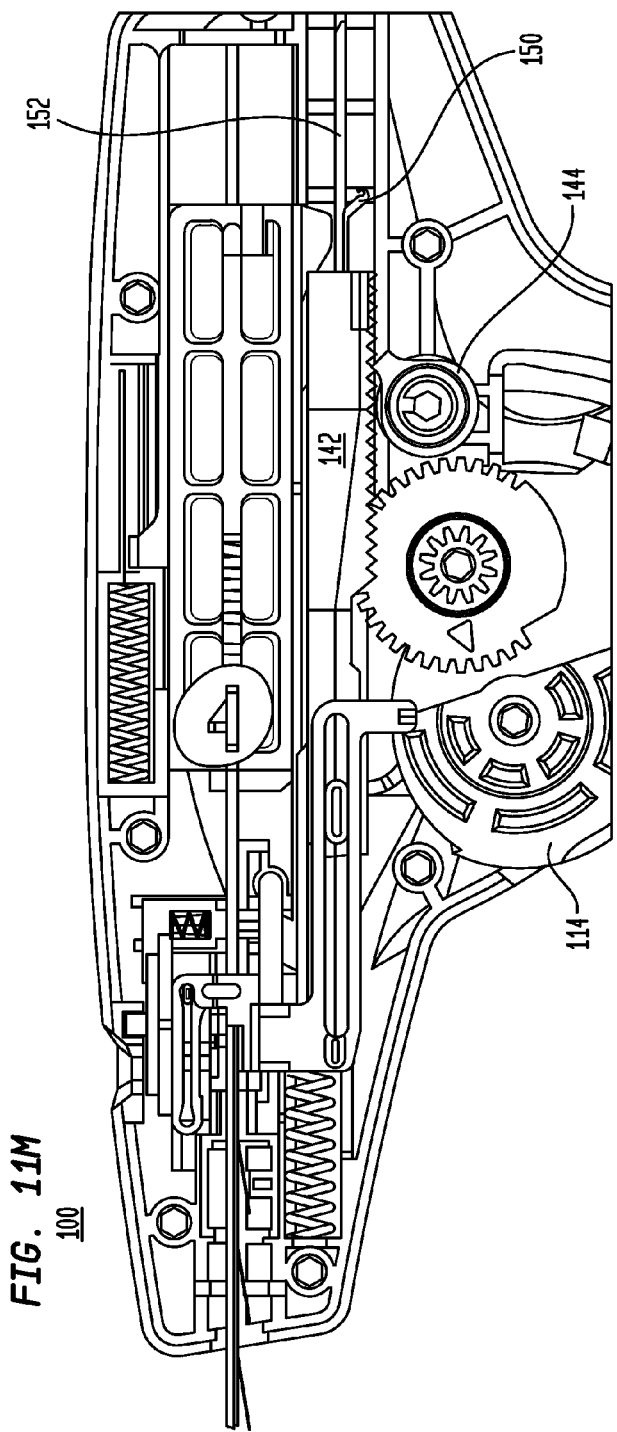
Figures 1, 11M:
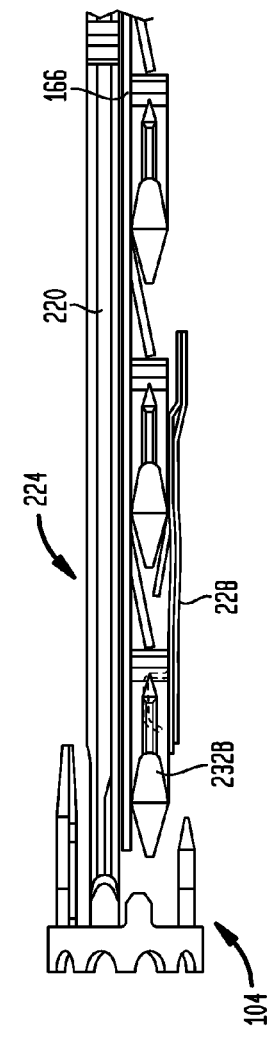
Figure 11N:
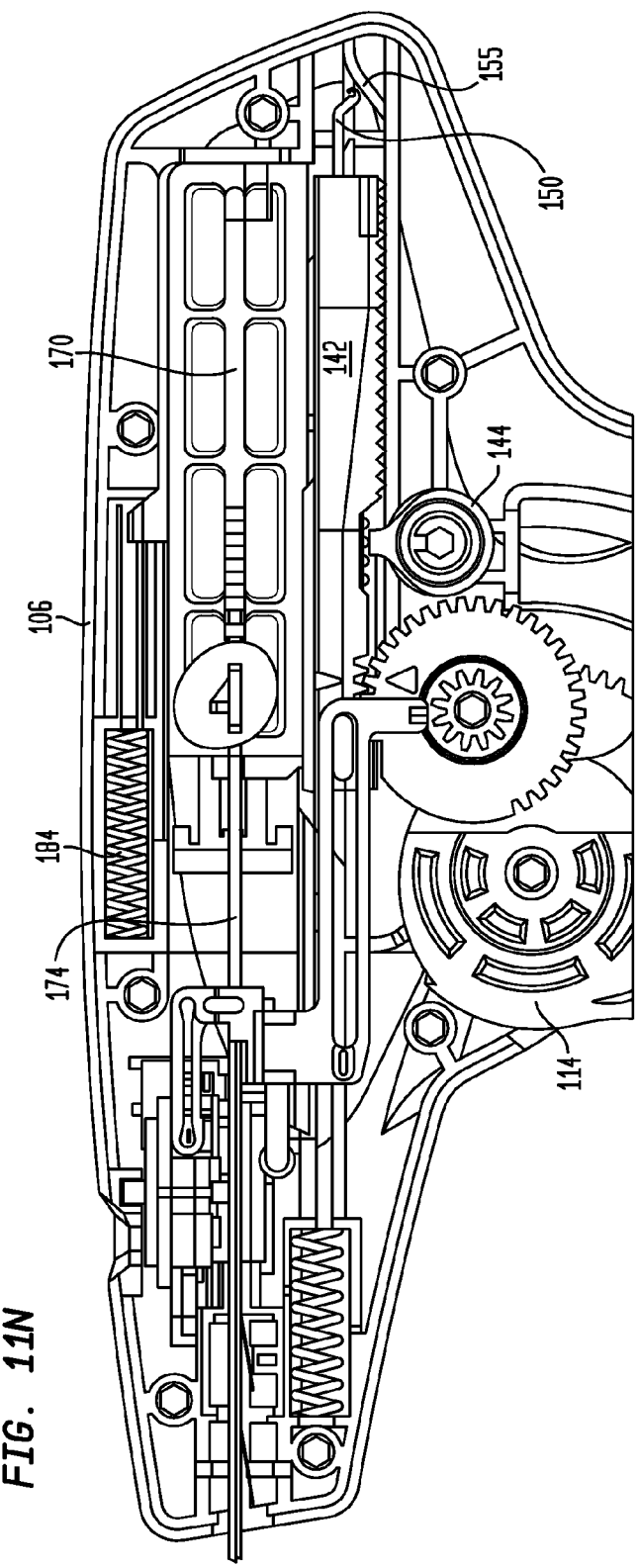
Figures 1, 11N:
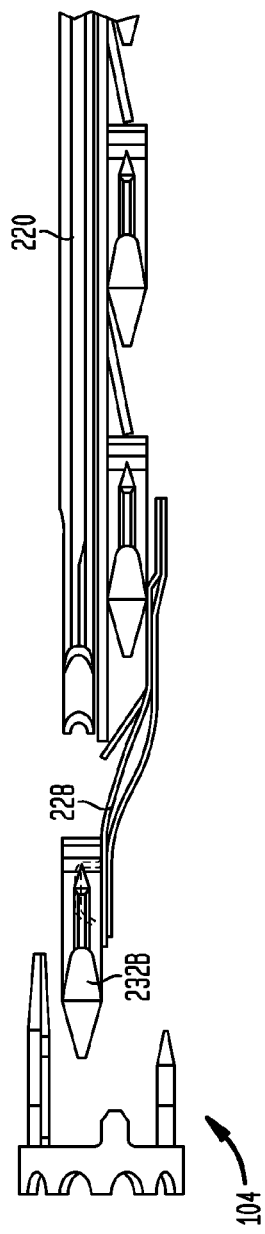

FIGS. 11A-11N show the firing system of the applicator instrument during various stages of a firing cycle. FIGS. 11A-1 through 11N-1 show the distal end of the applicator instrument during the same stages shown in respective FIGS. 11A-11N. For example, FIG. 11A shows the firing system at the start of a firing cycle with the trigger 114 fully open and the firing rod 174 fully retracted. FIG. 11A-1 shows the distal end of the applicator instrument at the same stage as shown in FIG. 11A. FIGS. 11B-11N and FIGS. 11B-1 through 11N-1 follow the same pattern.

Referring to FIG. 11A, in one embodiment, in a first stage of a firing cycle, the trigger 114 is completely open and the trigger gear projection 128 is at the lower end of the trigger guide 129. The yoke 142, the indexer 154, the advancer 166, the spring block 170, and the firing rod 174 are all fully retracted toward the proximal end of the applicator instrument. At the first stage of the firing cycle shown in FIG. 11A, the primary latch 150 is in a neutral position and is de-coupled from the spring block 170. The firing spring 172 is disposed between a proximal end of the spring block 170 and the cruciform-shaped coupling 176 at the proximal end of the firing rod 174. The firing spring 172 extending between the spring block 170 and the firing rod 174 is desirably pre-compressed so that there is an initial distal force (to the left) on the firing rod 174. The firing rod 174 and the advancer 166 project from a distal end of the housing 106 and extend toward a distal end of the applicator instrument 100.

FIG. 11A-1 shows the distal end 104 of the applicator instrument 100 at the first stage of the firing cycle shown in FIG. 11A. The outer tube, the ceiling stamping, and the anti-backup stamping have been removed from the drawing figure to more clearly show the other internal components disposed at the distal end of the applicator instrument. Referring to FIG. 11A-1, the staging leaf support 226 and the staging leaf 228 desirably hold the lead surgical fastener 232A so that the ribs 272, 274 on the outer side walls of the surgical fastener are in alignment with the inner grooves formed in the times 290, 294 at the distal end 224 of the insertion fork 220. The staging leaf tab 129 preferably stabilizes the lead surgical fastener 232A from further distal movement. Additional trailing surgical fasteners 232B, 232C, 232D are positioned behind the lead surgical fastener 232A. Although only four surgical fasteners 232A-232D are shown in FIG. 10A-1, the applicator instrument may carry additional surgical fasteners such as 10, 25, 100 or more surgical fasteners. The advancer 166 includes advancer tabs 230 that are adapted to push the respective surgical fasteners 232B-232D toward the staging leaf assembly at the distal end 104 of the applicator instrument 100. Each time the advancer 166 moves to the left, the surgical fasteners are advanced one position toward the distal end 104 of the applicator instrument 100.

FIG. 11B shows a later stage of the firing cycle during which the tines at the distal end of the insertion fork are piloted into engagement with the ribs on the legs of the lead surgical fastener. During this stage of the firing cycle, the trigger 114 is partially squeezed toward the grip 112 for moving the trigger gear 126 and the trigger gear projection 128 toward the upper end of the trigger guide 129. As the trigger 114 is pulled, the trigger return spring 130 connected to the trigger gear projection 128 is stretched to store potential energy in the spring. As the trigger gear 126 pivots in an upward, counterclockwise direction, the teeth on the trigger gear 126 rotate the drive gear 136 in a counterclockwise direction. The second set of gear teeth 138 on the outer periphery of the drive gear 136 engage the teeth 140 extending along the bottom surface of the yoke 142 for moving the yoke 142 toward the distal end of the applicator instrument (to the left). As the yoke 142 moves toward the distal end of the applicator instrument, the primary latch 150 slides over a top surface of the primary latch raceway 152 for coupling the yoke with the spring block. Because the firing spring 172 is pre-compressed inside the spring block, the firing rod moves distally as the yoke, the spring block and the firing rod move distally as a unit. At this stage, the firing rod moves distally at a rate that is proportional to movement of the trigger.

Referring to FIG. 11B, the yoke 142 is adapted to slide within the housing 106 in distal and proximal directions along the longitudinal axis of the applicator instrument designated A-A. As the yoke 142 moves distally, the yoke boss 158 slides in a distal direction toward the distal end 160 of the lower slot 156 of the indexer 154. As will be described in more detail below, when the yoke boss 158 abuts against the distal end 160 of the lower slot 156 of the indexer 154, the yoke boss 158 will urge the indexer 154 to move distally.

FIG. 11B-1 shows the distal end 104 of the applicator instrument 100 during the stage of the firing cycle shown in FIG. 11B. The prongs 290, 294 at the distal end 224 of the insertion fork 220 are piloted into engagement with the legs of the lead surgical fastener 232A. The insertion fork 220 preferably moves distally at a rate that is proportional to the rate of the trigger squeeze. The staging leaf tab 229 and the staging leaf 228 preferably stabilize the lead surgical fastener 232A as the fork tines 290, 294 are piloted into engagement with the ribs of the lead surgical fastener. The staging leaf tab 229 may engage the inner surface of the outer tube to provide stability.

FIG. 11C shows the firing system after the insertion fork has been piloted onto the legs of the surgical fastener. In FIG. 11C, the distal end of the firing system is to the right and the proximal end of the firing system is to the left. At about the same time or after the insertion fork has been piloted distally for engaging the lead surgical fastener, a firing spring latch 180 engages the cruciform-shaped end 176 of the firing rod 174. Upon the engagement, the firing spring latch 180 prevents further distal movement of the firing rod 174. Up to this point in time, the firing rod has moved as a unit with the spring block 170, due to the pre-load on the firing spring within the spring block. Once the firing spring latch 180 engages the cruciform-shaped end 176, the firing rod cannot continue to move distally. As a user continues to squeeze the trigger 114, the firing rod 174 cannot move further distally and the firing spring is compressed.

FIG. 11C-1 shows the distal end 104 of the applicator instrument 100 during the stage shown in FIG. 11C. After the distal end of the insertion fork 220 has been advanced into contact with the lead surgical fastener 232A, the firing spring latch 180 holds the firing rod 174 from further distal movement. Thus, after the distal end of the insertion fork has been piloted into contact with the lead surgical fastener, and until the applicator instrument "fires" the surgical fastener from the distal end, the firing rod does not have any further distal movement as the trigger continues to be pulled toward the fully closed position for storing potential energy in the firing spring.

FIG. 11D shows a top cross-sectional view of a portion of the firing system during the same stage of the firing cycle shown in FIG. 11C. The firing system includes the firing rod 174, the cruciform-shaped structure 176 at the proximal end of the firing rod 174, the firing spring 172 and the spring block 170 containing the firing spring 172. In FIG. 11D, the distal end of the applicator instrument is to the left and the proximal end of the applicator instrument is to the right. As shown in FIG. 11D, as the trigger is pulled, the spring block 172 is urged toward the distal end of the applicator instrument by the primary latch (not shown). Distal movement of the spring block 170 compresses the firing spring 172 between the cruciform-shaped structure 176 at the proximal end of the firing rod 174 and the proximal end of the spring block 170. As noted above, during this stage, the firing rod 174 is constrained from further distal movement by the firing spring latch 180 engaging the cruciform-shaped structure 176 of the firing rod 174. FIG. 11D-1 shows the distal end 104 of the applicator instrument during the stage shown in FIG. 11D. As noted above, although the tines of the insertion fork 220 have been piloted around the sides of the lead surgical fastener 232A, the firing spring latch prevents further distal movement of the firing rod 174 and the insertion fork 220.

FIG. 11E shows the firing system during a later stage of the firing cycle. The user preferably continues to squeeze the trigger 114 toward the closed position. During this stage, the yoke 142 moves further distally until the yoke boss 158 engages the distal end 160 of the lower slot 156 of the indexer 154. Once the yoke boss 158 contacts the distal end 160 of the lower slot 156, further distal movement of the yoke 142 urges the indexer 154 in a distal direction, which, in turn, urges the advancer 166 to move distally for advancing surgical fasteners. The indexer and the advancer preferably move together as a unit.

As the user continues to squeeze the trigger 114, the yoke 142 continues to move distally, taking the spring block 170 with it in a distal direction via the coupling of the primary latch 150 with the spring block 170. The firing rod 174 continues to be held back from further distal movement by the firing rod latch (FIG. 11D). As the spring block 170 moves distally, additional energy is stored in the firing spring 172 disposed within the spring block. Because it has been compressed, the firing spring is shorter than its original length with its right side disposed inside the proximal end of the spring block 170. As the spring block 170 moves distally (to the left), the spring block return spring 184 is compressed. In one embodiment, a flange extending from the spring block 170 engages the spring block return spring 184 for storing energy in the spring block return spring.

FIG. 11E-1 shows the distal end 104 of the applicator instrument 100 during the stage shown in FIG. 11E. As the indexer 154 (FIG. 11E) is moved distally by the yoke boss 158, the indexer 154 urges the advancer 166 to move in a distal direction, which advances the trailing surgical fasteners 232B, 232C and 232D toward the distal end of the applicator instrument. There is no further distal movement of the lead surgical fastener 232A at this stage.

FIG. 11F shows a top cross-sectional view of the firing system at a later stage of the firing cycle that occurs just before the firing rod 174 is released. In one embodiment, the spring block 170 includes a firing spring release ramp 175 projecting from a surface thereof. The firing spring release ramp 175 is preferably aligned with the firing spring release latch 180. As the spring block 170 moves toward the distal end of the applicator instrument (to the left), the ramp 175 engages the firing spring release latch 180 for de-coupling the release latch 180 from the cruciform-shaped end 176 at the proximal end of the firing rod 174. Once the release latch is de-coupled from the cruciform-shaped end 176 of the firing rod, the firing rod 174 is free to move distally. The energy stored in the firing spring 172 is now released to the firing rod 174.

FIG. 11F-1 shows the distal end 104 of the applicator instrument 100 during the stage of the firing cycle shown in FIG. 11F. During this stage, the firing spring release latch 180 is about to be released from engagement with the cruciform-shaped end 176 of the firing rod. The advancer 166 has moved distally for advancing the trailing surgical fasteners 232B-232D toward the distal end 104 of the applicator instrument 100.

FIG. 11G shows a later stage of the firing cycle during which the firing rod is released for rapidly advancing the insertion fork toward the distal end of the applicator instrument. During this stage, the firing spring release ramp 175 pushes the firing spring release latch 180 away from engagement with the cruciform-shaped structure 176. The firing rod 174, unconstrained from distal movement, is rapidly advanced toward the distal end of the applicator instrument by the firing spring 172. The firing spring 172 moves the firing rod 174 distally until the firing rod dampening pad 178 engages a stop wall SW in the housing. The firing rod dampening pad 178 may be compressed slightly until the positive stop 179 on the cruciform-shaped structure 176 engages the stop wall SW for halting all further distal movement of the firing rod. Although the present invention is not limited by any particular theory of operation, it is believed that the firing rod dampening pad 176 lengthens the time period for deceleration of the firing rod 174 so as to stop the firing rod over a longer period of time. The lengthening of the deceleration period of the firing rod preferably decreases the impact force transmitted to a user, and also desirably reduces noise.

FIG. 11G-1 shows the distal end 104 of the applicator instrument during the stage of the firing cycle shown in FIG. 11G. The firing rod 174 and the insertion fork 220 have been rapidly advanced distally (to the left) by the firing spring. The lead surgical fastener 232A is shot from the distal end 104 of the applicator instrument 100 for securing a prosthetic device (e.g. a mesh) to tissue. As shown in FIG. 11G-1, at a distal-most position, the distal end 224 of the insertion fork 220 has advanced beyond the distal end of the end cap 122.

Referring to FIGS. 11G and 11G-1, the engagement of the positive stop 179 with the stop wall SW (FIG. 11G) limits further distal movement of the insertion fork 220. Thus, the combination of the firing rod dampening pad 178, the positive stop 179 and the stop wall SW limit the maximum expulsion of the lead surgical fastener 232A and the insertion fork from the applicator instrument. It has been observed that excessive expulsion of a surgical fastener and/or insertion fork from a distal end of an applicator instrument may damage a prosthetic device or injure tissue. In one embodiment, during the stage of the firing cycle shown in FIGS. 11G and 11G-1, the trailing surgical fasteners 232B-232D do not move distally.

Referring to FIG. 11H, in one embodiment, after the lead surgical fastener 232A has been dispensed, the firing cycle is not complete and the trigger cannot return to the fully open position shown in FIG. 11A. In one embodiment, during this stage of the firing cycle, the trigger 114 must be further squeezed for advancing the yoke 142 further toward the distal end of the applicator instrument. In one embodiment, the ratchet pawl 144 engaging the teeth on the underside of the yoke 142 prevents the yoke 142 from changing direction to move proximally until the projection 145 on the ratchet pawl 144 clears the proximal end of the yoke 142. If an operator stops pulling the trigger before the projection 145 on the ratchet pawl 144 clears the proximal end of the yoke 142, the trigger 114 freezes in position and will not return to the fully open position. Thus, an operator must continue to pull the trigger, which continues to move the yoke toward the distal end of the applicator instrument. As the yoke 142 continues to move distally, the yoke boss 158 moves the indexer 154 distally, which results in distal movement of the advancer 166 for advancing the surgical fasteners. As the indexer moves distally, the upper slot 162 of the indexer 154 also preferably engages a tab 163 on the lockout counter 164 for at least partially rotating a lockout indicator, as will be described in more detail below.

Referring to FIG. 11H, as the yoke 142 moves distally, the primary latch 150 approaches a distal opening in the primary latch raceway 152. Once the primary latch 150 reaches the distal opening of the primary latch raceway 152, the primary latch 150 is free to drop for de-coupling the yoke 142 from the spring block 170. After de-coupling, the spring block 170 is free to move independently of the yoke. In one embodiment, the de-coupled spring block will move toward the proximal end of the applicator instrument in response to forces provided by the spring block return spring 184.

FIG. 11H-1 shows the distal end 104 of the applicator instrument 100 during the stage of the firing cycle shown in FIG. 11H. The insertion fork 220 cannot move further distally due to the stop wall SW in the handle engaging the positive stop on the cruciform-shaped end of the firing rod. Further distal movement of the yoke 142, however, continues to move the indexer 154 to the left, which, in turn, moves the advancer 166 in a distal direction to advance the trailing surgical fasteners 232B, 232C and 232D toward the distal end 104 of the applicator instrument 100.

FIG. 11I shows the primary latch 150 after it has reached the distal opening in the primary latch racetrack 152. Once the primary latch 150 reaches the distal opening, the primary latch 150 is free to drop for de-coupling the yoke 152 from the spring block 170. Once the primary latch 150 de-couples the yoke 142 from the spring block 170, the spring block 170 and the yoke 152 move independently of one another. Referring to FIG. 11I, as noted above, the yoke 152 is constrained from proximal movement until the projection 145 on the ratchet pawl 146 clears the right end of the yoke 152.

FIG. 11I-1 shows the distal end 104 of the applicator instrument 100 after the primary latch 150 has been de-coupled from the spring block 170. As the trigger continues to be compressed, the advancer 166 continues to move distally for advancing the surgical fasteners 232B, 232C and 232D in a distal direction.

Referring to FIG. 11J, as the trigger 114 continues to be compressed, the yoke 142 continues to advance the indexer 154 distally. Further distal movement of the indexer 154 moves the advancer 166 distally and moves the tab 163 on the lockout counter 164 distally. The tab 163 of the lockout counter 164 preferably frictionally engages the upper slot 162 of the indexer 154. FIG. 11J-1 shows the distal end 104 of the applicator instrument 100 during the stage of the firing cycle shown in FIG. 11J.

Referring to FIG. 11K, in one embodiment, after the primary latch 150 has de-coupled from the spring block, the spring block return spring 184 urges the spring block 170 to move proximally. As the spring block 170 moves to the right, the spring block 170 pulls the firing rod 174 toward the proximal end of the applicator instrument 100. Thus, the spring block 170 and the firing rod 174 move as a unit toward the proximal end of the applicator instrument while the yoke 142 continues to move toward the distal end of the instrument under the force of the trigger 114. In one embodiment, the yoke boss 158 continues to move the indexer 154 distally for compressing the dampening spring 186. In one embodiment, the dampening spring 186 desirably gradually slows the user's compression of the trigger when the indexer 154 pushes against it.

FIG. 11K-1 shows the distal end 104 of the applicator instrument 100 during the stage shown in FIG. 11K. After the primary latch releases the spring block from the yoke, the spring block moves to the right, thereby retracting the firing rod 174 and the insertion fork 220. As shown in FIG. 11K-1, the lead surgical fastener 232A remains implanted in tissue, while the tines 290, 294 have been retracted from the ribs 272, 274 on the lead surgical fastener.

Referring to FIG. 11L, once the trigger 114 is fully compressed, the right end of the yoke 142 clears the ratchet pawl 144. As a result, the yoke 142 is now free to move in a proximal direction. When the trigger 114 is fully squeezed, the yoke boss 158 preferably urges the indexer 154 into a distal-most position. In turn, the upper slot 162 of the indexer has preferably advanced the lockout counter 164 one-half of a cycle. With the trigger in the fully compressed position, the trigger dampening pad 132 engages an end wall of the trigger guide 129 for dampening deceleration of the trigger.

FIG. 11L-1 shows the distal end 104 of the applicator instrument 100 during the stage of the firing cycle shown in FIG. 11L. Distal movement of the indexer results in distal movement of the advancer 166. In one embodiment, as the trigger is squeezed to the fully closed position, the second surgical fastener 232B is advanced to the lead surgical fastener position, the third surgical fastener 232C is advanced to the first trailing position, and the fourth surgical fastener 232D is advanced to the second trailing position. In the stage of the firing cycle shown in FIG. 11L-1, the staging leaf 228 is preferably deflected downwardly by the extended insertion fork 220 and the extended advancer 166. When the trigger begins moving into the uncompressed, open position, the advancer 166 and the insertion fork 220 are retracted, which enables the lead surgical fastener 232B to be moved by the staging leaf 228 into alignment with the tines of the insertion fork.

Referring to FIG. 11M, in one embodiment, as the trigger 114 rotates back to the open, uncompressed position, the yoke 142 moves in a proximal direction. At this stage, the ratchet pawl 144 prevents the yoke 142 from changing direction until the yoke reaches a fully retracted position. As the yoke 142 moves proximally, the primary latch 150 moves below the primary latch racetrack 152.

FIG. 11M-1 shows the distal end 104 of the applicator instrument 100 during the stage of the firing cycle shown in FIG. 11M. The new lead surgical fastener 232B sits below the extended advancer 166 and the partially extended insertion fork 220. The staging leaf 228 and the staging leaf support 226 remain deflected in a downward position by the extended advancer and the extender insertion fork. The staging leaf 228 is constrained from springing into an upright position due to being blocked by the advancer 166 and the insertion fork 220.

Referring to FIG. 11N, in one embodiment, the spring block return spring 184 returns the spring block 170 to its initial proximal position. In turn, proximal movement of the spring block 150 retracts the firing rod 174 and the insertion fork at the distal end of the applicator instrument. As the trigger moves to the fully open position, the yoke 142 also reaches a proximal-most position. As the yoke 142 reaches the proximal end of its range, the primary latch 150 is urged upwardly by a primary latch ramp 155 located adjacent a proximal end of the housing 106. With the yoke 142 in a retracted position, the ratchet pawl 144 moves into a neutral position under the yoke 142. At this stage, the yoke 142 is free to move distally and will not be constrained from distal movement by the ratchet pawl 144.

FIG. 11N-1 shows the distal end 104 of the applicator instrument during the final stage of the firing cycle shown in FIG. 11N. As shown in FIG. 11N-1, the advancer 166 and the insertion fork 220 are fully retracted, thereby enabling the staging leaf 228 to deflect upwardly for aligning the lead surgical fastener 232B with the tines of the insertion fork 220.

In one embodiment, the applicator instrument of the present invention may be used to repair of a defect, such as an inguinal hernia, located in inguinal tissue such as the inguinal floor. Generally, an inguinal hernia may be accessed through the iliacus muscle. As can be well appreciated, a network of vessels and nerves exist in the area of a typical inguinal hernia, which requires a surgeon to conduct a hernia repair with great skill and caution. For instance, in the transverse abdominis aponeurosis, an internal ring permits gastric vessels and Vas deferens to extend therethrough over an edge of inguinal ligament. A femoral canal is located near the Cooper's ligament and contains external iliac vessels and inferior epigastric vessels.

In many cases, the edge of the inguinal ligament and the Cooper's ligament serve as anatomical landmarks and support structures for supporting surgical fasteners such as those mentioned previously. The area containing the external iliac vessels and the Vas deferens may be commonly known as "the Triangle of Doom" to surgeons. Accordingly, care must be taken when performing dissection, suturing or fastening within this area.

A prosthetic or a mesh patch may be placed over the inguinal hernia. The mesh patch may have any desired configuration, structure or material. In one embodiment, the mesh patch may be made of PROLENE™ (a well-known polymer made of fibers) and preferably configured as mesh.

The mesh patch may be placed over the inguinal hernia for providing a sufficient barrier to internal viscera (not shown) of the abdomen which would otherwise have a tendency to protrude through the inguinal hernia and cause the patient a great deal of pain and discomfort. After the mesh patch has been placed onto the inguinal floor, the mesh patch is ready for attachment to the inguinal floor.

Referring FIG. 12A-12D, in one embodiment, a distal end 104 of an applicator instrument 100 is positioned over a prosthetic device 270 for securing a prosthetic device, such as a mesh patch, to tissue T. The prosthetic device may be a surgical mesh having strands 272 extending therethrough. The tips of each surgical fastener are preferably spaced from one another to increase the chances that the surgical fastener will engage at least one of the strands 272. The distal end 104 of the instrument 100 preferably includes an end cap 122 having castling 242 that facilitates holding the instrument in place over the prosthetic device 270.

Referring to FIG. 12A, the applicator instrument 100 preferably includes an outer tube 116 surrounding a ceiling stamping 200 and an anti-backup stamping 208. The end cap 122 is coupled with the outer tube 116, the ceiling stamping 200 and the anti-backup stamping 208. The ceiling stamping desirably has one or more ceiling stamping spring tabs 202 for pressing against the inner surface of the outer tube 116 to provide a snug fit between the inner stampings 200, 208 and the outer tube 116. The applicator instrument includes the insertion fork 220 having tines projecting from the distal end thereof. One of the tines 294 has an inner groove 296 that extends along the longitudinal axis A-A of the applicator instrument for engaging a rib on a leg of the surgical fastener. The applicator instrument includes the staging leaf assembly including the staging leaf support 226 and the staging leaf 228 for holding the surgical fasteners in alignment with the tines 294 of the insertion fork 220.

The advancer 166 is preferably disposed between the insertion fork and the anti-backup stamping. The advancer 166 includes advancer tabs 230 for urging the surgical fasteners toward the distal end of the applicator instrument. The anti-backup stamping has anti-backup tabs 212 that prevent the surgical fasteners from moving proximally.

In FIG. 12A, the firing system is positioned at a first stage of a firing cycle. The insertion fork 220 and the advancer 166 are retracted and the staging leaf assembly holds the lead surgical fastener 232A in alignment with the at least one tine 294 of the insertion fork 220.

FIG. 12B shows a later stage of the firing cycle when the at least one tine 294 of the insertion fork has been piloted distally to engage the ribs on the lead surgical fastener 232A. During piloting, the insertion fork 220 moves distally at a rate that is proportional to the rate that the trigger is squeezed. During piloting, the staging leaf tab 229 and the staging leaf 228 stabilize and hold the lead surgical fastener 232A from further distal movement.

In FIG. 12C, after potential energy has been stored in the firing spring, the firing rod 174 is released for dispensing the lead surgical fastener 232A from the applicator instrument 100. The firing rod drives the insertion fork 220, which, in turn, drives the lead surgical fastener 232A through the prosthetic device for implanting the tips of the surgical fastener in the tissue T for anchoring the prosthetic device to the tissue T. During implantation into tissue, the tines of the insertion fork preferably support the lead surgical fastener 232A to prevent the lead surgical fastener from bending or twisting. As the insertion fork 220 and the firing rod 174 drive the lead surgical fastener 232A into the prosthetic device and the tissue T, the trailing surgical fastener 232B preferably remains stationary.

Referring to FIG. 12D, in one embodiment, during a later stage of the firing cycle, the trigger is pulled further for advancing the advancer 166 toward the distal end of the applicator instrument 100. The advancer tab 230 on the advancer 166 preferably engages the trailing surgical fastener 232B for moving the trailing surgical fastener 232B distally. During this stage, the firing rod is decoupled from the yoke so that the insertion fork 220 is free to retract and disengage from the dispensed surgical fastener 232A.

Referring to FIG. 12E, when the trigger is fully closed, the trailing surgical fastener 232B has been advanced to a staging position by the advancer 166. The staging leaf assembly is constrained from moving the second surgical fastener 232B into alignment with the tines at the end of the insertion fork 220 because it blocked from such movement by the extended advancer 166 and the at least partially extended insertion fork 220.

During a later stage not shown in FIG. 12E, the trigger returns to the open position and the advancer and the insertion fork move proximally to the positions shown in FIG. 12A. When the advancer 166 and the insertion fork 220 are retracted to the initial position shown in FIG. 12A, the staging leaf assembly is free to move the second surgical fastener 232B into alignment with the at least one tine 294 of the insertion fork 220. The applicator instrument is now ready to commence a second firing cycle during which the second surgical fastener 232B will be dispensed from the applicator instrument for being implanted in the prosthetic device 270 and the tissue T.

In one embodiment, the applicator instrument includes a lockout indicator system that locks the applicator instrument from further deployment of surgical fasteners after all of the surgical fasteners have been dispensed. Referring to FIG. 13A, in one embodiment, the lockout indicator system preferably includes a lockout counter 364 having a lockout counter boss 365. The lockout counter preferably moves in distal and proximal directions along the longitudinal axis A-A of the applicator instrument. The lockout counter boss 365 is preferably aligned with the upper slot 362 of the indexer 354 so that the upper slot 362 is capable of sliding over the lockout counter boss 365. In one embodiment, the lockout counter boss 365 has an outer dimension adapted to slide within the upper slot 362 of the indexer 154, however, there is preferably frictional contact between the lockout counter boss 365 and the upper slot 362 as the lockout counter boss moves through the upper slot 362.

In one embodiment, as the trigger of the applicator instrument is pulled, the yoke moves distally, which, in turn, moves the indexer 354 distally (to the left). Referring to FIG. 13B, as the indexer 354 moves distally, the upper slot 362 of the indexer 354 slides over the lockout counter boss 365 of the lockout counter 364. The frictional engagement between the upper slot 362 and the lockout counter boss 365 moves the lockout counter 364 distally, which, in turn, rotates the lockout indicator 375 in a counterclockwise direction.

Figure 14A:
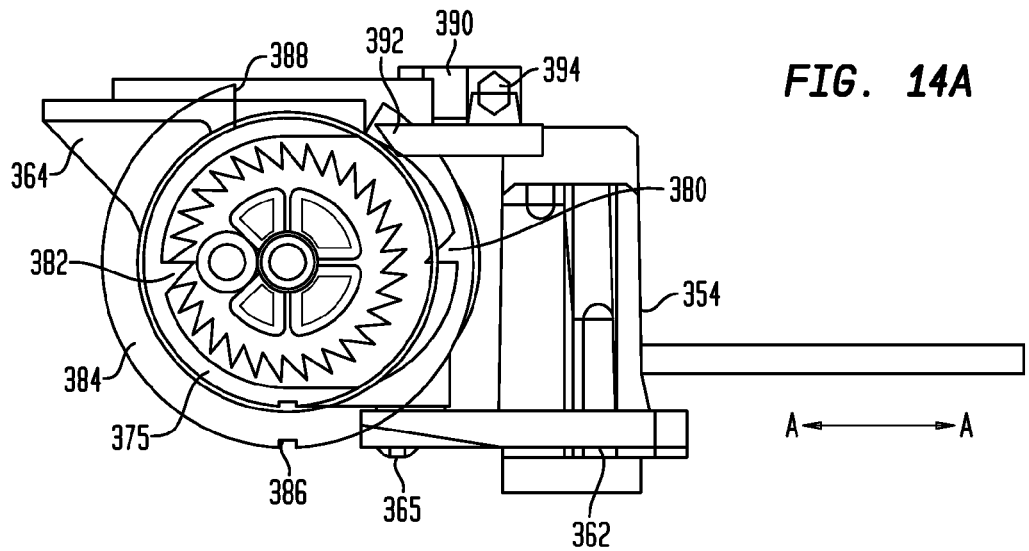
FIGS. 14A-14E show a top plan view of the lockout system of FIGS. 13A and 13B, in accordance with one embodiment of the present invention.

FIGS. 14A-E show a lockout indicator system, in accordance with one embodiment of the invention. The components surrounding the lockout indicator system have been removed to simplify the description of the embodiment. Referring to FIG. 14A, the lockout indicator system desirably includes the lockout counter 364 having the lockout counter boss 365. The lockout counter 364 includes a first tooth 380 adjacent a proximal end of the lockout counter and a second tooth 382 adjacent a leading of the lockout counter. As noted herein, the lockout counter 364 is adapted to move distally and proximally along the longitudinal axis A-A of the applicator instrument.

The lockout indicator system includes a lockout indicator 375 having a main ledge 384 with an alignment notch 386 and a lockout notch 388. The alignment notch 386 desirably is utilized for properly aligning the lockout indicator 375 during initial assembly of the lockout indicator system. The lockout notch 388 provides a larger opening in the main ledge 384 that enables a lockout pin to drop therein for locking the firing system.

In one embodiment, the lockout indicator system includes a lock-put pin 390 having a lockout flange 392 that engages the main ledge 384 of the lockout indicator, and a lockout pin spring 394 that urges the lockout pin 390 in a downward direction once the lockout flange 392 is aligned with the lockout slot 388.

Figure 14B:
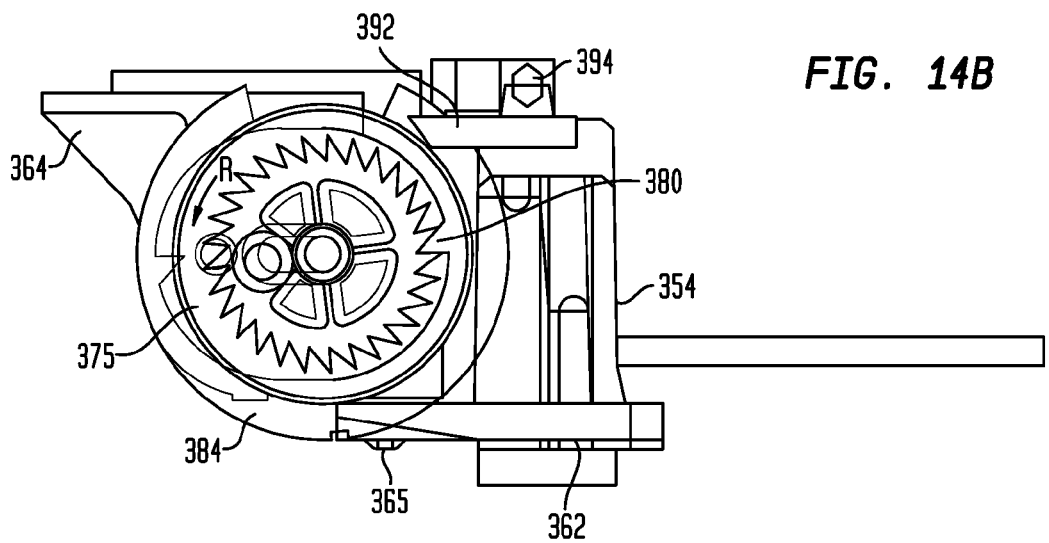

Referring FIG. 14B, as the indexer 354 moves toward the distal end of the applicator instrument (to the left in FIG. 14B), the upper slot 362 moves the lockout counter boss 365 distally, which, in turn, moves the lockout counter 364 distally. As the lockout counter 364 moves distally, the first tooth 380 adjacent the proximal end of the lockout counter 364 engages teeth on the underside of the lockout indicator 375. The engagement of the first tooth 380 of the lockout counter 364 with the teeth on the underside of the lockout indicator 375 rotates the lockout indicator in a counterclockwise direction designated $R_1$. As the lockout indicator 375 rotates in a counterclockwise direction, the lockout flange 392 slides over the main ledge 384 of the lockout counter 375. As long as the lockout flange 292 is in contact with the main ledge 384, the lockout pin cannot drop.

Figure 14C:
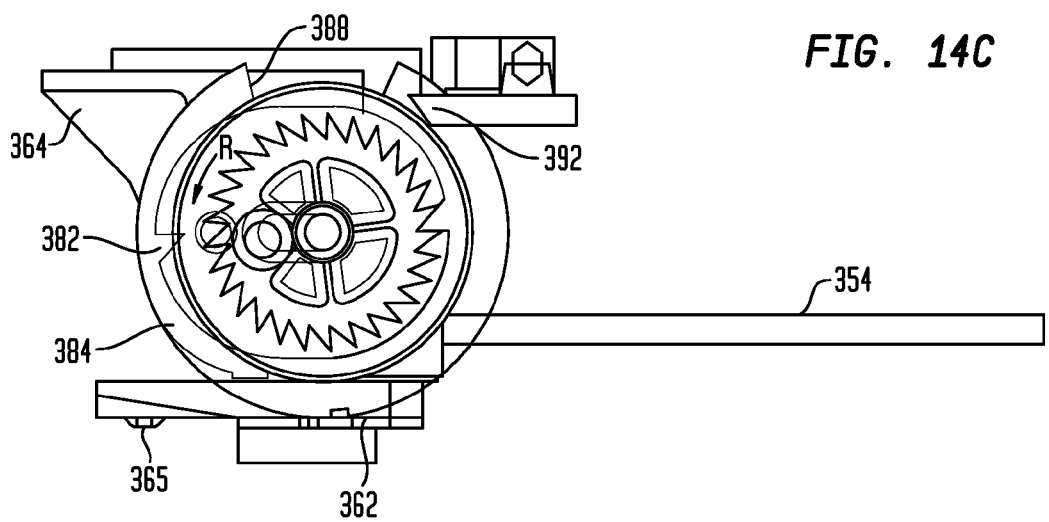

Referring to FIG. 14C, the indexer 354 continues to move distally until the trigger is completely compressed. As the indexer 354 moves to its distal-most position, the upper slot 362 continues to urge the lockout counter boss to move distally. When the indexer 354 has advanced to its distal-most position (FIG. 14C), the indexer 154 may move in a proximal direction (to the right) as the trigger opens. As the indexer 354 moves proximally, the indexer will, in turn, move the lockout counter 364 in a proximal direction so that the second tooth 382 on the lockout counter engages the teeth on the underside of the lockout indicator 375. The second tooth 382 on the lockout counter preferably further rotates the lockout counter 375 in a counterclockwise direction designated $R_1$.

In one embodiment, one complete firing cycle will result in the lockout counter 364 moving distally and then proximally. As the lockout counter moves distally to its distal-most position, the lockout counter 364 will rotate the lockout indicator 375 another about 1/58 of a rotation. As the lockout counter 364 moves to its proximal-most position, the lockout counter will again rotate the lockout indicator 375 about 1/58 of a rotation. Thus, each complete firing cycle will result in the lockout indicator 375 rotating about 1/29 of a rotation. Eventually, the lockout indicator 375 will rotate completely so that the lockout flange 392 is aligned with the lockout slot 388 formed in the main ledge 384 of the lockout indicator. In other embodiments, the lockout indicator may rotate more or less than the example provided below.

Figure 14D:
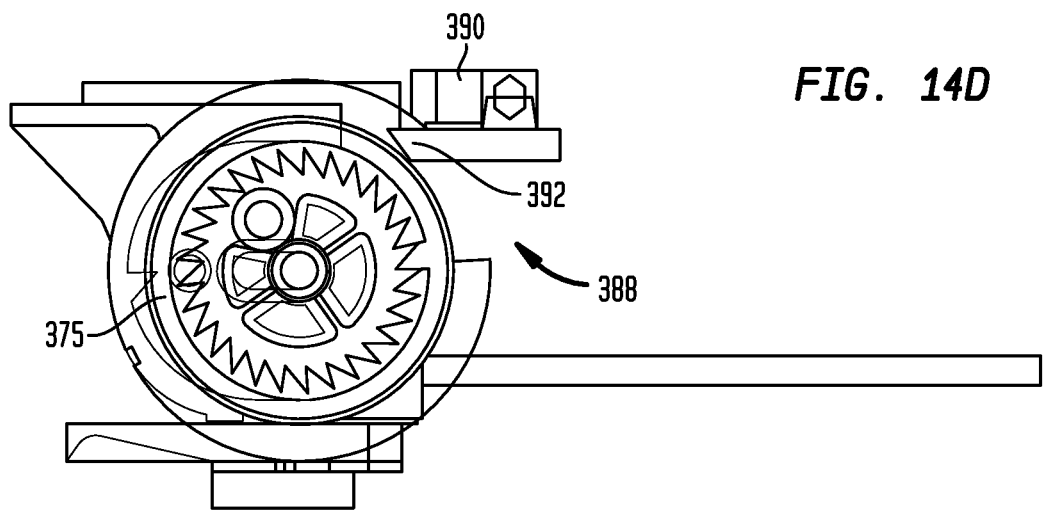

FIG. 14D shows the lockout indicator system immediately before the firing system is locked from further firing. A lockout condition may occur after all of the surgical fasteners have been dispensed. In FIG. 14D, the lockout indicator 375 has rotated so that the lockout flange 394 is adjacent an edge of the lockout slot 388.

Figure 14E:
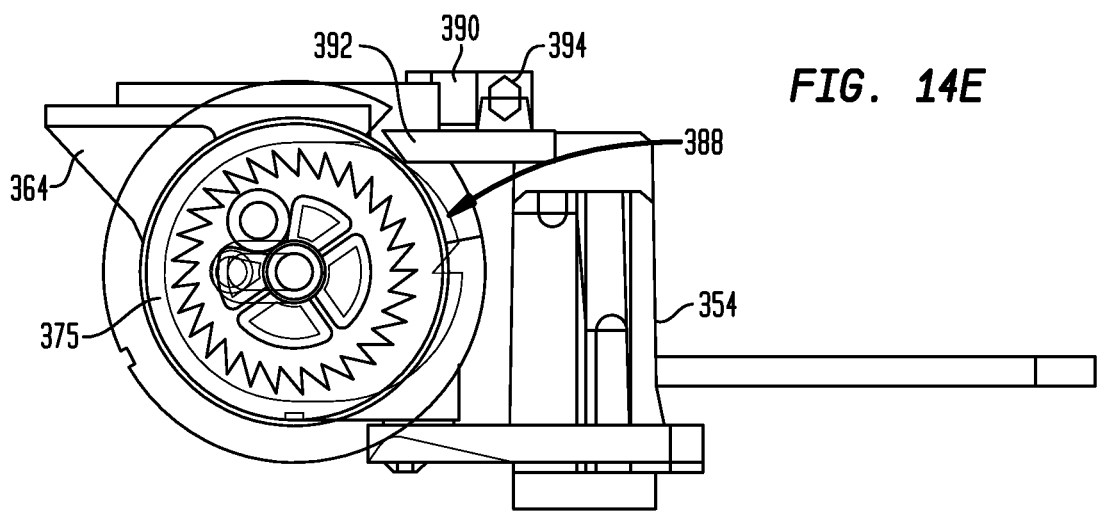

Referring to FIG. 14E, in one embodiment, as the indexer 354 moves proximally at the end of a trigger squeeze, the lockout counter 364 rotates the lockout indicator 375 in a counterclockwise direction so that the lockout flange 392 is aligned with the lockout slot 388. Once the lockout flange 392 is aligned with the lockout slot 388, the lockout pin 390 drops into the lockout slot for locking the firing system. The lockout pin 390 may be urged to drop by the lockout pin spring 394.

Figure 15A:
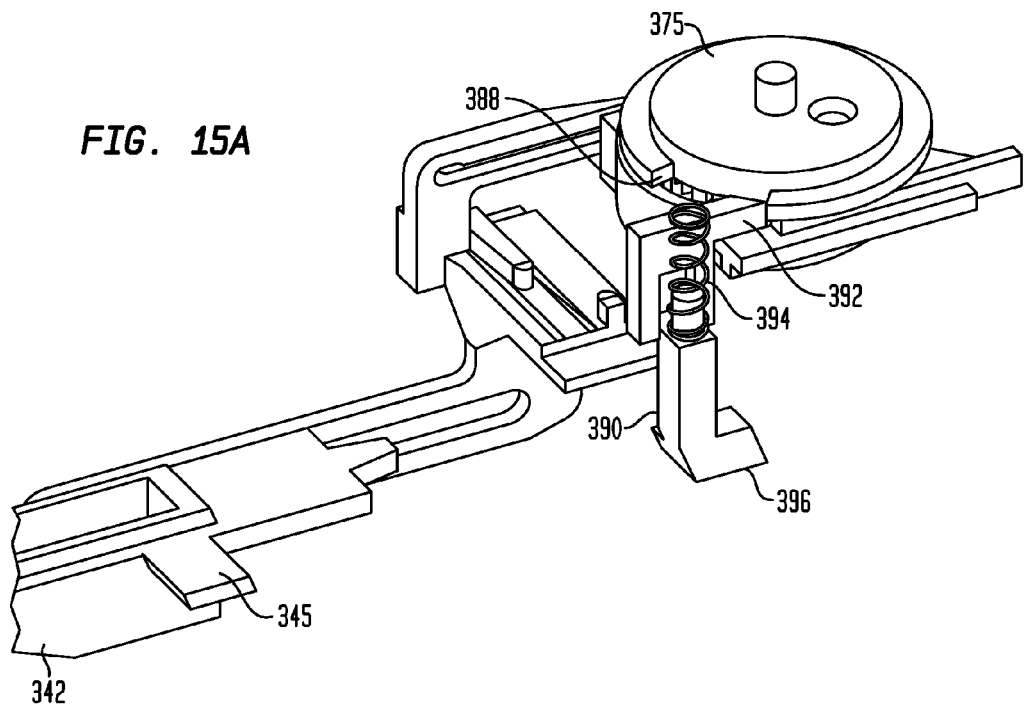
FIGS. 15A-15E show other perspective views of the lockout system shown in FIGS. 13A-13B and 14A-14E, in accordance with one embodiment of the present invention.

Referring to FIG. 15A, in one embodiment, after all of the surgical fasteners are dispensed, the lockout indicator 375 has rotated so that the lockout flange 392 is aligned with the lockout slot 388. At this stage, the lockout pin spring 394 drops the lockout pin 390 so that a catch 396 at a lower end of the lockout pin 390 is aligned with a flange 345 on the yoke 342.

Figure 15B:
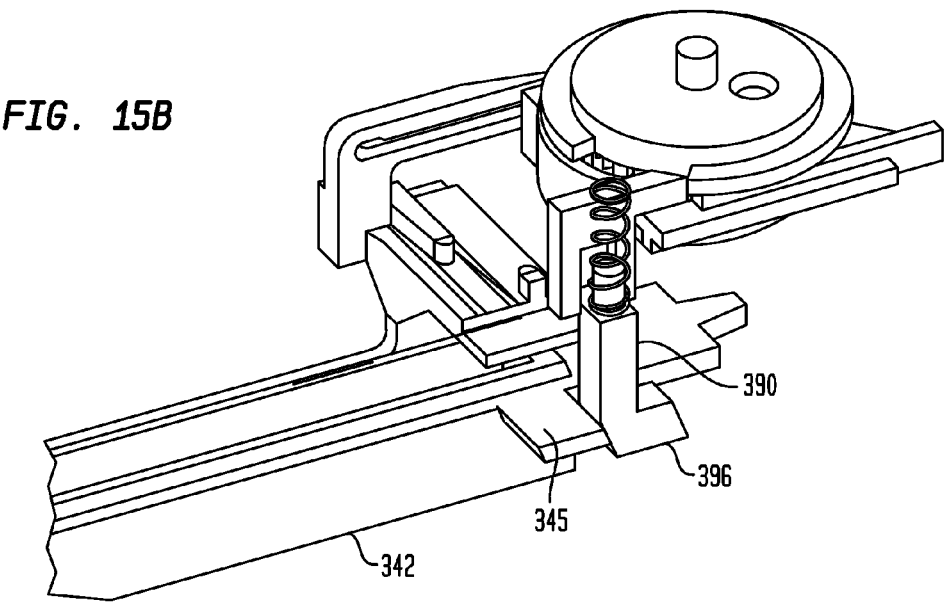
Figure 15C:
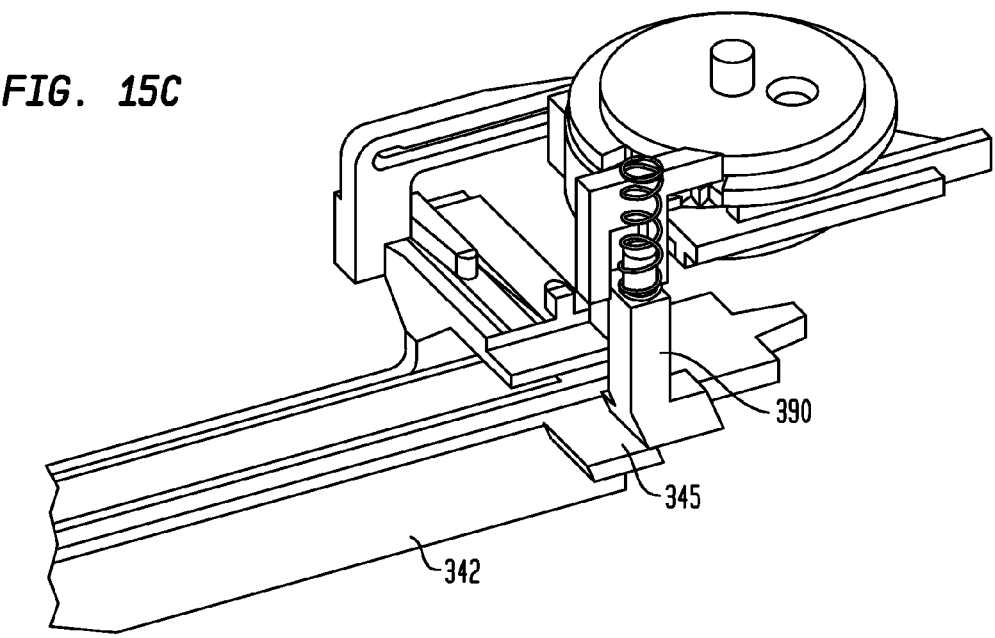

Referring to FIG. 15B, in one embodiment, during the next firing cycle the yoke 342 moves distally so that the yoke flange 345 engages the proximal end of the catch 396 of the lockout pin 390. Referring to FIG. 15C, in one embodiment, as the yoke moves distally, the yoke flange 345 forces the catch 396 at the lower end of the lockout pin 390 to move upwardly as the yoke 342 continues to move in a distal direction.

Figure 15D:
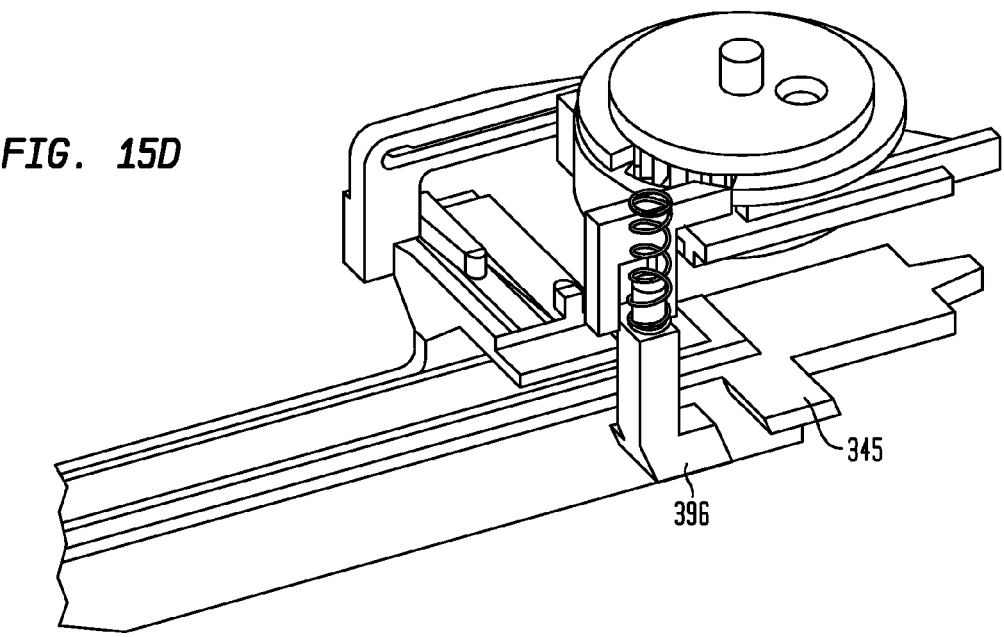
Figure 15E:
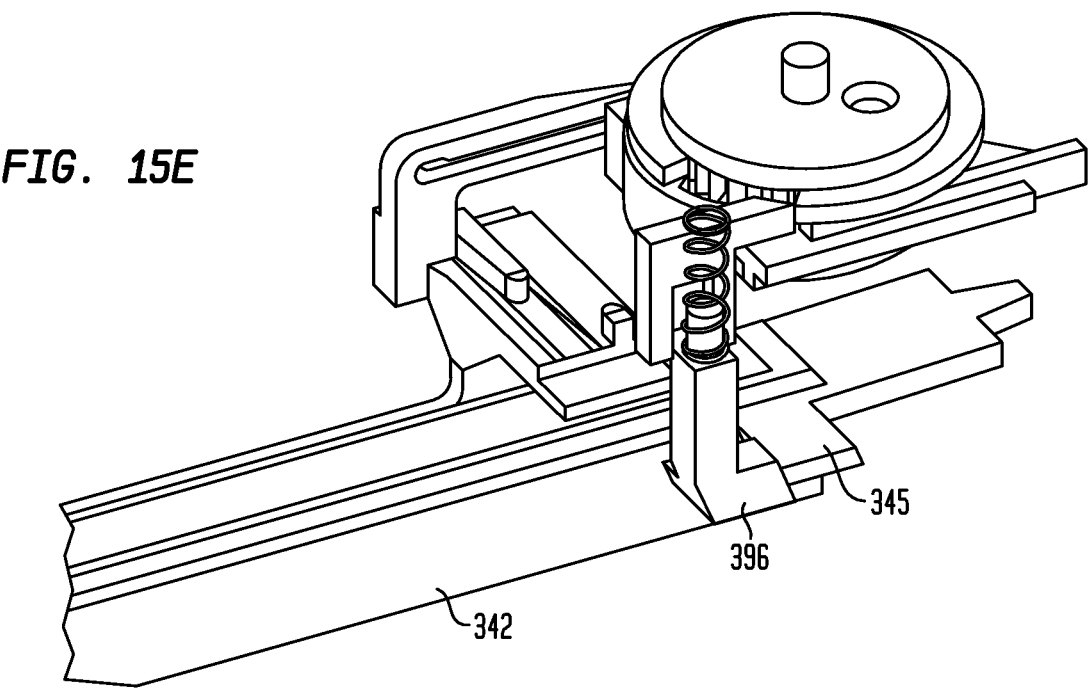

Referring to FIG. 15D, in one embodiment, during a later stage, the yoke flange 345 moves distal of the catch 396. In FIG. 15E, the yoke 342 is constrained from moving in a proximal direction by the catch 396. At this stage, the trigger is preferably completely closed and is prevented from returning to the open trigger position by the engagement of the catch 396 with the yoke flange 345.

Referring to FIG. 16A, in one embodiment, a surgical fastener 432 has a distal end 450 and a proximal end 452. The surgical fastener 432 includes a first leg 454 having a first tip 456 adjacent the distal end 450. The surgical fastener preferably includes a second leg 458 having a second tip 460 adjacent the distal end 450. The proximal end 452 of the surgical fastener 432 includes a bridge 462 connecting the first and second legs 454, 458. The bridge may include a concave inner surface 465 and a convex outer surface 467.

Referring to FIGS. 16B and 16C, the first leg 454 desirably ends at a first blind via 480 and the second leg 458 desirably ends at a second blind via 482. The respective blind vias 480, 482 may be formed in the trailing faces of the tips and are preferably located directly over the center of each tip 456, 460. The blind vias 480, 482 are preferably substantially aligned with the distal points of the tips to avoid tip bending and/or to direct forces for insertion directly behind each of the penetrating distal points.

Referring to FIGS. 17A-17C, in one embodiment, a surgical fastener 532 includes ribs 572 provided on outer surfaces of the first and second legs 554, 558. The surgical fastener 532 is deployed by an insertion fork 520 having a distal end 524 with a first prong 590 and a second prong 594. The first prong 590 includes an inner groove 592 that slides over the first rib 572. The second prong 594 preferably includes a second inner groove 596 adapted to slide over a second rib (not shown) on the second leg 558.

FIG. 17B shows the first and second prongs 590, 594 of the insertion fork 520 sliding over the ribs on the first and second legs of the surgical fastener 532. FIG. 17C shows the prongs 590, 594 fully seated over the first and second legs 554, 558 of the surgical fastener 532. The insertion fork 520 desirably provides rigidity to the surgical fastener 532 during implantation of the surgical fastener into tissue. In one embodiment, the distal ends of the first and second prongs 590, 594 are desirably axially aligned with the first and second tips 556, 560 at the distal end of the surgical fastener. Insertion force is preferably transmitted to the surgical fastener 532 by the distal ends of the tines 590, 594 and by a concave seat 525 of the insertion fork 520.

Figure 18A:
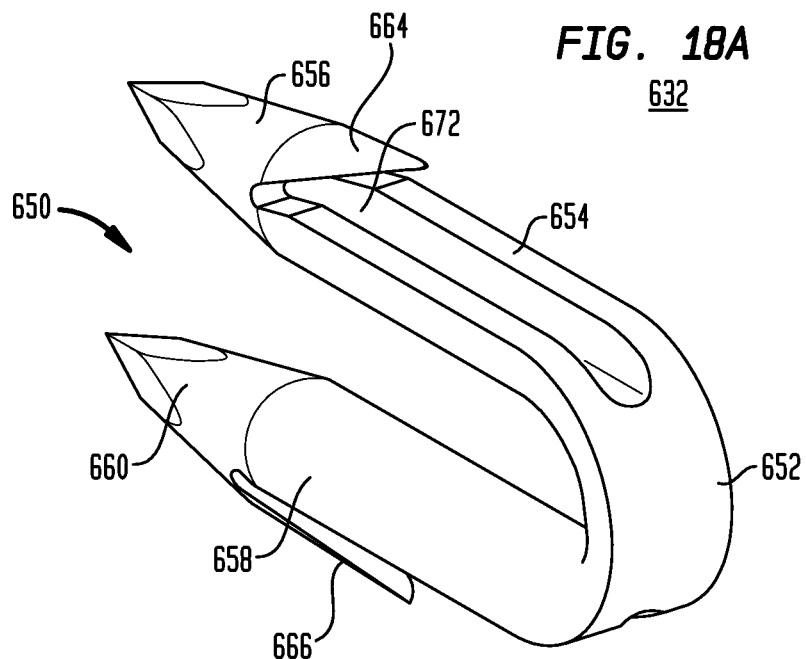
FIGS. 18A-18B show a surgical fastener, in accordance with one embodiment of the present invention.
Figure 18B:
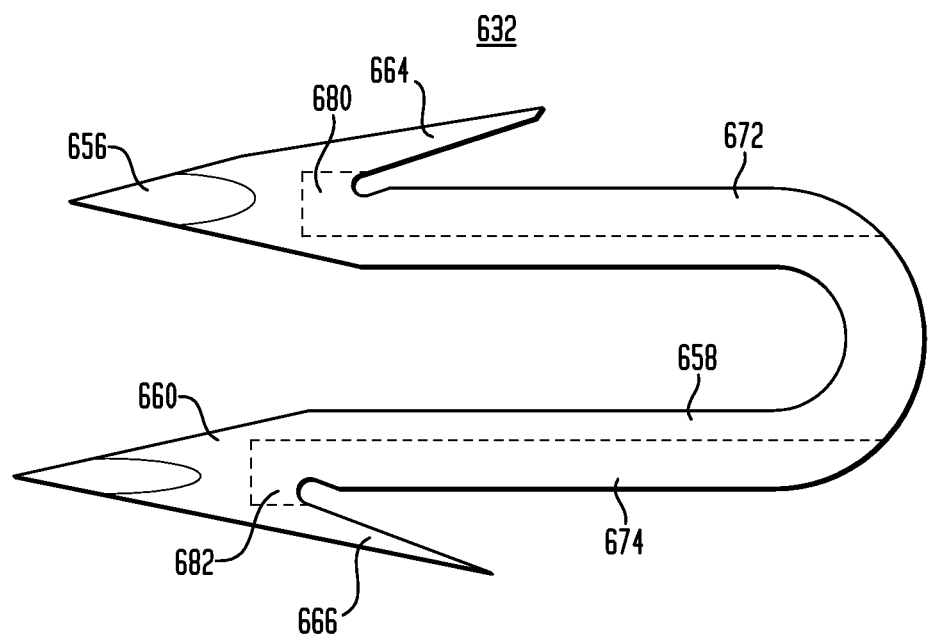

Referring to FIGS. 18A and 18B, in one embodiment, a surgical fastener 632 includes a first leg 654 having a first tip 656 and a second leg 658 having a second tip 660. The first leg 654 includes a first groove 672 that extends from a proximal end 652 toward a distal end 650 of the surgical fastener 632. The second leg 658 has a second groove 674 that is similarly formed as the first groove 672. As shown in FIG. 18B, the first pointed tip 656 is staggered from the second pointed tip 660. The staggered tips desirably reduce penetration force by staggering the peak forces encountered during insertion. The surgical fastener also desirably includes at least one barb 664 on the first leg 672 that is staggered from the at least one barb 666 on the second leg 674.

Figure 19A:
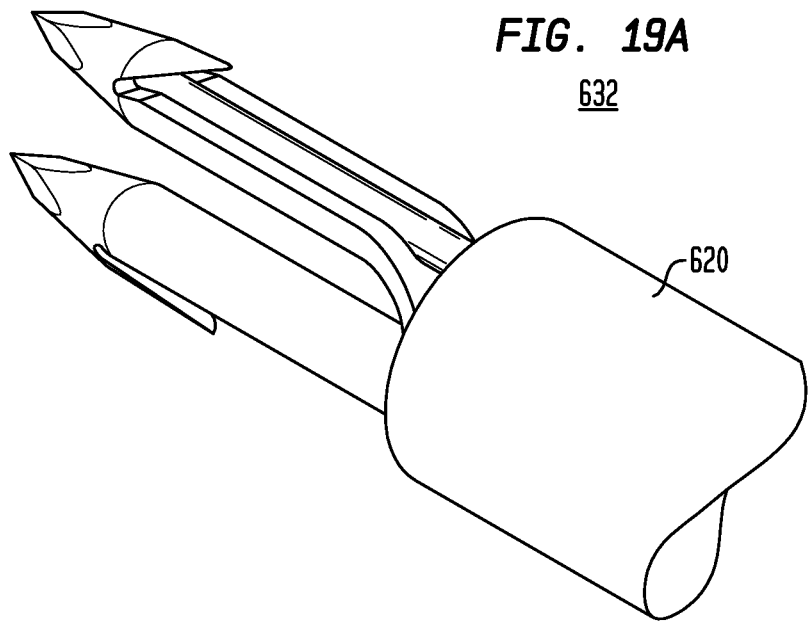
FIGS. 19A-19C show a distal end of an insertion tool for implanting the surgical fastener of FIGS. 18A-18B, in accordance with one embodiment of the present invention.
Figure 19B:
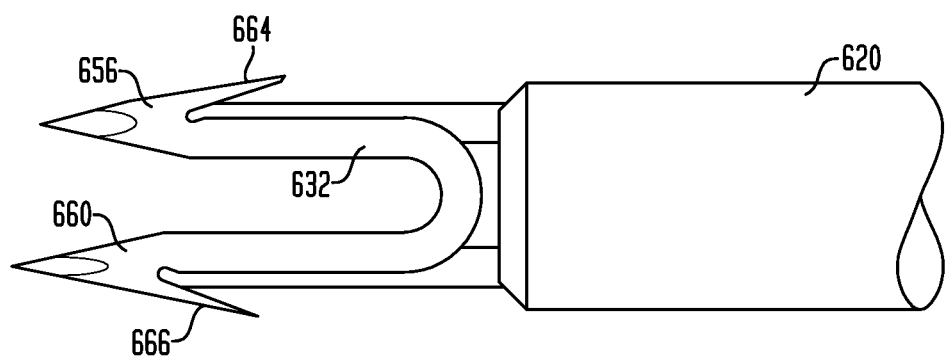
Figure 19C:
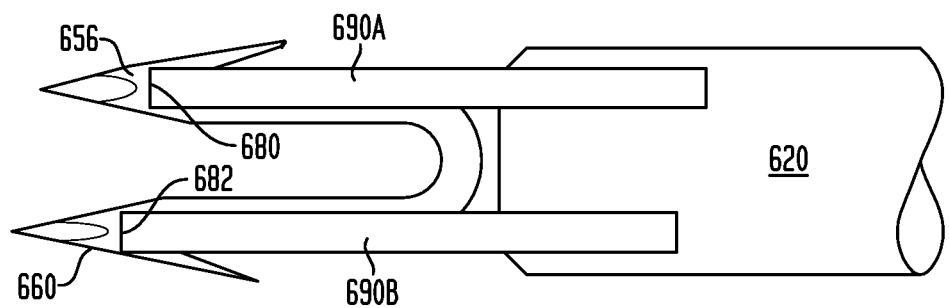

Referring to FIGS. 19A-19C, in one embodiment, the surgical fastener 632 of FIGS. 18A and 18B is implanted using an insertion tool 620 having staggered prongs 690A, 690B. The surgical fastener preferably includes blind vias 680, 682 that are aligned with the pointed tips 656, 660. The staggered prongs 690A, 690B of the insertion tool 620 are insertable into the blind vias 680, 682 located behind the pointed tips 656, 660. The prongs provide support for the surgical fastener as the fastener is implanted, and provide an insertion force that is applied to the surgical fastener distal to the proximal end of the surgical fastener.

FIGS. 20A-20C show the surgical fastener 632 of FIGS. 18A-18B being implanted using the insertion tool 620 of FIGS. 19A-19C. Referring to FIG. 20A, in one embodiment, a distal ends of an applicator instrument is abutted against a prosthetic device 670 overlying tissue T. The insertion tool 620 is advanced to the distal end of the applicator instrument 600 so that the first and second pointed tips 656, 660 are adjacent the prosthetic device. As shown in FIG. 20A, the second pointed tip 660 engages the prosthetic device before the first pointed tip 656, thereby staggering the peak forces encountered during implantation. FIGS. 20B and 20B-1 show the pointed tips 656, 660 of the surgical fastener 632 being pressed through the prosthetic device and into the tissue. The staggered tines 690A, 690B at the distal ends of insertion tool 620 support the pointed tips 656, 660 of the surgical fastener and preferably extend through the prosthetic device and into the tissue during insertion of the surgical fastener. FIG. 20C shows the surgical fastener 632 in place for holding the prosthetic device 670 to the tissue T after the insertion tool has been retracted. The bridge 662 of the surgical fastener preferably overlies one of more strands of the prosthetic device for capturing the strands between the first and second legs 654, 658.

Figure 21A:
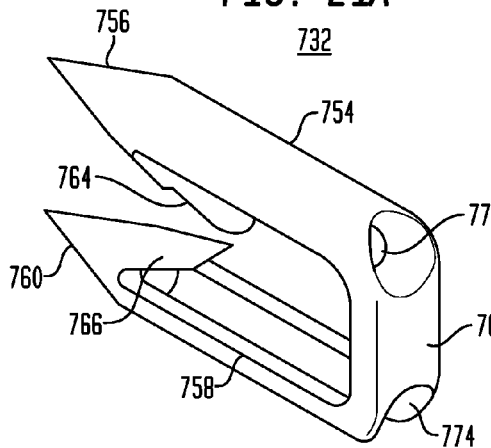
FIGS. 21A-21B show a surgical fastener, in accordance with one embodiment of the present invention.
Figure 21B:
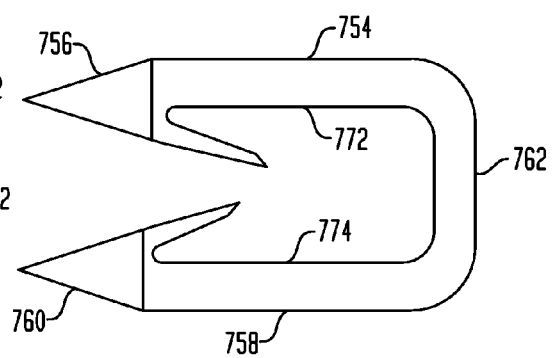

Referring to FIGS. 21A and 21B, in one embodiment, a surgical fastener 732 includes internally facing barbs 764, 766. Referring to FIG. 21B, in one embodiment, the barbs are preferably staggered from the distal end of the surgical fastener. After implantation, the internally facing barbs 764, 766 desirably squeeze tissue inside the legs, thereby increasing the required pull-out force. The surgical fastener desirably includes a bridge 762 having a substantially flat inner surface that allows for greater capture of the prosthetic device and further aids in alignment of the surgical fastener as it is advanced toward the distal end of an insertion tube.

Although the present invention is not limited by any particular theory of operation, it is believed that the internally facing barbs provide a greater point to point distance for a given surgical element width, thereby reducing the chance that the surgical fastener will not capture a strand when anchoring large open-pore meshes. The internally facing barbs enable the external surfaces of the legs 754, 758 to be straight, thereby facilitating feeding the surgical fastener inside a tube.

Figure 22A:
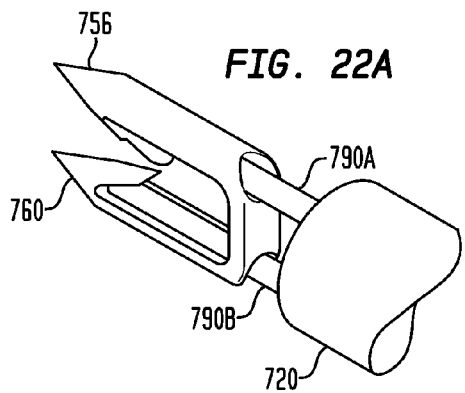
FIGS. 22A-22C show an insertion tool for implanting the surgical fastener of FIGS. 21A-21B, in accordance with one embodiment of the present invention.
Figure 22B:
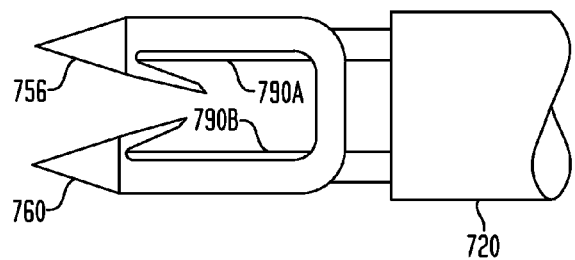
Figure 22C:
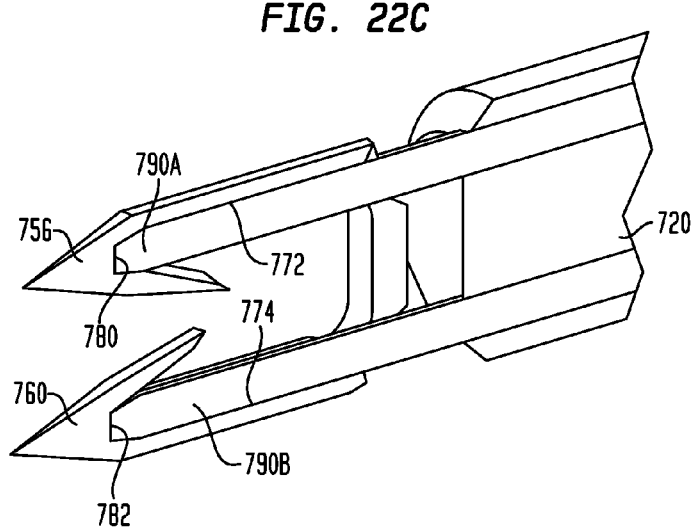

Referring to FIGS. 21A and 21B, in one embodiment, the legs 754, 758 of the surgical fastener 732 have opposing inner grooves 772, 774. The grooves 772, 774 are desirably accessible at the proximal end of the surgical fastener and adjacent the bridge 762 of the surgical fastener. The inner grooves formed in the first and second legs 754, 758 preferably guide tines on an insertion tool to blind vias at the distal ends of the legs 754, 758. It is believed that the conical-shaped tips 756, 760 increase penetration force compared to tips that are chiseled, and that the conical-shaped tips may also increase pull-out force by not cutting a path, but rather stretching the hole created by the conical tips. FIGS. 22A-22C show an insertion tool 720 having distal tines 790A, 790B that are advanceable into the inner grooves 772, 774. The distal ends of the tines are preferably abutted against the blind vias 680, 682 that terminate adjacent the tips 756, 760.

Figure 23:
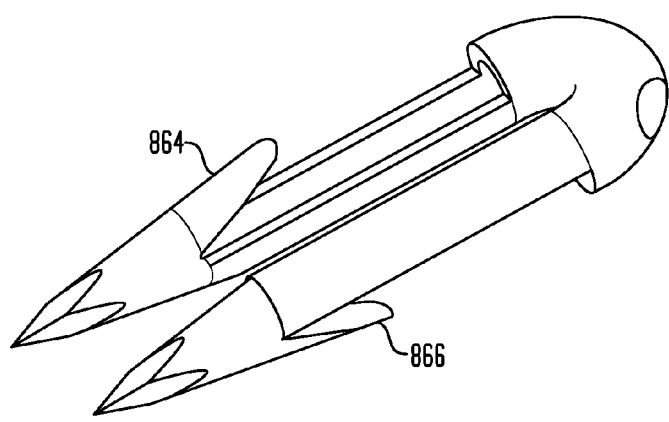
FIG. 23 shows a perspective view of a surgical fastener having out of plane barbs, in accordance with one embodiment of the present invention.
Figure 24:
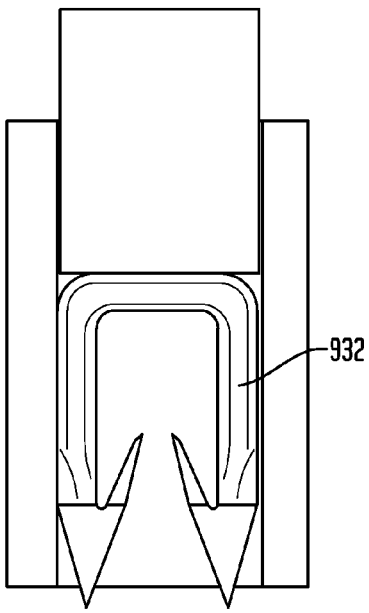
FIG. 24 shows a surgical fastener, in accordance with one embodiment of the present invention.

Referring to FIG. 23, in one embodiment, a surgical fastener 832 has barbs 864, 866 that are set out of plane. The out of plane barbs preferably enhance holding force after implantation in tissue. Referring to FIG. 24, in one embodiment, a surgical fastener 932 is pin-less, and is desirably pushed from a proximal end during deployment into a prosthetic device, mesh or tissue.

Figure 25A:
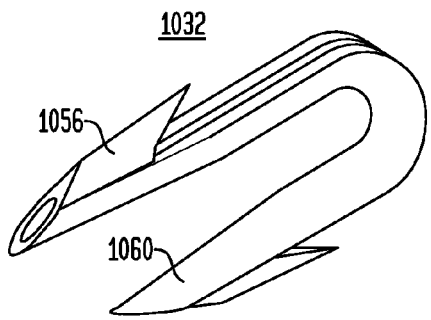
FIG. 25A shows a perspective view of a surgical fastener, in accordance with one embodiment of the present invention.
Figure 25B:
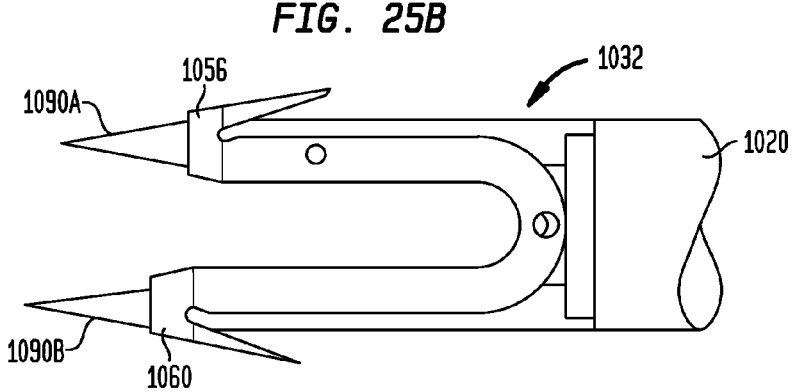
FIG. 25B shows an insertion tool for deploying the surgical fastener of FIG. 25A, in accordance with one embodiment of the present invention.

Referring to FIGS. 25A and 25B, in one embodiment, a surgical fastener 1032 is deployed using needle-assisted insertion. The surgical fastener 1032 has barbed tips 1056, 1060 having through holes. In one embodiment, the surgical fastener 1032 is made of relatively soft material, but may still be inserted through tough prosthetic devices, meshes and tissue using a needle-assist insertion tool 1020 having needle tips 1090A, 1090B that are passable through the through holes in the tips 1056, 1060.

Figure 26:
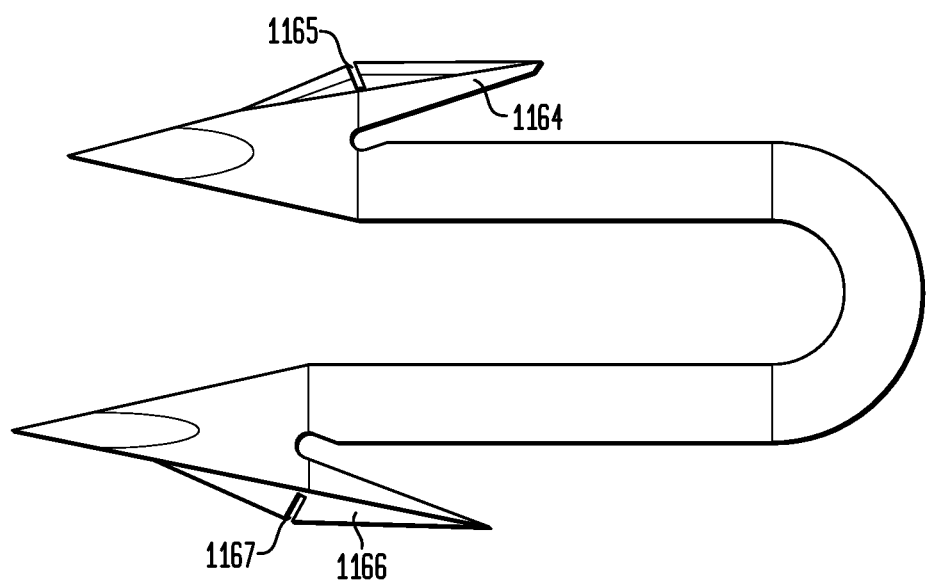
FIG. 26 shows a front view of a surgical fastener, in accordance with one embodiment of the present invention.

Referring to FIG. 26, in one embodiment, a surgical fastener 1132 has one-way barbs. Each of the barbs 1164, 1166 preferably has a notch 1165, 1167 that enables the barbs to flex inwardly during insertion and outwardly during retraction, thereby making it difficult to remove the barbs from prosthetic devices, mesh and/or tissue during retraction of the surgical fastener.

Figure 27:
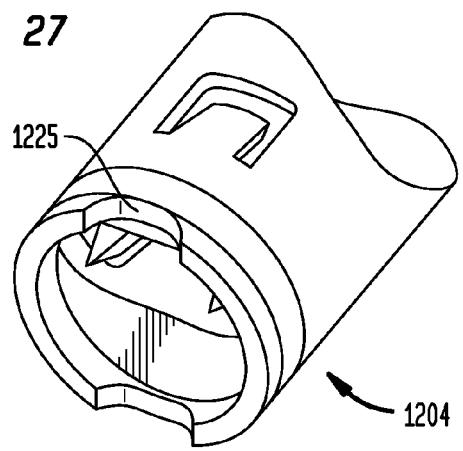
FIG. 27 shows a distal end of an applicator instrument for dispensing surgical fasteners, in accordance with one embodiment of the present invention.
Figure 28A:
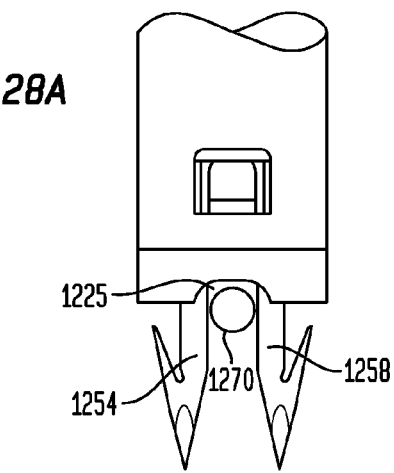
FIGS. 28A and 28B show a method of using the applicator instrument shown in FIG. 27 for dispensing a surgical fastener, in accordance with one embodiment.
Figure 28B:
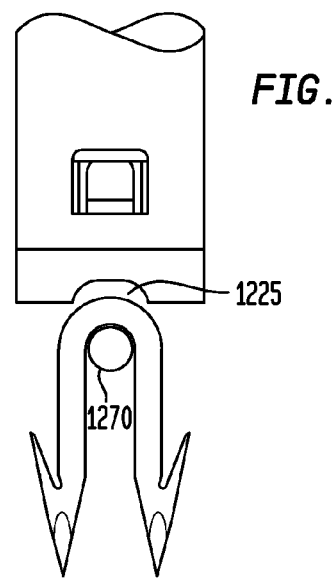

Referring to FIG. 27, in one embodiment, an applicator instrument 1200 has an alignment notch 1225 at a distal 1204 end therefor. As shown in FIGS. 28A and 28B, in one embodiment, the alignment notch 1225 preferably facilitates aligning the instrument over a strand 1270 of a prosthetic device to insure that the strand is captured between the legs 1254, 1258 of the surgical fastener 1232 when deployed from the applicator instrument.

Figure 29:
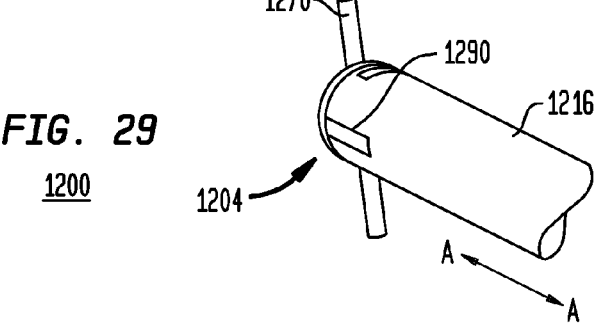
FIG. 29 shows a distal end of an applicator instrument for dispensing surgical fasteners, in accordance with one embodiment of the present invention.

Referring to FIG. 29, in one embodiment, an applicator instrument 1200 has an outer tube 1216 having one or more alignment markings 1290 extending away from the distal end 1204 and along the outer surface of the outer tube 1216. The alignment marking 1290 preferably extends along the longitudinal axis A-A of the instrument for providing an alignment reference marking for aligning the instrument over a strand 1270 of a prosthetic device.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A firing system for an applicator instrument adapted to dispense surgical fasteners comprising:
   a housing;
   an elongated shaft extending from said housing;
   a firing rod disposed within said elongated shaft;
   a firing rod release engageable with said firing rod for preventing distal movement of said firing rod during at least one stage of a firing cycle;
   a trigger mounted to said housing;
   a firing spring adapted to transfer energy to said firing rod for advancing said firing rod distally toward the distal end of said elongated shaft, said firing spring having a first end connected with said firing rod and a second end adapted for being sequentially coupled and decoupled from said trigger during said firing cycle;
   wherein said firing cycle comprises
      an initial stage in which said trigger is open and decoupled from said firing spring, and said firing spring is at least partially compressed, and
      a piloting stage during which said firing rod release is disengaged from said firing rod for enabling distal movement of said firing rod, and said trigger is compressible a first distance for coupling said trigger with said firing spring for moving said at least partially compressed firing spring distally, which, in turn, moves said firing rod distally at a first rate of speed that is proportional to the movement of said trigger.

2. The firing system as claimed in claim 1, wherein said firing cycle further comprises:
   after the piloting stage, an energy storing stage in which said firing rod release engages said firing rod for preventing distal movement of said firing rod, and said trigger is further movable a second distance for further compressing and storing energy in said firing spring.

3. The firing system as claimed in claim 2, wherein said firing cycle further comprises:
   after the energy storing stage, a firing stage in which said firing rod release automatically disengages from said firing rod so that said firing rod is free to move toward the distal end of said elongated shaft and said compressed firing spring transfers the energy stored therein to said firing rod for rapidly advancing said firing rod toward the distal end of said elongated shaft at a second rate of speed that is greater than both the first rate of speed and the movement of said trigger.

4. The firing system as claimed in claim 3, wherein said firing cycle further comprises:
   after the firing stage, a decoupling stage during which said trigger is further compressible a third distance for decoupling said trigger from said firing spring whereupon said firing rod is free to move toward the proximal end of said elongated shaft.

5. The firing system as claimed in claim 4, wherein said firing system further comprises an advancer disposed within said elongated shaft and being moveable in proximal and distal directions along said elongated shaft, and wherein said firing cycle further comprises:
   after the firing stage, a surgical fastener advancing stage during which said trigger is further compressible a fourth distance for moving said advancer toward the distal end of said elongated shaft for moving surgical fasteners toward the distal end of said elongated shaft.

6. The firing system as claimed in claim 5, wherein said firing cycle further comprises:
   after the surgical fastener advancing stage, a retraction stage during which said trigger moves from a compressed position to the open position of the initial stage for moving said advancer in a proximal direction.

7. The firing system as claimed in claim 6, further comprising a spring block disposed within said housing and engageable with a proximal end of said firing spring, wherein said spring block is adapted to move proximally and distally along the longitudinal axis defined by said elongated shaft.

8. The firing system as claimed in claim 7, wherein during the energy storing stage, said trigger is coupled with said spring block for moving said spring block distally, which, in turn, further compresses said firing spring.

9. The firing system as claimed in claim 8, further comprising a primary latch coupled with said trigger and being adapted to couple said trigger with said spring block during the piloting, energy storing, and firing stages, and decouple said trigger from said spring block during the decoupling, surgical fastener advancing, and retraction stages.

10. The firing system as claimed in claim 9, wherein at the beginning of the firing stage said spring block contacts said firing rod release for disengaging said firing rod release from said firing rod so that said firing rod may move distally.

11. A firing system for a surgical fastener applicator instrument including a housing and an elongated shaft extending from said housing, said firing system comprising:
   a firing rod disposed within said elongated shaft and being movable proximally and distally along a longitudinal axis;
   a firing spring block disposed within said housing and being adapted to move in proximal and distal directions along the longitudinal axis;
   a firing spring having a distal end connected with said firing rod and a proximal end engaging said firing spring block; and
   a trigger mounted to said housing for driving said firing system, said trigger including a primary latch for sequentially coupling and decoupling said trigger from said firing spring block during a firing cycle, wherein said firing spring is adapted to advance a distal end of said firing rod beyond a distal end of said applicator instrument for shooting a surgical fastener from the distal end of said elongated shaft.

12. The firing system as claimed in claim 11, wherein said firing cycle comprises:
   an initial stage in which said trigger is open, said trigger is decoupled from said firing spring block, and said firing spring is at least partially compressed; and
   a piloting stage in which said firing rod is free to move toward the distal end of said elongated shaft, and said trigger is compressible a first distance for coupling said trigger with said firing spring block for moving said at least partially compressed firing spring distally, which, in turn, moves said firing rod distally at a first rate of speed that is proportional to the movement of said trigger.

13. The firing system as claimed in claim 12, wherein the compression level of said firing spring remains unchanged during the piloting stage.

14. The firing system as claimed in claim 12, wherein said firing cycle further comprises:
   after the piloting stage, an energy storing stage in which said trigger is further compressible a second distance for further compressing and storing energy in said firing spring while said firing rod release engages said firing rod for preventing distal movement of said firing rod.

15. The firing system as claimed in claim 14, wherein said firing cycle further comprises:
   after the energy storing stage, a firing stage in which said firing rod release automatically disengages from said firing rod so that said firing rod is free to move toward the distal end of said elongated shaft and said firing spring transfers the energy stored therein to said firing rod for rapidly advancing said firing rod toward the distal end of said elongated shaft at a second rate of speed that is greater than the first rate of speed.

16. The firing system as claimed in claim 15, wherein said firing cycle further comprises:
   after the firing stage, a decoupling stage during which said trigger is further compressible a third distance for decoupling said trigger from said firing spring and said firing rod so that said firing rod may move proximally.

17. The firing system as claimed in claim 16, wherein said firing system further comprises an advancer disposed within said elongated shaft and being moveable between the proximal and distal ends of said elongated shaft for moving surgical fasteners toward the distal end of said elongated shaft, and wherein said firing cycle further comprises:
   after the firing stage, a surgical fastener advancing stage during which said trigger is further compressible a fourth distance for moving said advancer toward the distal end of said elongated shaft so as to move said surgical fasteners toward the distal end of said elongated shaft.

18. The firing system as claimed in claim 17, wherein during the energy storing stage, said trigger is coupled with said firing spring block for moving said firing spring block distally, which, in turn, compresses said firing spring.

19. The firing system as claimed in claim 18, wherein said primary latch is adapted to couple said trigger with said spring block during the piloting, energy storing, and firing stages, and decouple said trigger from said spring block during the decoupling, surgical fastener advancing, and retraction stages.

20. A firing system for an applicator instrument adapted to dispense surgical fasteners comprising:
    a housing;
    an elongated shaft extending from said housing;
    a firing rod disposed within said elongated shaft;
    a firing rod release engageable with said firing rod for preventing distal movement of said firing rod during at least one stage of a firing cycle, wherein said firing rod release automatically disengages from said firing rod during a firing stage of said firing cycle;
    a trigger mounted to said housing;
    a firing spring adapted to transfer energy to said firing rod for advancing said firing rod distally toward the distal end of said elongated shaft, said firing spring having a first end connected with said firing rod and a second end adapted for being sequentially coupled and decoupled from said trigger during said firing cycle;
    wherein said firing cycle comprises
        an initial stage in which said trigger is open and decoupled from said firing spring, and said firing spring is at least partially compressed, and
        a piloting stage during which said firing rod release is disengaged from said firing rod for enabling distal movement of said firing rod, and said trigger is compressible a first distance for coupling said trigger with said firing spring for moving said at least partially compressed firing spring distally, which, in turn, moves said firing rod distally at a first rate of speed that is proportional to the movement of said trigger.

* * * * *